US012398191B2

(12) United States Patent
Veatch et al.

(10) Patent No.: US 12,398,191 B2
(45) Date of Patent: Aug. 26, 2025

(54) BRAF-SPECIFIC TCRS AND USES THEREOF

(71) Applicants: FRED HUTCHINSON CANCER CENTER, Seattle, WA (US); UNIVERSITY OF WASHINGTON, Seattle, WA (US)

(72) Inventors: Joshua Veatch, Seattle, WA (US); Stanley R. Riddell, Sammamish, WA (US); Sylvia Lee, Seattle, WA (US)

(73) Assignees: FRED HUTCHINSON CANCER CENTER, Seattle, WA (US); UNIVERSITY OF WASHINGTON, Seattle, WA (US)

( * ) Notice: Subject to any disclaimer, the term of this patent is extended or adjusted under 35 U.S.C. 154(b) by 1344 days.

(21) Appl. No.: 16/638,339

(22) PCT Filed: Aug. 10, 2018

(86) PCT No.: PCT/US2018/046350
§ 371 (c)(1),
(2) Date: Feb. 11, 2020

(87) PCT Pub. No.: WO2019/033057
PCT Pub. Date: Feb. 14, 2019

(65) Prior Publication Data
US 2020/0223899 A1   Jul. 16, 2020
US 2021/0238250 A9   Aug. 5, 2021

Related U.S. Application Data

(60) Provisional application No. 62/544,695, filed on Aug. 11, 2017.

(51) Int. Cl.
| | | |
|---|---|---|
| A61K 39/395 | (2006.01) | |
| A61K 35/17 | (2015.01) | |
| A61K 40/11 | (2025.01) | |
| A61K 40/32 | (2025.01) | |
| A61K 40/42 | (2025.01) | |
| A61P 35/00 | (2006.01) | |
| C07K 14/725 | (2006.01) | |
| C12N 5/0783 | (2010.01) | |
| C12N 7/00 | (2006.01) | |
| C12N 15/86 | (2006.01) | |
| A61K 38/00 | (2006.01) | |

(52) U.S. Cl.
CPC .......... *C07K 14/7051* (2013.01); *A61K 35/17* (2013.01); *A61K 40/11* (2025.01); *A61K 40/32* (2025.01); *A61K 40/4251* (2025.01); *A61P 35/00* (2018.01); *C12N 5/0636* (2013.01); *C12N 7/00* (2013.01); *C12N 15/86* (2013.01); *A61K 38/00* (2013.01); *A61K 2239/57* (2023.05); *C12N 2740/10043* (2013.01)

(58) Field of Classification Search
None
See application file for complete search history.

(56) References Cited

U.S. PATENT DOCUMENTS

| | | |
|---|---|---|
| 5,283,173 A | 2/1994 | Fields et al. |
| 5,420,032 A | 5/1995 | Marshall et al. |
| 5,468,614 A | 11/1995 | Fields et al. |
| 6,410,319 B1 | 6/2002 | Raubitschek et al. |
| 6,833,252 B1 | 12/2004 | Dujon et al. |
| 7,446,191 B2 | 11/2008 | Jensen |
| 7,514,537 B2 | 4/2009 | Jensen |
| 8,697,359 B1 | 4/2014 | Zhang |
| 8,822,647 B2 | 9/2014 | Jensen |
| 9,574,000 B2 | 2/2017 | Langermann et al. |
| 2004/0002092 A1 | 1/2004 | Arnould et al. |
| 2004/0087025 A1 | 5/2004 | June et al. |
| 2006/0078552 A1 | 4/2006 | Arnould et al. |
| 2006/0153826 A1 | 7/2006 | Arnould et al. |
| 2006/0206949 A1 | 9/2006 | Arnould et al. |
| 2007/0117128 A1 | 5/2007 | Smith et al. |
| 2010/0065818 A1 | 3/2010 | Kim et al. |
| 2011/0189141 A1 | 8/2011 | Kieback et al. |
| 2011/0243972 A1 | 10/2011 | Jaffee |
| 2011/0301073 A1 | 12/2011 | Gregory et al. |
| 2014/0068797 A1 | 3/2014 | Doudna et al. |
| 2014/0186843 A1 | 7/2014 | Zhang et al. |
| 2015/0337369 A1 | 11/2015 | Davis et al. |

FOREIGN PATENT DOCUMENTS

| | | |
|---|---|---|
| WO | WO 9709433 A1 | 3/1997 |
| WO | 2007/002811 A2 | 1/2007 |
| WO | WO 2013025779 A1 | 2/2013 |
| WO | WO 2014031687 A1 | 2/2014 |
| WO | WO 2015071474 A2 | 5/2015 |

(Continued)

OTHER PUBLICATIONS

Dunn et al., "Directed evolution of human T cell receptor CDR2 residues by phage display dramatically enhances affinity for cognate peptide-MHC without increasing apparent cross-reactivity," *Protein Science* 15:710-721, Jan. 10, 2006.

Lee et al., "Current management and novel agents for malignant melanoma," *Journal of Hematology & Oncology* 5(3):1-7, 2012.

Legut et al., "CRISPR-mediated TCR replacement generates superior anticancer transgenic T cells," *blood* 131(3):311-322, Jan. 18, 2018.

Sharkey et al., "CD4+ T-Cell Recognition of Mutated B-RAF in Melanoma Patients Harboring the V599E Mutation," *Cancer Research* 64(5):1595-1599, Mar. 2004.

(Continued)

*Primary Examiner* — Yunsoo Kim
(74) *Attorney, Agent, or Firm* — Seed IP Law Group LLP

(57) ABSTRACT

The present disclosure provides binding proteins, such as TCRs, that specifically bind various tumor associated antigens (including human BRAFV600E epitope), cells expressing such antigen specific binding proteins, nucleic acids encoding the same, and compositions for use in treating diseases or disorders in which cells express BRAFV600E, such as in cancer.

16 Claims, 20 Drawing Sheets
Specification includes a Sequence Listing.

(56) References Cited

FOREIGN PATENT DOCUMENTS

| WO | 2015/095895 A1 | 6/2015 |
|---|---|---|
| WO | WO 2016040724 A1 | 3/2016 |
| WO | WO 2016054638 A1 | 4/2016 |
| WO | 2016/069647 A1 | 5/2016 |
| WO | WO 2016134333 A1 | 8/2016 |
| WO | 2016/161273 A1 | 10/2016 |
| WO | WO 2017021526 A1 | 2/2017 |
| WO | 2017/096331 A1 | 6/2017 |

OTHER PUBLICATIONS

Veatch et al., "Tumor-infiltrating BRAF$^{V600E}$-specific CD4+ T cells correlated with complete clinical response in melanoma," *The Journal of Clinic Investigation* 128(4):1563-1568, Apr. 2018.
Walseng et al., "A TCR-based Chimeric Antigen Receptor," *Scientific Reports* 7:1-10, Sep. 2017.
GenBank, "T-cell receptor alpha chain, partial [*Homo sapiens*]," Accession No. BAN84546.1, Nov. 21, 2013. (3 pages).
Kobayashi et al., "A new cloning and expression system yields and validates TCRs from blood lymphocytes of patients with cancer within 10 days," *Nature Medicine* 19(11), Nov. 2013. (30 pages).
Abbas et al., "Cellular and Molecular Immunology," Third Edition, pp. 149, 155, 250, 266, 413, 1997. (7 pages).
Altschul et al., "Gapped BLAST and PSI-BLAST: a new generation of protein database search programs," Nucleic Acids Research 25(17):3389-3402, Jul. 16, 1997.
Argast et al., "I-Ppol and I-Crel Homing Site Sequence Degeneracy Determined by Random Mutagenesis and Sequential in Vitro Enrichment," *J. Mol. Biol.* 280:345-353, 1998.
Ashworth et al., "Computational redesign of endonuclease DNA binding and cleavage specificity," *Nature* 441(7093):656-659, Jun. 1, 2006 (NIH Public Access Author Manuscript, available in PMC Dec. 9, 2010) (11 pages).
Belfort et al., "Homing endonucleases: keeping the house in order," *Nucleic Acids Research* 25(17):3379-3388, 1997.
Brentjens et al., "Genetically Targeted T Cells Eradicates Systemic Acute Lymphoblastic Leukemia Xenografts," *Clin Cancer Res* 13(18):5426-5435, Sep. 15, 2007.
Cavallo et al., "2011: the immune hallmarks of cancer," *Cancer Immunol Immunother* 60:319-326, Jan. 26, 2011.
Chapuis et al., "Abstract LB-136: IL-21-derived melanoma-reactive CTL combined with anti-CTLA4 persist, acquire central memory characteristics, and mediate tumor regression in patients with metastatic melanoma," *Cancer Research* 72(8 Suppl):2012. (4 pages).
Chapuis et al., "Transferred melanoma-specific CD8+ T cells persist, mediate tumor regression, and acquire central memory phenotype," *PNAS* 109(12):4592-4597, Mar. 20, 2012.
Chapuis et al., "Transferred WT1-reactive CD8+ T cells can mediate antileukemic activity and persist in post-transplant patients," *Sci Transl Med* 5(174):174ra27, Feb. 27, 2013 (NIH Public Access Author manuscript, available in PMC Jun. 11, 2013) (25 pages).
Chevalier et al., "Design, Activity, and Structure of a Highly Specific Artificial Endonuclease," *Molecular Cell* 10:895-905, Oct. 2002.
Chothia, et al., "The outline structure of the T-cell ab receptor," *The EMBO Journal* 7(12):3745-3755, 1988.
Cole et al., "CD8: Adhesion Molecule, Co-Receptor and Immuno-Modulator," *Cellular & Molecular Immunology* 1(2):81-88, Apr. 2004.
Dangaj et al., "Novel Recombinant Human B7-H4 Antibodies Overcome Tumoral Immune Escape to Potentiate T-Cell Antitumor Responses," Cancer Res 73(15):4820-4829, Aug. 1, 2013.
Desjarlais et al., "Use of a zinc-finger consensus sequence framework and specificity rules to design specific DNA binding proteins," *Proc. Natl. Acad. Sci. USA* 90:2256-2260, Mar. 1993.
Dossett et al., "Adoptive Immunotherapy of Disseminated Leukemia With TCR-transduced, CD8+ T Cells Expressing a Known Endogenous TCR," *Molecular Therapy* 17(4):742-749, 2009.

Dudley et al., "Adoptive Transfer of Cloned Melanoma-Reactive T Lymphocytes for the Treatment of Patients with Metastatic Melanoma," *Journal of Immunotherapy* 24(4):363-373, 2001.
Dujon et al., "Mobile introns: definition of terms and recommended nomenclature," *Gene* 82:115-118, 1989.
Dunbar et al., "ANARCI: antigen receptor numbering and receptor classification," *Bioinformatics* 32(2):298-300, 2016.
Engels et al., "Retroviral Vectors for High-Level Transgene Expression in T Lymphocytes," *Human Gene Therapy* 14:1155-1168, Aug. 10, 2003.
Epinat et al., "A novel engineered meganuclease induces homologous recombination in yeast and mammalian cells," *Nucleic Acids Research* 31(11):2952-2962, 2003.
Floros et al., "Anticancer Cytokines: Biology and Clinical Effects of IFN-α2, IL-2, IL-15, IL-21, and IL-12," *Semin Oncol.* 42(4):539-548, Aug. 2015 (HHS Public Access Author manuscript, available in PMC Aug. 1, 2016) (17pages).
Frasca et al., "BRAF(V600E) mutation and the biology of papillary thyroid cancer," Endocrine-Related Cancer 15:191-205, 2008.
Gao et al., "Molecular interactions of coreceptor CD8 and MHC class I: the molecular basis for functional coordination with the T-cell receptor," *Immunology Today* 21(12):630-636, Dec. 2000.
GenBank, "*Homo sapiens* B-Raf proto-oncogene, serine/threonine kinase (BRAF), mRNA," Accession No. NM_004333.4, Jul. 17, 2017. (6 pages).
Gimble et al., "Substrate Recognition and Induced DNA Distortion by the PI-Scel Endonuclease, an Enzyme Generated by Protein Splicing," *J. Mol. Biol.* 263:163-180, 1996.
Green et al., "Mitochondria and Apoptosis," *Science* 281: 1309-1312, Aug. 28, 1998.
Gros et al., "Prospective identification of neoantigen-specific lymphocytes in the peripheral blood of melanoma patients," *Nat Med.* 22(4):433-438, Apr. 2016 (HHS Public Access Author manuscript, available in PMC Aug. 25, 2020) (19 pages).
Hanahan et al., "Hallmarks of Cancer: The Next Generation," *Cell* 144:646-674, Mar. 4, 2011.
Hanahan et al., "The Hallmarks of Cancer," *Cell* 100:57-70, Jan. 7, 2000.
Harris et al., "Adoptive T Cell Therapies: A Comparison of T Cell Receptors and Chimeric Antigen Receptors," Trends in Pharmacological Sciences 37(3):220-230, Mar. 2016.
Ho et al., "In vitro methods for generating CD8+ T-cell clones for immunotherapy from the naïve repertoire," *Journal of Immunological Methods* 310:40-52, 2006.
Janeway et al., "Immunobiology: The Immune System in Health and Disease," 3rd Ed., Current Biology Publications, p. 4:33, 1997. (14 pages).
Jasin, "Genetic manipulation of genomes with rare-cutting endonucleases," *TIG* 12(6):224-228, Jun. 1996.
Jinek et al., "A Programmable Dual-RNA-Guided DNA Endonuclease in Adaptive Bacterial Immunity," *Science* 337:816-821, Aug. 17, 2012.
Johnson et al., "Gene therapy with human and mouse T-cell receptors mediates cancer regression and targets normal tissues expressing cognate antigen," *Blood* 114(3):535-546, Jul. 16, 2009. (13 pages).
Jones et al., "Lentiviral Vector Design for Optimal T Cell Receptor Gene Expression in the Transduction of Peripheral Blood Lymphocytes and Tumor-Infiltrating Lymphocytes," *Human Gene Therapy* 20:630-640, Jun. 2009.
Jores et al., "Resolution of hypervariable regions in T-cell receptor β chains by a modified Wu-Kabat index of amino acid diversity," *Proc. Natl. Acad. Sci. USA* 87:9138-9142, Dec. 1990.
Kabat et al., "Sequences of Proteins of Immunological Interest," Fifth Edition, U.S. Department of Health and Human Services, 1991. (84 pages).
Kim et al., "Analysis of the Paired TCR a-and B-chains of Single Human T Cells," *PLoS ONE* 7(5):e37338, May 2012. (12 pages).
Koboldt et al., "VarScan 2: Somatic mutation and copy No. alteration discovery in cancer by exome sequencing," *Genome Research* 22:568-576, 2012.

(56) References Cited

OTHER PUBLICATIONS

Kreiter et al., "Increased Antigen Presentation Efficiency by Coupling Antigens to MHC Class I Trafficking Signals," *The Journal of Immunology* 180:309-318, 2008 (12 pages).

Kuball et al., "Facilitating matched pairing and expression of TCR chains introduced into human T cells," *Blood* 109(6):2331-2338, Mar. 15, 2007.

Kyrgidis et al., "Melanoma: Stem cells, sun exposure and hallmarks for carcinogenesis, molecular concepts and future clinical implications," *Journal of Carcinogenesis* 9:3, Apr. 1, 2010. (29 pages).

Larsson et al., "Local co-administration of gene-silencing RNA and drugs in cancer therapy: State-of-the art and therapeutic potential," *Cancer Treatment Reviews* 55:128-135, 2017.

Leen et al., "Improving T Cell Therapy for Cancer," *Annu. Rev. Immunol.* 25:243-265, 2007.

Lefranc et al., "IMGT unique numbering for immunoglobulin and T cell receptor variable domains and Ig superfamily V-like domains," *Developmental and Comparative Immunology* 27:55-77, 2003.

Lehninger, Lehninger (eds.), Biochemistry, The Molecular Basis of Cell Structure and Function, Worth Publishers, Inc., New York, N.Y., 1975, pp. 45-52. (12 pages).

Li et al., "Fast and accurate short read alignment with Burrows-Wheeler transform," *Bioinformatics* 25(14):1754-1760, 2009.

Li et al., "RSEM: accurate transcript quantification from RNA-Seq data with or without a reference genome," *BMC Bioinformatics* 12:323, 2011. (16 pages).

Li, "Aligning sequence reads, clone sequences and assembly contigs with BWA-MEM," 2013. (3 pages).

Lim et al., "Hepatitis B virus nuclear export elements: RNA stem-loop α and β, key parts of the HBV post-transcriptional regulatory element," *RNA Biology* 13(9):743-747, 2016. (6 pages).

Liu et al., "Selective inhibition of IDO1 effectively regulates mediators of antitumor immunity," Blood 115(17):3520-3530, Apr. 29, 2010.

Manici et al., "Melanoma Cells Present a MAGE-3 Epitope to CD4+ Cytotoxic T Cells in Association with Histocompatibility Leukocyte Antigen DR11," *J. Exp. Med.* 189(5):871-876, Mar. 1, 1999.

Mautino et al., "NLG919, a novel indoleamine-2,3-dioxygenase (IDO)-pathway inhibitor drug candidate for cancer therapy," American Association for Cancer Research 104th Annual Meeting, Apr. 6-10, 2013 (Abstract only). (1 page).

Munson et al., "Identification of shared TCR sequences from T cells in human breast cancer using emulsion RT-PCR," *PNAS* 113(29):8272-8277, Jul. 19, 2016.

Penix et al., "Two Essential Regulatory Elements in the Human Interferon γ Promoter Confer Activation Specific Expression in T Cells," *The Journal of Experimental Medicine* 178:1483-1496, Nov. 1993.

Perler et al., "Protein splicing elements: inteins and exteins—a definition of terms and recommended nomenclature," *Nucleic Acids Research* 22(7): 1125-1127, 1994.

Petersdorf et al., "The International Histocompatibility Working Group in Hematopoietic Cell Transplantation," *Int J Immunogenet* 40(1):Feb. 2013 (NIH Public Access Author Manuscript, available in PMC Feb. 1, 2014) (15 pages).

Porteus et al., "Gene targeting using zinc finger nucleases," *Nature Biotechnology* 23(8):967-973, Aug. 2005.

Pâques et al., "Meganucleases and DNA Double-Strand Break-Induced Recombination: Perspectives for Gene Therapy," *Current Gene Therapy* 7:49-66, 2007.

Quezada et al., "Tumor-reactive CD4+ T cells develop cytotoxic activity and eradicate large established melanoma after transfer into lymphopenic hosts," *J. Exp. Med.* 207(3):637-650, Mar. 15, 2010.

Ramos et al., "Oncotator: cancer variant annotation tool," *Hum Mutat.* 36(4):E2423-E2429, Apr. 2015 (HHS Public Access Author manuscript, available in PMC Jul. 10, 2020) (9 pages).

Redmond et al., "Single-cell TCRseq: paired recovery of entire T-cell alpha and beta chain transcripts in T-cell receptors from single-cell RNAseq," *Genome Medicine* 8:80, 2016 (13 pages).

Ren et al., "Multiplex Genome Editing to Generate Universal CAR T Cells Resistant to PD1 Inhibition," *Clin Cancer Res* 23(9):2255-2266, May 1, 2017. (13 pages).

Riddell et al., "The use of anti-CD3 and anti-CD28 monoclonal antibodies to clone and expand human antigen-specific T cells," *Journal of Immunological Methods* 128:189-201, 1990.

Robins et al., "Comprehensive assessment of T-cell receptor B-chain diversity in αβ T cells," *Blood* 114(19):4099-4107, Nov. 5, 2009.

Robins et al., "Overlap and Effective Size of the Human CD8+ T Cell Receptor Repertoire," *Science Translational Medicine* 2(47):1-9, Sep. 1, 2010.

Robins et al., "Ultra-sensitive detection of rare T cell clones," *Journal of Immunological Methods* 375:14-19 (2012).

Sadelain et al., The Basic Principles of Chimeric Antigen Receptor Design, *Cancer Discovery* 3(4):388-398, 2013.

Sambrook et al., "Molecular Cloning: A Laboratory Manual," Second Edition, Cold Spring Harbor Laboratory Press, 1989. (3 pages).

Scatchard et al., "The Attractions of Proteins for Small Molecules And Ions," *Annals New York Academy of Sciences* 1:660-672, 1949.

Schmitt et al., "T Cell Receptor Gene Therapy for Cancer," *Human Gene Therapy* 20:1240-1248, 2009.

Scholten et al., "Codon modification of T cell receptors allows enhanced functional expression in transgenic human T cells," Clinical Immunology 119:135-145, 2006.

Shi et al., "Acquired Resistance and Clonal Evolution in Melanoma during BRAF Inhibitor Therapy," *Cancer Discov* 4(1):80-93, 2013.

Sommermeyer et al., "Chimeric antigen receptor-modified T cells derived from defined CD8+ and CD4+ subsets confer superior antitumor reactivity in vivo," *Leukemia* 30(2):492-500, Feb. 2016 (HHS Public Access Author manuscript, available in PMC May 18, 2016) (20 pages).

Stone et al., "A novel T cell receptor single-chain signaling complex mediates antigen- specific T cell activity and tumor control," *Cancer Immunol Immunother* 63:1163-1176, Aug. 1, 2014.

Stone et al., "Role of T cell receptor affinity in the efficacy and specificity of adoptive T cell therapies," *Frontiers in Immunology* 4(244):1-16, Aug. 2013.

Stromnes et al., "Re-adapting T cells for cancer therapy: from mouse models to clinical trials," *Immunological Reviews* 257:145-164, 2014.

Sun et al., "Defective CD8 T Cell Memory Following Acute Infection Without CD4 T Cell Help," *Science* 300(5617):339-342, Apr. 11, 2003 (NIH Public Access Author Manuscript, available in PMC Nov. 17, 2009) (7 pages).

Sussman et al., "Isolation and Characterization of New Homing Endonuclease Specificities at Individual Target Site Positions," *J. Mol. Biol.* 342:31-41, 2004.

Terentis et al., "The Selenazal Drug Ebselen Potently Inhibits Indoleamine 2,3-Dioxygenase by Targeting Enzyme Cysteine Residues," *Biochemistry* 49(3):591-600, 2010.

Thompson et al., "cis-Acting Sequences Required for Inducible Interleukin-2 Enhancer Function Bind a Novel Ets-Related Protein, Elf-1," *Molecular and Cellular Biology* 12(3):1043-1053, Mar. 1992.

Till et al., "Adoptive immunotherapy for indolent non-Hodgkin lymphoma and mantle cell lymphoma using genetically modified autologous CD20-specific T cells," Blood 112(6):2261-2271, Sep. 15, 2008.

Todd et al., "Transcription of the Interleukin 4 Gene Is Regulated by Multiple Promoter Elements," *J. Exp. Med.* 177:1663-1674, Jun. 1993.

Torikai et al., "A foundation for universal T-cell based immunotherapy: T cells engineered to express a CD19-specific chimeric-antigen-receptor and eliminate expression of endogenous TCR," Blood 119(24):5697-5705, Jun. 14, 2012.

Torikai et al., "Genetic editing of HLA expression in hematopoietic stem cells to broaden their human application," *Scientific Reports* 6:21757, Feb. 23, 2016.

Torikai et al., "Toward eliminating HLA class I expression to generate universal cells from allogeneic donors," Blood 122(8):1341-1349, Aug. 22, 2013.

(56) References Cited

OTHER PUBLICATIONS

Tran et al., "Cancer Immunotherapy Based on Mutation-Specific CD4+ T Cells in a Patient with Epithelial Cancer," *Science* 344(6184):641-645, May 9, 2014. (6 pages).

UniProt, "BRAF_Human," sequence ID No. P15056, downloaded Nov. 2, 2022. (24 pages).

UniProt, "CD4_Human," sequence ID No. P01730, downloaded Nov. 2, 2022. (16 pages).

UniProt, "CD8A_Human," sequence ID No. P01732, downloaded Nov. 2, 2022. (9 pages).

UniProt, "CD8B_Human," sequence ID No. P10966, downloaded Nov. 2, 2022. (7 pages).

Van der Auwera et al., "From FastQ data to high confidence variant calls: the Genome Analysis Toolkit best practices pipeline," *Curr Protoc Bioinformatics* 11(1110):11.10.1-11.10.33 (NIH Public Access Author Manuscript, available in PMC Nov. 25, 2014) (43 pages).

Wang et al., "Optimizing Adoptive Polyclonal T Cell Immunotherapy of Lymphomas, Using a Chimeric T Cell Receptor Possessing CD28 and CD137 Costimulatory Domains," Human Gene Therapy 18:712-725, Aug. 2007.

Warren et al., "Exhaustive T-cell repertoire sequencing of human peripheral blood samples reveals signatures of antigen selection and a directly measured repertoire size of at least 1 million clonotypes," *Genome Research* 21:790-797 2011.

Williams et al., "Interleukin-2 signals during priming are required for secondary expansion of CD8+ memory T cells," *Nature* 441(7095):890-893, Jun. 15, 2006 (NIH Public Access Author Manuscript, available in PMC Nov. 11, 2009) (12 pages).

Wilson, "Analyzing Biomolecular Interactions," *Science* 295:2103, 2105, Mar. 15, 2002. (3 pages).

Wolfe et al., "Analysis of Zinc Fingers Optimized via Phage Display: Evaluating the Utility of a Recognition Code," J. Mol. Biol. 285:1917-1934 (1999).

Wolff et al., "Monoclonal Antibody Homodimers: Enhanced Antitumor Activity in Nude Mice," Cancer Research 53:2560-2565, Jun. 1, 1993.

Xie et al., "sgRNAcas9: A Software Package for Designing CRISPR sgRNA and Evaluating Potential Off-Target Cleavage Sites," *PLoS ONE* 9(6):e100448, Jun. 23, 2014. (9 pages).

Yee et al., "Adoptive T cell therapy using antigen-specific CD8+ T cell clones for the treatment of patients with metastatic melanoma: In vivo persistence, migration, and antitumor effect of transferred T cells," *PNAS* 99(25):16168-16173, Dec. 10, 2002.

Henkart et al., "Chapter 36: Cytotoxic T-Lymphocytes," Fundamental Immunology, Lippincott Williams & Wilkins, Philadelphia, PA, 2003, pp. 1127-1150.

Coffin, "Chapter 58: Retroviridae: The viruses and their replication," Fundamental Virology, Third Edition, edited by Fields et al., Lippincott-Raven Publishers, Philadelphia, 1996, 1767-1847.

SEQUENCE LISTING

```
<160> NUMBER OF SEQ ID NOS: 149

<210> SEQ ID NO 1
<211> LENGTH: 137
<212> TYPE: PRT
<213> ORGANISM: Artificial Sequence
<220> FEATURE:
<223> OTHER INFORMATION: Synthetic sequence TCR1 alpha chain variable
      domain

<400> SEQUENCE: 1

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Arg Gly Asn Asn Asp Met Arg Phe Gly Ala Gly Thr Arg Leu Thr Val
        115                 120                 125
```

```
Lys Pro Asn Ile Gln Asn Pro Asp Pro
    130                 135

<210> SEQ ID NO 2
<211> LENGTH: 135
<212> TYPE: PRT
<213> ORGANISM: Artificial Sequence
<220> FEATURE:
<223> OTHER INFORMATION: Synthetic sequence TCR2-1 alpha chain variable
      domain

<400> SEQUENCE: 2

Met Arg Leu Val Ala Arg Val Thr Val Phe Leu Thr Phe Gly Thr Ile
1               5                  10                  15

Ile Asp Ala Lys Thr Thr Gln Pro Thr Ser Met Asp Cys Ala Glu Gly
                20                  25                  30

Arg Ala Ala Asn Leu Pro Cys Asn His Ser Thr Ile Ser Gly Asn Glu
            35                  40                  45

Tyr Val Tyr Trp Tyr Arg Gln Ile His Ser Gln Gly Pro Gln Tyr Ile
        50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Ala Tyr Ser Gly
            100                 105                 110

Tyr Ser Thr Leu Thr Phe Gly Lys Gly Thr Met Leu Leu Val Ser Pro
        115                 120                 125

Asp Ile Gln Asn Pro Asp Pro
    130                 135

<210> SEQ ID NO 3
<211> LENGTH: 142
<212> TYPE: PRT
<213> ORGANISM: Artificial Sequence
<220> FEATURE:
<223> OTHER INFORMATION: Synthetic sequence TCR2-2 alpha chain variable
      domain

<400> SEQUENCE: 3

Met Lys Ser Leu Arg Val Leu Leu Val Ile Leu Trp Leu Gln Leu Ser
1               5                  10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Ile Thr Leu Asn Asn Asn Ala Gly Asn Met Leu Thr Phe Gly Gly Gly
        115                 120                 125

Thr Arg Leu Met Val Lys Pro His Ile Gln Asn Pro Asp Pro
    130                 135                 140
```

<210> SEQ ID NO 4
<211> LENGTH: 138
<212> TYPE: PRT
<213> ORGANISM: Artificial Sequence
<220> FEATURE:
<223> OTHER INFORMATION: Synthetic sequence TCR3 alpha chain variable
      domain

<400> SEQUENCE: 4

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Thr Ser Asn Ala Gly Lys Ser Thr Phe Gly Asp Gly Thr Thr Leu Thr
        115                 120                 125

Val Lys Pro Asn Ile Gln Asn Pro Asp Pro
    130                 135

<210> SEQ ID NO 5
<211> LENGTH: 132
<212> TYPE: PRT
<213> ORGANISM: Artificial Sequence
<220> FEATURE:
<223> OTHER INFORMATION: Synthetic sequence TCR1 beta chain variable
      domain

<400> SEQUENCE: 5

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Asn Glu Gly Asn Ser Gly Asn Thr Ile Tyr Phe Gly Glu Gly Ser Trp
        115                 120                 125

Leu Thr Val Val
    130

<210> SEQ ID NO 6

<211> LENGTH: 130
<212> TYPE: PRT
<213> ORGANISM: Artificial Sequence
<220> FEATURE:
<223> OTHER INFORMATION: Synthetic sequence TCR2 beta chain variable domain

<400> SEQUENCE: 6

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Gly Ala Arg Gln Ile Pro Tyr Thr Phe Gly Ser Gly Thr Arg Leu Thr
        115                 120                 125

Val Val
    130

<210> SEQ ID NO 7
<211> LENGTH: 140
<212> TYPE: PRT
<213> ORGANISM: Artificial Sequence
<220> FEATURE:
<223> OTHER INFORMATION: Synthetic sequence TCR3 beta chain variable domain

<400> SEQUENCE: 7

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Ser Ala Ala Gly Gly Gly Tyr Gly Tyr Thr Phe Asn Tyr Gly
        115                 120                 125

Tyr Thr Phe Gly Ser Gly Thr Arg Leu Thr Val Val
    130                 135                 140

<210> SEQ ID NO 8
<211> LENGTH: 287
<212> TYPE: DNA
<213> ORGANISM: Artificial Sequence

```
<220> FEATURE:
<223> OTHER INFORMATION: Synthetic sequence TCRBV28-01

<400> SEQUENCE: 8
gatgtgaaag taacccagag ctcgagatat ctagtcaaaa ggacgggaga gaaagttttt      60
ctggaatgtg tccaggatat ggaccatgaa aatatgttct ggtatcgaca agacccagt      120 ctggggctac ggctgatcta tttctcatat gatgttaaaa tgaaagaaaa aggagatatt    180
cctgaggggt acagtgtctc tagagagaag aaggagcgct ctccctgat tctggagtcc    240 gccagcacca accagacatc tatgtacctc tgtgccagca gtttatg                   287

<210> SEQ ID NO 9
<211> LENGTH: 50
<212> TYPE: DNA
<213> ORGANISM: Artificial Sequence
<220> FEATURE:
<223> OTHER INFORMATION: Synthetic sequence TCRBJ01-03

<400> SEQUENCE: 9
ctctggaaac accatatatt ttggagaggg aagttggctc actgttgtag                 50

<210> SEQ ID NO 10
<211> LENGTH: 48
<212> TYPE: DNA
<213> ORGANISM: Artificial Sequence
<220> FEATURE:
<223> OTHER INFORMATION: Synthetic sequence TCRBJ01-02

<400> SEQUENCE: 10
ctaactatgg ctacaccttc ggttcgggga ccaggttaac cgttgtag                   48

<210> SEQ ID NO 11
<211> LENGTH: 279
<212> TYPE: DNA
<213> ORGANISM: Artificial Sequence
<220> FEATURE:
<223> OTHER INFORMATION: Synthetic sequence TCRAV21-01

<400> SEQUENCE: 11
aaacaggagg tgacgcagat tcctgcagct ctgagtgtcc cagaaggaga aaacttggtt     60
ctcaactgca gtttcactga tagcgctatt tacaacctcc agtggtttag gcaggaccct    120
gggaaaggtc tcacatctct gttgcttatt cagtcaagtc agagagagca acaagtgga     180 agacttaatg cctcgctgga taaatcatca ggacgtagta ctttatacat tgcagcttct    240
cagcctggtg actcagccac ctacctctgt gctgtgagg                            279

<210> SEQ ID NO 12
<211> LENGTH: 277
<212> TYPE: DNA
<213> ORGANISM: Artificial Sequence
<220> FEATURE:
<223> OTHER INFORMATION: Synthetic sequence TCRAV26-01

<400> SEQUENCE: 12
gatgctaaga ccacccagcc cccctccatg gattgcgctg aaggaagagc tgcaaacctg     60
ccttgtaatc actctaccat cagtggaaat gagtatgtgt attggtatcg acagattcac    120
tcccaggggc acagtatat cattcatggt ctaaaaaaca atgaaaccaa tgaaatggcc     180
tctctgatca tcacagaaga cagaaagtcc agcaccttga tcctgccca cgctacgctg    240 agagacactg ctgtgtacta ttgcatcgtc agagtcg                              277
```

<210> SEQ ID NO 13
<211> LENGTH: 277
<212> TYPE: DNA
<213> ORGANISM: Artificial Sequence
<220> FEATURE:
<223> OTHER INFORMATION: Synthetic sequence TCRAV12-02

<400> SEQUENCE: 13

```
cagaaggagg tggagcagaa ttctggaccc ctcagtgttc cagagggagc cattgcctct      60
ctcaactgca cttacagtga ccgaggttcc cagtccttct tctggtacag acaatattct     120
gggaaaagcc ctgagttgat aatgttcata tactccaatg gtgacaaaga agatggaagg     180
tttacagcac agctcaataa agccagccag tatgtttctc tgctcatcag agactcccag     240
cccagtgatt cagccaccta cctctgtgcc gtgaaca                              277
```

<210> SEQ ID NO 14
<211> LENGTH: 54
<212> TYPE: DNA
<213> ORGANISM: Artificial Sequence
<220> FEATURE:
<223> OTHER INFORMATION: Synthetic sequence TCRAJ43-01

<400> SEQUENCE: 14

```
acaataacaa tgacatgcgc tttggagcag ggaccagact gacagtaaaa ccaa            54
```

<210> SEQ ID NO 15
<211> LENGTH: 60
<212> TYPE: DNA
<213> ORGANISM: Artificial Sequence
<220> FEATURE:
<223> OTHER INFORMATION: Synthetic sequence TCRAJ11-01

<400> SEQUENCE: 15

```
tgaattcagg atacagcacc ctcacctttg gaaggggac tatgcttcta gtctctccag       60
```

<210> SEQ ID NO 16
<211> LENGTH: 63
<212> TYPE: DNA
<213> ORGANISM: Artificial Sequence
<220> FEATURE:
<223> OTHER INFORMATION: Synthetic sequence TCRAJ39-01

<400> SEQUENCE: 16

```
tgaataataa tgcaggcaac atgctcacct ttggaggggg aacaaggtta atggtcaaac      60
ccc                                                                    63
```

<210> SEQ ID NO 17
<211> LENGTH: 59
<212> TYPE: DNA
<213> ORGANISM: Artificial Sequence
<220> FEATURE:
<223> OTHER INFORMATION: Synthetic sequence TCRAJ27-01

<400> SEQUENCE: 17

```
taacaccaat gcaggcaaat caacctttgg ggatgggact acgctcactg tgaagccaa       59
```

<210> SEQ ID NO 18
<211> LENGTH: 409
<212> TYPE: DNA
<213> ORGANISM: Artificial Sequence
<220> FEATURE:
<223> OTHER INFORMATION: Synthetic sequence TCR1 alpha chain variable
      domain

<400> SEQUENCE: 18

```
atggaaacac tgctgggcct gctgatcctg tggctgcaac tgcaatgggt gtccagcaag      60
caagaagtga ctcagatccc tgccgctctg tctgtgcctg agggcgaaaa cctggtcctg     120
aactgcagct tcaccgacag cgccatctac aacctgcagt ggttcaggca ggatccaggc     180
aagggcctga catccctgct gctgattcag agcagccaga gagagcagac cagcggcaga     240
ctgaatgcca gcctggataa gtcctccggc agaagcaccc tgtatatcgc cgcttctcag     300
ccaggcgata gcgccacata tctgtgtgcc gttcggagag caacaacga catgagattc     360 ggagccggca ccagactgac cgtgaagccc aacattcaga accccgatc                409
```

<210> SEQ ID NO 19
<211> LENGTH: 403
<212> TYPE: DNA
<213> ORGANISM: Artificial Sequence
<220> FEATURE:
<223> OTHER INFORMATION: Synthetic sequence TCR2-1 alpha chain variable
domain

<400> SEQUENCE: 19

```
atgagactgg tggccagagt gacagtgttc ctgaccttcg gcaccatcat cgacgccaag      60
accacacagc ccaccagcat ggattgtgcc gagggcagag ctgccaacct gccttgtaat     120
cacagcacca tcagcggcaa cgagtacgtg tactggtaca ggcagatcca ctctcagggc     180
cctcagtaca tcatccacgg cctgaagaac aacgagacaa cgagatggc ctctctgatc     240 atcaccgagg accgcaagag cagccaccctg attctgcctc acgccacact gagagacacc     300
gccgtgtact actgtatcgt gcgggcctac agcggctaca gcacactgac atttggcaag     360
ggcaccatgc tgctcgtgtc cccagacatt cagaaccccg atc                       403
```

<210> SEQ ID NO 20
<211> LENGTH: 424
<212> TYPE: DNA
<213> ORGANISM: Artificial Sequence
<220> FEATURE:
<223> OTHER INFORMATION: Synthetic sequence TCR2-2 alpha chain variable
domain

<400> SEQUENCE: 20

```
atgaagtccc tgagagtgct gctggtcatc ctgtggctgc agctgtcttg ggtctggtcc      60
cagcagaaag aggtggaaca gaacagcggc cctctgtctg ttcctgaagg cgctatcgcc     120
tctctgaatt gcacctacag cgacagaggc agccagagct cttctggta tcggcagtac     180 agcggcaaga gccccgagct gatcatgttc atctacagca acggcgacaa agaggacggc     240
cggtttacag cccagctgaa caaggccagc cagtacgtgt cactgctgat cagagacagc     300
cagcctagcg acagcgccac ctatctgtgt gccgtgatca ccctgaacaa caacgccggc     360
aacatgctga cctttggcgg cggaacacgg ctgatggtta agcccacat tcagaacccc     420 gatc                                                                   424
```

<210> SEQ ID NO 21
<211> LENGTH: 412
<212> TYPE: DNA
<213> ORGANISM: Artificial Sequence
<220> FEATURE:
<223> OTHER INFORMATION: Synthetic sequence TCR3 alpha chain variable
domain

<400> SEQUENCE: 21

| | |
|---|---|
| atgaagtccc tgagagtgct gctggtcatc ctgtggctgc agctgtcttg ggtctggtcc | 60 |
| cagcagaaag aggtggaaca gaacagcggc cctctgtccg ttcctgaagg cgccattgct | 120 |
| agcctgaatt gcacctacag cgaccggggc agccagagct tcttctggta taggcagtac | 180 |
| agcggcaaga gccccgagct gatcatgttc atctacagca acggcgacaa agaggacggc | 240 |
| cggtttacag cccagctgaa caaggccagc cagtacgtgt cactgctgat cagagacagc | 300 |
| cagcctagcg acagcgccac ctatctgtgt gccgtgacaa gcaatgccgg caagtccaca | 360 |
| tttggcgacg gcacaaccct gaccgtgaag cccaacattc agaaccccga tc | 412 |

```
<210> SEQ ID NO 22
<211> LENGTH: 396
<212> TYPE: DNA
<213> ORGANISM: Artificial Sequence
<220> FEATURE:
<223> OTHER INFORMATION: Synthetic sequence TCR1 beta chain variable
      domain

<400> SEQUENCE: 22
```

| | |
|---|---|
| atgggaatta gactgctgtg cagagtggcc ttctgcttcc tggctgttgg cctggtggac | 60 |
| gtgaaagtga cccagagcag cagatacctg gtcaagagaa ccggcgagaa ggtgttcctg | 120 |
| gaatgcgtgc aggacatgga ccacgagaat atgttctggt acagacagga ccccggcctg | 180 |
| ggcctgagac tgatctactt cagctacgac gtgaagatga ggaaaagggg cgacatcccc | 240 |
| gagggctaca gcgtgtccag agagaagaaa gagcggttca gcctgatcct ggaaagcgcc | 300 |
| agcaccaacc agaccagcat gtacctgtgc gccagcaacg agggcaatag cggcaacacc | 360 |
| atctacttcg gcgaaggcag ctggctgacc gtggtg | 396 |

```
<210> SEQ ID NO 23
<211> LENGTH: 390
<212> TYPE: DNA
<213> ORGANISM: Artificial Sequence
<220> FEATURE:
<223> OTHER INFORMATION: Synthetic sequence TCR2 beta chain variable
      domain

<400> SEQUENCE: 23
```

| | |
|---|---|
| atgggaatta gactgctgtg cagagtggcc ttctgcttcc tggctgttgg cctggtggac | 60 |
| gtgaaagtga cccagagcag cagatacctg gtcaagagaa ccggcgagaa ggtgttcctg | 120 |
| gaatgcgtgc aggacatgga ccacgagaat atgttctggt acagacagga ccccggcctg | 180 |
| ggcctgagac tgatctactt cagctacgac gtgaagatga ggaaaagggg cgacatcccc | 240 |
| gagggctaca gcgtgtccag agagaagaaa gagcggttca gcctgatcct ggaaagcgcc | 300 |
| agcaccaacc agaccagcat gtacctgtgt gccagcggcg ccagacagat cccttacaca | 360 |
| tttggctccg gcaccagact gaccgtggtg | 390 |

```
<210> SEQ ID NO 24
<211> LENGTH: 420
<212> TYPE: DNA
<213> ORGANISM: Artificial Sequence
<220> FEATURE:
<223> OTHER INFORMATION: Synthetic sequence TCR3 beta chain variable
      domain

<400> SEQUENCE: 24
```

| | |
|---|---|
| atgggaatta gactgctgtg cagagtggcc ttctgcttcc tggctgttgg cctggtggac | 60 |
| gtgaaagtga cccagagcag cagatacctg gtcaagagaa ccggcgagaa ggtgttcctg | 120 |

```
gaatgcgtgc aggacatgga ccacgagaat atgttctggt acagacagga ccccggcctg    180
ggcctgagac tgatctactt cagctacgac gtgaagatga aggaaaaggg cgacatcccc    240
gagggctaca gcgtgtccag agagaagaaa gagcggttca gcctgatcct ggaaagcgcc    300
agcaccaacc agaccagcat gtacctgtgt gccagctctc tgtctgctgc cggcggaggc    360
tatggctaca ccttcaatta cggctacaca ttcggcagcg gcaccagact gaccgtggtg    420
```

<210> SEQ ID NO 25
<211> LENGTH: 134
<212> TYPE: PRT
<213> ORGANISM: Artificial Sequence
<220> FEATURE:
<223> OTHER INFORMATION: Synthetic sequence TCR alpha chain constant
      domain

<400> SEQUENCE: 25

```
Ala Val Tyr Gln Leu Arg Asp Ser Lys Ser Ser Asp Lys Ser Val Cys
1               5                   10                  15

Leu Phe Thr Asp Phe Asp Ser Gln Thr Asn Val Ser Gln Ser Lys Asp
            20                  25                  30

Ser Asp Val Tyr Ile Thr Asp Lys Cys Val Leu Asp Met Arg Ser Met
        35                  40                  45

Asp Phe Lys Ser Asn Ser Ala Val Ala Trp Ser Asn Lys Ser Asp Phe
    50                  55                  60

Ala Cys Ala Asn Ala Phe Asn Asn Ser Ile Ile Pro Glu Asp Thr Phe
65                  70                  75                  80

Phe Pro Ser Pro Glu Ser Ser Cys Asp Val Lys Leu Val Glu Lys Ser
                85                  90                  95

Phe Glu Thr Asp Thr Asn Leu Asn Phe Gln Asn Leu Ser Val Ile Gly
            100                 105                 110

Phe Arg Ile Leu Leu Leu Lys Val Ala Gly Phe Asn Leu Leu Met Thr
        115                 120                 125

Leu Arg Leu Trp Ser Ser
    130
```

<210> SEQ ID NO 26
<211> LENGTH: 177
<212> TYPE: PRT
<213> ORGANISM: Artificial Sequence
<220> FEATURE:
<223> OTHER INFORMATION: Synthetic sequence TCR beta chain constant
      domain

<400> SEQUENCE: 26

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110
```

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 27
<211> LENGTH: 407
<212> TYPE: DNA
<213> ORGANISM: Artificial Sequence
<220> FEATURE:
<223> OTHER INFORMATION: Synthetic sequence TCR alpha chain constant
      domain

<400> SEQUENCE: 27
ctgcagtgta ccagctgcgg gacagcaaga gcagcgacaa gagcgtgtgc ctgttcaccg     60
acttcgacag ccagaccaac gtgtcccaga gcaaggacag cgacgtgtac atcaccgata    120
agtgcgtgct ggacatgcgg agcatggact tcaagagcaa cagcgccgtg gcctggtcca    180
acaagagcga cttcgcctgc gccaacgcct tcaacaacag cattatcccc gaggacacat    240
tcttcccaag ccccgagagc agctgcgacg tgaagctggt ggaaaagagc ttcgagacag    300
acaccaacct gaacttccag aacctcagcg tgatcggctt ccggatcctg ctgctgaagg    360
tggccggctt caacctgctg atgaccctgc ggctgtggtc cagctga                  407

<210> SEQ ID NO 28
<211> LENGTH: 454
<212> TYPE: DNA
<213> ORGANISM: Artificial Sequence
<220> FEATURE:
<223> OTHER INFORMATION: Synthetic sequence TCR beta chain constant
      domain

<400> SEQUENCE: 28
gaagatctga acaaagtgtt ccctccagag gtggccgtgt tcgagccttc tgaggccgag     60
atcagccaca cacagaaagc cacactcgtg tgcctggcca ccggcttttt tcccgatcac    120
gtggaactgt cttggtgggt caacggcaaa gaggtgcaca gcggcgtctg taccgatcct    180
cagcctctga agagcagcc cgctctgaac gactccagat actgcctgag cagcaggctg    240
agagtgtccg ccaccttctg gcagaacccc agaaaccact tcagatgcca ggtgcagttc    300
tacggcctga gcgagaacga tgagtggacc caggatagag ccaagcctgt gacacagatc    360
gtgtctgccg aagcctgggg cagagccgat gtggctttta cctccgtgtc ctatcagcag    420
ggcgtgctgt ctgccaccat cctgtatgag atcc                                454

<210> SEQ ID NO 29
<211> LENGTH: 12
<212> TYPE: PRT
<213> ORGANISM: Artificial Sequence
<220> FEATURE:
<223> OTHER INFORMATION: Synthetic sequence TCR1 alpha chain CDR3

<400> SEQUENCE: 29

Cys Ala Val Arg Arg Gly Asn Asn Asp Met Arg Phe
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic sequence TCR2-1 alpha chain CDR3

<400> SEQUENCE: 30

Cys Ile Val Arg Ala Tyr Ser Gly Tyr Ser Thr Leu Thr Phe
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Synthetic sequence TCR2-2 alpha chain CDR3

<400> SEQUENCE: 31

Cys Ala Val Ile Thr Leu Asn Asn Asn Ala Gly Asn Met Leu Thr Phe
1               5                   10                  15

<210> SEQ ID NO 32
<211> LENGTH: 12
<212> TYPE: PRT
<213> ORGANISM: Artificial Sequence
<220> FEATURE:
<223> OTHER INFORMATION: Synthetic sequence TCR3 alpha chain CDR3

<400> SEQUENCE: 32

Cys Ala Val Thr Ser Asn Ala Gly Lys Ser Thr Phe
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic sequence TCR1 beta chain CDR3

<400> SEQUENCE: 33

Cys Ala Ser Asn Glu Gly Asn Ser Gly Asn Thr Ile Tyr Phe
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic sequence TCR2-1 beta chain CDR3

<400> SEQUENCE: 34

Cys Ala Ser Gly Ala Arg Gln Ile Pro Tyr Thr Phe
1               5                   10

<210> SEQ ID NO 35
<211> LENGTH: 16
<212> TYPE: PRT
<213> ORGANISM: Artificial Sequence
<220> FEATURE:
<223> OTHER INFORMATION: Synthetic sequence TCR3 beta chain CDR3

<400> SEQUENCE: 35

Cys Ala Ser Ser Leu Ser Ala Ala Gly Gly Tyr Gly Tyr Thr Phe
1               5                   10                  15

<210> SEQ ID NO 36
<211> LENGTH: 766
<212> TYPE: PRT
<213> ORGANISM: Artificial Sequence
<220> FEATURE:
<223> OTHER INFORMATION: Synthetic sequence Human BRAF

<400> SEQUENCE: 36

```
Met Ala Ala Leu Ser Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ala Pro Asn
        355                 360                 365
```

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
            435                 440                 445

Asp Trp Glu Ile Pro Asp Gly Gln Ile Thr Val Gly Gln Arg Ile Gly
450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 37
<211> LENGTH: 27
<212> TYPE: PRT

<213> ORGANISM: Artificial Sequence
<220> FEATURE:
<223> OTHER INFORMATION: Synthetic sequence 27-mer BRAFV600E peptide

<400> SEQUENCE: 37

Asp Leu Thr Val Lys Ile Gly Asp Phe Gly Leu Ala Thr Glu Lys Ser
1               5                   10                  15

Arg Trp Ser Gly Ser His Gln Phe Glu Gln Leu
            20                  25

<210> SEQ ID NO 38
<211> LENGTH: 20
<212> TYPE: PRT
<213> ORGANISM: Artificial Sequence
<220> FEATURE:
<223> OTHER INFORMATION: Synthetic sequence 20-mer BRAFV600E peptide

<400> SEQUENCE: 38

Asp Leu Thr Val Lys Ile Gly Asp Phe Gly Leu Ala Thr Glu Lys Ser
1               5                   10                  15

Arg Trp Ser Gly
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic sequence 20-mer BRAFV600E peptide

<400> SEQUENCE: 39

Asp Phe Gly Leu Ala Thr Glu Lys Ser Arg Trp Ser Gly Ser His Gln
1               5                   10                  15

Phe Glu Gln Leu
            20

<210> SEQ ID NO 40
<211> LENGTH: 266
<212> TYPE: PRT
<213> ORGANISM: Artificial Sequence
<220> FEATURE:
<223> OTHER INFORMATION: Synthetic sequence HLADRB1

<400> SEQUENCE: 40

Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ala Gly Asp Thr
            20                  25                  30

Arg Pro Arg Phe Leu Trp Gln Leu Lys Phe Glu Cys His Phe Phe Asn
        35                  40                  45

Gly Thr Glu Arg Val Arg Leu Leu Glu Arg Cys Ile Tyr Asn Gln Glu
    50                  55                  60

Glu Ser Val Arg Phe Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Gln Arg Arg Ala Ala Val Asp Thr Tyr Cys Arg His Asn Tyr
            100                 105                 110

Gly Val Gly Glu Ser Phe Thr Val Gln Arg Arg Val Glu Pro Lys Val
        115                 120                 125

Thr Val Tyr Pro Ser Lys Thr Gln Pro Leu Gln His His Asn Leu Leu

```
            130                 135                 140
Val Cys Ser Val Ser Gly Phe Tyr Pro Gly Ser Ile Glu Val Arg Trp
145                 150                 155                 160

Phe Arg Asn Gly Gln Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
            260                 265

<210> SEQ ID NO 41
<211> LENGTH: 261
<212> TYPE: PRT
<213> ORGANISM: Artificial Sequence
<220> FEATURE:
<223> OTHER INFORMATION: Synthetic sequence HLADQB10302

<400> SEQUENCE: 41

Met Ser Trp Lys Lys Ala Leu Arg Ile Pro Gly Gly Leu Arg Val Ala
1               5                   10                  15

Thr Val Thr Leu Met Leu Ala Met Leu Ser Thr Pro Val Ala Glu Gly
                20                  25                  30

Arg Asp Ser Pro Glu Asp Phe Val Tyr Gln Phe Lys Gly Met Cys Tyr
            35                  40                  45

Phe Thr Asn Gly Thr Glu Arg Val Arg Leu Val Thr Arg Tyr Ile Tyr
    50                  55                  60

Asn Arg Glu Glu Tyr Ala Arg Phe Asp Ser Asp Val Gly Val Tyr Arg
65                  70                  75                  80

Ala Val Thr Pro Leu Gly Pro Pro Ala Ala Glu Tyr Trp Asn Ser Gln
                85                  90                  95

Lys Glu Val Leu Glu Arg Thr Arg Ala Glu Leu Asp Thr Val Cys Arg
            100                 105                 110

His Asn Tyr Gln Leu Glu Leu Arg Thr Thr Leu Gln Arg Arg Val Glu
        115                 120                 125

Pro Thr Val Thr Ile Ser Pro Ser Arg Thr Glu Ala Leu Asn His His
    130                 135                 140

Asn Leu Leu Val Cys Ser Val Thr Asp Phe Tyr Pro Ala Gln Ile Lys
145                 150                 155                 160

Val Arg Trp Phe Arg Asn Asp Gln Glu Glu Thr Thr Gly Val Val Ser
                165                 170                 175

Thr Pro Leu Ile Arg Asn Gly Asp Trp Thr Phe Gln Ile Leu Val Met
            180                 185                 190

Leu Glu Met Thr Pro Gln Arg Gly Asp Val Tyr Thr Cys His Val Glu
        195                 200                 205

His Pro Ser Leu Gln Asn Pro Ile Ile Val Glu Trp Arg Ala Gln Ser
    210                 215                 220

Glu Ser Ala Gln Ser Lys Met Leu Ser Gly Ile Gly Gly Phe Val Leu
```

```
                225                 230                 235                 240
Gly Leu Ile Phe Leu Gly Leu Gly Leu Ile Ile His His Arg Ser Gln
                    245                 250                 255

Lys Gly Leu Leu His
            260

<210> SEQ ID NO 42
<211> LENGTH: 255
<212> TYPE: PRT
<213> ORGANISM: Artificial Sequence
<220> FEATURE:
<223> OTHER INFORMATION: Synthetic sequence HLADQA103

<400> SEQUENCE: 42

Met Ile Leu Asn Lys Ala Leu Met Leu Gly Ala Leu Ala Leu Thr Thr
1               5                   10                  15

Val Met Ser Pro Cys Gly Gly Glu Asp Ile Val Ala Asp His Val Ala
            20                  25                  30

Ser Tyr Gly Val Asn Leu Tyr Gln Ser Tyr Gly Pro Ser Gly Gln Tyr
        35                  40                  45

Ser His Glu Phe Asp Gly Asp Glu Glu Phe Tyr Val Asp Leu Glu Arg
    50                  55                  60

Lys Glu Thr Val Trp Gln Leu Pro Leu Phe Arg Arg Phe Arg Arg Phe
65                  70                  75                  80

Asp Pro Gln Phe Ala Leu Thr Asn Ile Ala Val Leu Lys His Asn Leu
                85                  90                  95

Asn Ile Val Ile Lys Arg Ser Asn Ser Thr Ala Ala Thr Asn Glu Val
            100                 105                 110

Pro Glu Val Thr Val Phe Ser Lys Ser Pro Val Thr Leu Gly Gln Pro
        115                 120                 125

Asn Thr Leu Ile Cys Leu Val Asp Asn Ile Phe Pro Pro Val Val Asn
    130                 135                 140

Ile Thr Trp Leu Ser Asn Gly His Ser Val Thr Glu Gly Val Ser Glu
145                 150                 155                 160

Thr Ser Phe Leu Ser Lys Ser Asp His Ser Phe Phe Lys Ile Ser Tyr
                165                 170                 175

Leu Thr Phe Leu Pro Ser Ala Asp Glu Ile Tyr Asp Cys Lys Val Glu
            180                 185                 190

His Trp Gly Leu Asp Glu Pro Leu Leu Lys His Trp Glu Pro Glu Ile
        195                 200                 205

Pro Thr Pro Met Ser Glu Leu Thr Glu Thr Val Val Cys Ala Leu Gly
    210                 215                 220

Leu Ser Val Gly Leu Val Gly Ile Val Val Gly Thr Val Leu Ile Ile
225                 230                 235                 240

Arg Gly Leu Arg Ser Val Gly Ala Ser Arg His Gln Gly Pro Leu
                245                 250                 255

<210> SEQ ID NO 43
<211> LENGTH: 538
<212> TYPE: PRT
<213> ORGANISM: Artificial Sequence
<220> FEATURE:
<223> OTHER INFORMATION: Synthetic sequence HLADQB10302-P2A-HLADQBA103

<400> SEQUENCE: 43

Met Ser Trp Lys Lys Ala Leu Arg Ile Pro Gly Gly Leu Arg Val Ala
1               5                   10                  15
```

-continued

```
Thr Val Thr Leu Met Leu Ala Met Leu Ser Thr Pro Val Ala Glu Gly
         20                  25                  30

Arg Asp Ser Pro Glu Asp Phe Val Tyr Gln Phe Lys Gly Met Cys Tyr
         35                  40                  45

Phe Thr Asn Gly Thr Glu Arg Val Arg Leu Val Thr Arg Tyr Ile Tyr
         50                  55                  60

Asn Arg Glu Glu Tyr Ala Arg Phe Asp Ser Asp Val Gly Val Tyr Arg
 65                  70                  75                  80

Ala Val Thr Pro Leu Gly Pro Pro Ala Ala Glu Tyr Trp Asn Ser Gln
                 85                  90                  95

Lys Glu Val Leu Glu Arg Thr Arg Ala Glu Leu Asp Thr Val Cys Arg
                100                 105                 110

His Asn Tyr Gln Leu Glu Leu Arg Thr Thr Leu Gln Arg Arg Val Glu
                115                 120                 125

Pro Thr Val Thr Ile Ser Pro Ser Arg Thr Glu Ala Leu Asn His His
        130                 135                 140

Asn Leu Leu Val Cys Ser Val Thr Asp Phe Tyr Pro Ala Gln Ile Lys
145                 150                 155                 160

Val Arg Trp Phe Arg Asn Asp Gln Glu Glu Thr Thr Gly Val Val Ser
                165                 170                 175

Thr Pro Leu Ile Arg Asn Gly Asp Trp Thr Phe Gln Ile Leu Val Met
        180                 185                 190

Leu Glu Met Thr Pro Gln Arg Gly Asp Val Tyr Thr Cys His Val Glu
        195                 200                 205

His Pro Ser Leu Gln Asn Pro Ile Ile Val Glu Trp Arg Ala Gln Ser
210                 215                 220

Glu Ser Ala Gln Ser Lys Met Leu Ser Gly Ile Gly Gly Phe Val Leu
225                 230                 235                 240

Gly Leu Ile Phe Leu Gly Leu Gly Leu Ile Ile His His Arg Ser Gln
                245                 250                 255

Lys Gly Leu Leu His Gly Ser Gly Ala Thr Asn Phe Ser Leu Leu Lys
                260                 265                 270

Gln Ala Gly Asp Val Glu Glu Asn Pro Gly Pro Met Ile Leu Asn Lys
        275                 280                 285

Ala Leu Met Leu Gly Ala Leu Ala Leu Thr Thr Val Met Ser Pro Cys
        290                 295                 300

Gly Gly Glu Asp Ile Val Ala Asp His Val Ala Ser Tyr Gly Val Asn
305                 310                 315                 320

Leu Tyr Gln Ser Tyr Gly Pro Ser Gly Gln Tyr Ser His Glu Phe Asp
                325                 330                 335

Gly Asp Glu Glu Phe Tyr Val Asp Leu Glu Arg Lys Glu Thr Val Trp
                340                 345                 350

Gln Leu Pro Leu Phe Arg Arg Phe Arg Arg Phe Asp Pro Gln Phe Ala
        355                 360                 365

Leu Thr Asn Ile Ala Val Leu Lys His Asn Leu Asn Ile Val Ile Lys
        370                 375                 380

Arg Ser Asn Ser Thr Ala Ala Thr Asn Glu Val Pro Glu Val Thr Val
385                 390                 395                 400

Phe Ser Lys Ser Pro Val Thr Leu Gly Gln Pro Asn Thr Leu Ile Cys
                405                 410                 415

Leu Val Asp Asn Ile Phe Pro Pro Val Val Asn Ile Thr Trp Leu Ser
        420                 425                 430

Asn Gly His Ser Val Thr Glu Gly Val Ser Glu Thr Ser Phe Leu Ser
```

```
                435         440         445
Lys Ser Asp His Ser Phe Phe Lys Ile Ser Tyr Leu Thr Phe Leu Pro
    450                 455                 460

Ser Ala Asp Glu Ile Tyr Asp Cys Lys Val Glu His Trp Gly Leu Asp
465                 470                 475                 480

Glu Pro Leu Leu Lys His Trp Glu Pro Glu Ile Pro Thr Pro Met Ser
                485                 490                 495

Glu Leu Thr Glu Thr Val Val Cys Ala Leu Gly Leu Ser Val Gly Leu
            500                 505                 510

Val Gly Ile Val Val Gly Thr Val Leu Ile Ile Arg Gly Leu Arg Ser
        515                 520                 525

Val Gly Ala Ser Arg His Gln Gly Pro Leu
    530                 535

<210> SEQ ID NO 44
<211> LENGTH: 66
<212> TYPE: DNA
<213> ORGANISM: Artificial Sequence
<220> FEATURE:
<223> OTHER INFORMATION: Synthetic sequence Porcine teschovirus-1 2A
      (P2A) peptide

<400> SEQUENCE: 44
ggcagcggcg ccaccaactt tagcctgctg aaacaggctg gcgacgtgga agagaacccc    60
ggacct                                                              66

<210> SEQ ID NO 45
<211> LENGTH: 66
<212> TYPE: DNA
<213> ORGANISM: Artificial Sequence
<220> FEATURE:
<223> OTHER INFORMATION: Synthetic sequence Porcine teschovirus-1 2A
      (P2A) peptide

<400> SEQUENCE: 45
ggctctggcg ccaccaactt tagcctgctg aaacaggctg gcgacgtgga agagaacccc    60
ggacct                                                              66

<210> SEQ ID NO 46
<211> LENGTH: 63
<212> TYPE: DNA
<213> ORGANISM: Artificial Sequence
<220> FEATURE:
<223> OTHER INFORMATION: Synthetic sequence Thoseaasigna virus 2A (T2A)
      peptide

<400> SEQUENCE: 46
ggaagcggag agggcagagg aagtctgcta acatgcggtg acgtcgagga gaatcctgga    60
cct                                                                 63

<210> SEQ ID NO 47
<211> LENGTH: 69
<212> TYPE: DNA
<213> ORGANISM: Artificial Sequence
<220> FEATURE:
<223> OTHER INFORMATION: Synthetic sequence Equine rhinitis A virus
      (ERAV) 2A (E2A) peptide

<400> SEQUENCE: 47
ggaagcggac agtgtactaa ttatgctctc ttgaaattgg ctggagatgt tgagagcaac    60
cctggacct                                                           69
```

<210> SEQ ID NO 48
<211> LENGTH: 75
<212> TYPE: DNA
<213> ORGANISM: Artificial Sequence
<220> FEATURE:
<223> OTHER INFORMATION: Synthetic sequence Foot-and-Mouth disease virus
      2A (F2A) peptide

<400> SEQUENCE: 48
ggaagcggag tgaaacagac tttgaatttt gaccttctca agttggcggg agacgtggag      60
tccaaccctg gacct                                                      75

<210> SEQ ID NO 49
<211> LENGTH: 22
<212> TYPE: PRT
<213> ORGANISM: Artificial Sequence
<220> FEATURE:
<223> OTHER INFORMATION: Synthetic sequence Porcine teschovirus-1 2A
      (P2A)

<400> SEQUENCE: 49

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 50
<211> LENGTH: 24
<212> TYPE: PRT
<213> ORGANISM: Artificial Sequence
<220> FEATURE:
<223> OTHER INFORMATION: Synthetic sequence Thoseaasigna virus 2A (T2A)
      peptide

<400> SEQUENCE: 50

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic sequence Equine rhinitis A virus
      (ERAV) 2A (E2A) peptide

<400> SEQUENCE: 51

Gln Cys Thr Asn Tyr Ala Leu Leu Lys Leu Ala Gly Asp Val Glu Ser
1               5                   10                  15

Asn Pro Gly Pro
            20

<210> SEQ ID NO 52
<211> LENGTH: 25
<212> TYPE: PRT
<213> ORGANISM: Artificial Sequence
<220> FEATURE:
<223> OTHER INFORMATION: Synthetic sequence Foot-and-Mouth disease virus
      2A (F2A) peptide

<400> SEQUENCE: 52

Gly Ser Gly Val Lys Gln Thr Leu Asn Phe Asp Leu Leu Lys Leu Ala

```
                1               5                  10                  15
Gly Asp Val Glu Ser Asn Pro Gly Pro
                20                  25

<210> SEQ ID NO 53
<211> LENGTH: 15
<212> TYPE: PRT
<213> ORGANISM: Artificial Sequence
<220> FEATURE:
<223> OTHER INFORMATION: Synthetic sequence Glycine-Serine linker

<400> SEQUENCE: 53

Gly Gly Gly Gly Ser Gly Gly Gly Gly Ser Gly Gly Gly Gly Ser
1               5                  10                  15

<210> SEQ ID NO 54
<211> LENGTH: 18
<212> TYPE: PRT
<213> ORGANISM: Artificial Sequence
<220> FEATURE:
<223> OTHER INFORMATION: Synthetic sequence Glycine-Serine linker

<400> SEQUENCE: 54

Gly Ser Thr Ser Gly Gly Gly Ser Gly Gly Ser Gly Gly Gly Gly
1               5                  10                  15

Ser Ser

<210> SEQ ID NO 55
<211> LENGTH: 271
<212> TYPE: PRT
<213> ORGANISM: Artificial Sequence
<220> FEATURE:
<223> OTHER INFORMATION: Synthetic sequence TCR1 alpha chain (full-
      length)

<400> SEQUENCE: 55

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
        50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Arg Gly Asn Asn Asp Met Arg Phe Gly Ala Gly Thr Arg Leu Thr Val
        115                 120                 125

Lys Pro Asn Ile Gln Asn Pro Asp Pro Ala Val Tyr Gln Leu Arg Asp
130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Cys Val Leu Asp Met Arg Ser Met Asp Phe Lys Ser Asn Ser Ala
            180                 185                 190
```

```
Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
        210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
            245                 250                 255

Val Ala Gly Phe Asn Leu Leu Met Thr Leu Arg Leu Trp Ser Ser
            260                 265                 270

<210> SEQ ID NO 56
<211> LENGTH: 269
<212> TYPE: PRT
<213> ORGANISM: Artificial Sequence
<220> FEATURE:
<223> OTHER INFORMATION: Synthetic sequence TCR2-1 alpha chain
      (full-length)

<400> SEQUENCE: 56

Met Arg Leu Val Ala Arg Val Thr Val Phe Leu Thr Phe Gly Thr Ile
1               5                   10                  15

Ile Asp Ala Lys Thr Thr Gln Pro Thr Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Ala Tyr Ser Gly
            100                 105                 110

Tyr Ser Thr Leu Thr Phe Gly Lys Gly Thr Met Leu Leu Val Ser Pro
        115                 120                 125

Asp Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Cys
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 57
<211> LENGTH: 276
<212> TYPE: PRT
<213> ORGANISM: Artificial Sequence
<220> FEATURE:
<223> OTHER INFORMATION: Synthetic sequence TCR2-2 alpha chain
      (full-length)

<400> SEQUENCE: 57

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65              70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Ile Thr Leu Asn Asn Asn Ala Gly Asn Met Leu Thr Phe Gly Gly Gly
        115                 120                 125

Thr Arg Leu Met Val Lys Pro His Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Cys Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 58
<211> LENGTH: 272
<212> TYPE: PRT
<213> ORGANISM: Artificial Sequence
<220> FEATURE:
<223> OTHER INFORMATION: Synthetic sequence TCR3 alpha chain (full-
      length)

<400> SEQUENCE: 58

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu

```
                    20                  25                  30
    Ser Val Pro Glu Gly Ala Ile Ala Ser Leu Asn Cys Thr Tyr Ser Asp
                35                  40                  45

Arg Gly Ser Gln Ser Phe Phe Trp Tyr Arg Gln Tyr Ser Gly Lys Ser
                50                  55                  60

Pro Glu Leu Ile Met Phe Ile Tyr Ser Asn Gly Asp Lys Glu Asp Gly
    65                  70                  75                  80

Arg Phe Thr Ala Gln Leu Asn Lys Ala Ser Gln Tyr Val Ser Leu Leu
                    85                  90                  95

Ile Arg Asp Ser Gln Pro Ser Asp Ser Ala Thr Tyr Leu Cys Ala Val
                    100                 105                 110

Thr Ser Asn Ala Gly Lys Ser Thr Phe Gly Asp Gly Thr Thr Leu Thr
                    115                 120                 125

Val Lys Pro Asn Ile Gln Asn Pro Asp Pro Ala Val Tyr Gln Leu Arg
                130                 135                 140

Asp Ser Lys Ser Ser Asp Lys Ser Val Cys Leu Phe Thr Asp Phe Asp
    145                 150                 155                 160

Ser Gln Thr Asn Val Ser Gln Ser Lys Asp Ser Asp Val Tyr Ile Thr
                    165                 170                 175

Asp Lys Cys Val Leu Asp Met Arg Ser Met Asp Phe Lys Ser Asn Ser
                    180                 185                 190

Ala Val Ala Trp Ser Asn Lys Ser Asp Phe Ala Cys Ala Asn Ala Phe
                    195                 200                 205

Asn Asn Ser Ile Ile Pro Glu Asp Thr Phe Phe Pro Ser Pro Glu Ser
                210                 215                 220

Ser Cys Asp Val Lys Leu Val Glu Lys Ser Phe Glu Thr Asp Thr Asn
    225                 230                 235                 240

Leu Asn Phe Gln Asn Leu Ser Val Ile Gly Phe Arg Ile Leu Leu Leu
                    245                 250                 255

Lys Val Ala Gly Phe Asn Leu Leu Met Thr Leu Arg Leu Trp Ser Ser
                    260                 265                 270

<210> SEQ ID NO 59
<211> LENGTH: 309
<212> TYPE: PRT
<213> ORGANISM: Artificial Sequence
<220> FEATURE:
<223> OTHER INFORMATION: Synthetic sequence  TCR1 beta chain (full-
      length)

<400> SEQUENCE: 59

Met Gly Ile Arg Leu Leu Cys Arg Val Ala Phe Cys Phe Leu Ala Val
    1               5                   10                  15

Gly Leu Val Asp Val Lys Val Thr Gln Ser Ser Arg Tyr Leu Val Lys
                    20                  25                  30

Arg Thr Gly Glu Lys Val Phe Leu Glu Cys Val Gln Asp Met Asp His
                    35                  40                  45

Glu Asn Met Phe Trp Tyr Arg Gln Asp Pro Gly Leu Gly Leu Arg Leu
                50                  55                  60

Ile Tyr Phe Ser Tyr Asp Val Lys Met Lys Glu Lys Gly Asp Ile Pro
    65                  70                  75                  80

Glu Gly Tyr Ser Val Ser Arg Glu Lys Lys Glu Arg Phe Ser Leu Ile
                    85                  90                  95

Leu Glu Ser Ala Ser Thr Asn Gln Thr Ser Met Tyr Leu Cys Ala Ser
                    100                 105                 110
```

Asn Glu Gly Asn Ser Gly Asn Thr Ile Tyr Phe Gly Glu Gly Ser Trp
            115                 120                 125

Leu Thr Val Val Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
            210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Phe
305

<210> SEQ ID NO 60
<211> LENGTH: 307
<212> TYPE: PRT
<213> ORGANISM: Artificial Sequence
<220> FEATURE:
<223> OTHER INFORMATION: Synthetic sequence  TCR2-1 and 2-2 beta chain
      (full-length)

<400> SEQUENCE: 60

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
            85                  90                  95

Leu Glu Ser Ala Ser Thr Asn Gln Thr Ser Met Tyr Leu Cys Ala Ser
            100                 105                 110

Gly Ala Arg Gln Ile Pro Tyr Thr Phe Gly Ser Gly Thr Arg Leu Thr
            115                 120                 125

Val Val Glu Asp Leu Asn Lys Val Phe Pro Pro Glu Val Ala Val Phe
            130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
            165                 170                 175

Val Asn Gly Lys Glu Val His Ser Gly Val Cys Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
            245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe
305

<210> SEQ ID NO 61
<211> LENGTH: 317
<212> TYPE: PRT
<213> ORGANISM: Artificial Sequence
<220> FEATURE:
<223> OTHER INFORMATION: Synthetic sequence  TCR3 beta chain (full-
      length)

<400> SEQUENCE: 61

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
            85                  90                  95

Leu Glu Ser Ala Ser Thr Asn Gln Thr Ser Met Tyr Leu Cys Ala Ser
        100                 105                 110

Ser Leu Ser Ala Ala Gly Gly Gly Tyr Gly Tyr Thr Phe Asn Tyr Gly
    115                 120                 125

Tyr Thr Phe Gly Ser Gly Thr Arg Leu Thr Val Val Glu Asp Leu Asn
    130                 135                 140

Lys Val Phe Pro Pro Glu Val Ala Val Phe Glu Pro Ser Glu Ala Glu
145                 150                 155                 160

Ile Ser His Thr Gln Lys Ala Thr Leu Val Cys Leu Ala Thr Gly Phe
            165                 170                 175

Phe Pro Asp His Val Glu Leu Ser Trp Trp Val Asn Gly Lys Glu Val
        180                 185                 190

His Ser Gly Val Cys Thr Asp Pro Gln Pro Leu Lys Glu Gln Pro Ala

```
                195                 200                 205
Leu Asn Asp Ser Arg Tyr Cys Leu Ser Ser Arg Leu Arg Val Ser Ala
    210                 215                 220

Thr Phe Trp Gln Asn Pro Arg Asn His Phe Arg Cys Gln Val Gln Phe
225                 230                 235                 240

Tyr Gly Leu Ser Glu Asn Asp Glu Trp Thr Gln Asp Arg Ala Lys Pro
                245                 250                 255

Val Thr Gln Ile Val Ser Ala Glu Ala Trp Gly Arg Ala Asp Cys Gly
                260                 265                 270

Phe Thr Ser Val Ser Tyr Gln Gln Gly Val Leu Ser Ala Thr Ile Leu
                275                 280                 285

Tyr Glu Ile Leu Leu Gly Lys Ala Thr Leu Tyr Ala Val Leu Val Ser
    290                 295                 300

Ala Leu Val Leu Met Ala Met Val Lys Arg Lys Asp Phe
305                 310                 315

<210> SEQ ID NO 62
<211> LENGTH: 816
<212> TYPE: DNA
<213> ORGANISM: Artificial Sequence
<220> FEATURE:
<223> OTHER INFORMATION: Synthetic sequence TCR1 alpha chain (full-
      length)

<400> SEQUENCE: 62
atggaaacac tgctgggcct gctgatcctg tggctgcaac tgcaatgggt gtccagcaag      60
caagaagtga ctcagatccc tgccgctctg tctgtgcctg agggcgaaaa cctggtcctg     120
aactgcagct tcaccgacag cgccatctac aacctgcagt ggttcaggca ggatccaggc     180
aagggcctga catccctgct gctgattcag agcagccaga gagagcagac cagcggcaga     240
ctgaatgcca gcctggataa gtcctccggc agaagcaccc tgtatatcgc cgcttctcag     300
ccaggcgata gcgccacata tctgtgtgcc gttcggagag caacaacga catgagattc     360 ggagccggca ccagactgac cgtgaagccc aacattcaga accccgatcc tgcagtgtac     420
cagctgcggg acagcaagag cagcgacaag agcgtgtgcc tgttcaccga cttcgacagc     480
cagaccaacg tgtcccagag caaggacagc gacgtgtaca tcaccgataa gtgcgtgctg     540
gacatgcgga gcatggactt caagagcaac agcgccgtgg cctggtccaa caagagcgac     600
ttcgcctgcg ccaacgcctt caacaacagc attatccccg aggacacatt cttcccaagc     660
cccgagagca gctgcgacgt gaagctggtg gaaaagagct tcgagacaga caccaacctg     720
aacttccaga acctcagcgt gatcggcttc cggatcctgc tgctgaaggt ggccggcttc     780
aacctgctga tgaccctgcg gctgtggtcc agctga                               816

<210> SEQ ID NO 63
<211> LENGTH: 810
<212> TYPE: DNA
<213> ORGANISM: Artificial Sequence
<220> FEATURE:
<223> OTHER INFORMATION: Synthetic sequence  TCR2-1 alpha chain
      (full-length)

<400> SEQUENCE: 63
atgagactgg tggccagagt gacagtgttc ctgaccttcg gcaccatcat cgacgccaag      60
accacacagc ccaccagcat ggattgtgcc gagggcagag ctgccaacct gccttgtaat     120
cacagcacca tcagcggcaa cgagtacgtg tactggtaca ggcagatcca ctctcagggc     180
```

| cctcagtaca tcatccacgg cctgaagaac aacgagacaa acgagatggc ctctctgatc | 240 |
| atcaccgagg accgcaagag cagcaccctg attctgcctc acgccacact gagagacacc | 300 |
| gccgtgtact actgtatcgt gcgggcctac agcggctaca gcacactgac atttggcaag | 360 |
| ggcaccatgc tgctcgtgtc cccagacatt cagaaccccg atcctgcagt gtaccagctg | 420 |
| cgggacagca agagcagcga caagagcgtg tgcctgttca ccgacttcga cagccagacc | 480 |
| aacgtgtccc agagcaagga cagcgacgtg tacatcaccg ataagtgcgt gctggacatg | 540 |
| cggagcatgg acttcaagag caacagcgcc gtggcctggt ccaacaagag cgacttcgcc | 600 |
| tgcgccaacg ccttcaacaa cagcattatc cccgaggaca cattcttccc aagccccgag | 660 |
| agcagctgcg acgtgaagct ggtggaaaag agcttcgaga cagacaccaa cctgaacttc | 720 |
| cagaacctca gcgtgatcgg cttccggatc ctgctgctga aggtggccgg cttcaacctg | 780 |
| ctgatgaccc tgcggctgtg gtccagctga | 810 |

<210> SEQ ID NO 64
<211> LENGTH: 831
<212> TYPE: DNA
<213> ORGANISM: Artificial Sequence
<220> FEATURE:
<223> OTHER INFORMATION: Synthetic sequence TCR2-2 alpha chain
    (full-length)

<400> SEQUENCE: 64

| atgaagtccc tgagagtgct gctggtcatc ctgtggctgc agctgtcttg ggtctggtcc | 60 |
| cagcagaaag aggtggaaca gaacagcggg cctctgtctg ttcctgaagg cgctatcgcc | 120 |
| tctctgaatt gcacctacag cgacagaggc agccagagct tcttctggta tcggcagtac | 180 |
| agcggcaaga gccccgagct gatcatgttc atctacagca cggcgacaa agaggacggc | 240 |
| cggtttacag cccagctgaa caaggccagc cagtacgtgt cactgctgat cagagacagc | 300 |
| cagcctagcg acagcgccac ctatctgtgt gccgtgatca ccctgaacaa caacgccggc | 360 |
| aacatgctga cctttggcgg cggaacacgg ctgatggtta gccccacat tcagaacccc | 420 |
| gatcctgcag tgtaccagct gcgggacagc aagagcagcg acaagagcgt gtgcctgttc | 480 |
| accgacttcg acgccagac caacgtgtcc cagagcaagg acagcgacgt gtacatcacc | 540 |
| gataagtgcg tgctggacat gcggagcatg gacttcaaga gcaacagcgc cgtggcctgg | 600 |
| tccaacaaga gcgacttcgc ctgcgccaac gccttcaaca cagcattat ccccgaggac | 660 |
| acattcttcc caagccccga gagcagctgc gacgtgaagc tggtggaaaa gagcttcgag | 720 |
| acagacacca acctgaactt ccagaacctc agcgtgatcg gcttccggat cctgctgctg | 780 |
| aaggtggccg gcttcaacct gctgatgacc ctgcggctgt ggtccagctg a | 831 |

<210> SEQ ID NO 65
<211> LENGTH: 819
<212> TYPE: DNA
<213> ORGANISM: Artificial Sequence
<220> FEATURE:
<223> OTHER INFORMATION: Synthetic sequence TCR3 alpha chain (full-
    length)

<400> SEQUENCE: 65

| atgaagtccc tgagagtgct gctggtcatc ctgtggctgc agctgtcttg ggtctggtcc | 60 |
| cagcagaaag aggtggaaca gaacagcggc cctctgtccg ttcctgaagg cgccattgct | 120 |
| agcctgaatt gcacctacag cgaccggggc agccagagct tcttctggta taggcagtac | 180 |
| agcggcaaga gccccgagct gatcatgttc atctacagca cggcgacaa agaggacggc | 240 |

| | |
|---|---|
| cggtttacag cccagctgaa caaggccagc cagtacgtgt cactgctgat cagagacagc | 300 |
| cagcctagcg acagcgccac ctatctgtgt gccgtgacaa gcaatgccgg caagtccaca | 360 |
| tttggcgacg gcacaaccct gaccgtgaag cccaacattc agaacccga tcctgcagtg | 420 |
| taccagctgc gggacagcaa gagcagcgac aagagcgtgt gcctgttcac cgacttcgac | 480 |
| agccagacca acgtgtccca gagcaaggac agcgacgtgt acatcaccga taagtgcgtg | 540 |
| ctggacatgc ggagcatgga cttcaagagc aacagcgccg tggcctggtc caacaagagc | 600 |
| gacttcgcct gcgccaacgc cttcaacaac agcattatcc ccgaggacac attcttccca | 660 |
| agccccgaga gcagctgcga cgtgaagctg gtggaaaaga gcttcgagac agacaccaac | 720 |
| ctgaacttcc agaacctcag cgtgatcggc ttccggatcc tgctgctgaa ggtggccggc | 780 |
| ttcaacctgc tgatgaccct gcggctgtgg tccagctga | 819 |

<210> SEQ ID NO 66
<211> LENGTH: 927
<212> TYPE: DNA
<213> ORGANISM: Artificial Sequence
<220> FEATURE:
<223> OTHER INFORMATION: Synthetic sequence TCR1 beta chain (full-length)

<400> SEQUENCE: 66

| | |
|---|---|
| atgggaatta gactgctgtg cagagtggcc ttctgcttcc tggctgttgg cctggtggac | 60 |
| gtgaaagtga cccagagcag cagatacctg gtcaagagaa ccggcgagaa ggtgttcctg | 120 |
| gaatgcgtgc aggacatgga ccacgagaat atgttctggt acagacagga ccccggcctg | 180 |
| ggcctgagac tgatctactt cagctacgac gtgaagatga aggaaaaggg cgacatcccc | 240 |
| gagggctaca gcgtgtccag agagaagaaa gagcggttca gcctgatcct ggaaagcgcc | 300 |
| agcaccaacc agaccagcat gtacctgtgc gccagcaacg agggcaatag cggcaacacc | 360 |
| atctacttcg gcgaaggcag ctggctgacc gtggtggaag atctgaacaa agtgttccct | 420 |
| ccagaggtgg ccgtgttcga gccttctgag gccgagatca gccacacaca gaaagccaca | 480 |
| ctcgtgtgcc tggccaccgg cttttttccc gatcacgtgg aactgtcttg gtgggtcaac | 540 |
| ggcaaagagg tgcacagcgg cgtctgtacc gatcctcagc tctgaaagaa gcagcccgct | 600 |
| ctgaacgact ccagatactg cctgagcagc aggctgagag tgtccgccac cttctggcag | 660 |
| aaccccagaa accacttcag atgccaggtg cagttctacg gcctgagcga gaacgatgag | 720 |
| tggacccagg atagagccaa gcctgtgaca cagatcgtgt ctgccgaagc tggggcagag | 780 |
| gccgattgtg gctttaccct cgtgtcctat cagcagggcg tgctgtctgc caccatcctg | 840 |
| tatgagatcc tgctgggcaa agccactctg tacgccgtgc tggtgtctgc cctggtgctg | 900 |
| atggccatgg tcaagcggaa ggatttt | 927 |

<210> SEQ ID NO 67
<211> LENGTH: 921
<212> TYPE: DNA
<213> ORGANISM: Artificial Sequence
<220> FEATURE:
<223> OTHER INFORMATION: Synthetic sequence TCR2-1 and 2-2 beta chain (full-length)

<400> SEQUENCE: 67

| | |
|---|---|
| atgggaatta gactgctgtg cagagtggcc ttctgcttcc tggctgttgg cctggtggac | 60 |
| gtgaaagtga cccagagcag cagatacctg gtcaagagaa ccggcgagaa ggtgttcctg | 120 |

-continued

| | |
|---|---|
| gaatgcgtgc aggacatgga ccacgagaat atgttctggt acagacagga ccccggcctg | 180 |
| ggcctgagac tgatctactt cagctacgac gtgaagatga aggaaaaggg cgacatcccc | 240 |
| gagggctaca gcgtgtccag agagaagaaa gagcggttca gcctgatcct ggaaagcgcc | 300 |
| agcaccaacc agaccagcat gtacctgtgt gccagcggcg ccagacagat cccttacaca | 360 |
| tttggctccg gcaccagact gaccgtggtg gaagatctga caaagtgttc cctccagag | 420 |
| gtggccgtgt tcgagccttc tgaggccgag atcagccaca cacagaaagc cacactcgtg | 480 |
| tgcctggcca ccggcttttt tcccgatcac gtggaactgt cttggtgggt caacggcaaa | 540 |
| gaggtgcaca cgccgtctg taccgatcct cagcctctga agagcagcc cgctctgaac | 600 |
| gactccagat actgcctgag cagcaggctg agagtgtccg ccaccttctg gcagaacccc | 660 |
| agaaaccact tcagatgcca ggtgcagttc tacggcctga gcgagaacga tgagtggacc | 720 |
| caggatagag ccaagcctgt gacacagatc gtgtctgccg aagcctgggg cagagccgat | 780 |
| tgtggcttta cctccgtgtc ctatcagcag ggcgtgctgt ctgccaccat cctgtatgag | 840 |
| atcctgctgg gcaaagccac tctgtacgcc gtgctggtgt ctgccctggt gctgatggcc | 900 |
| atggtcaagc ggaaggattt t | 921 |

<210> SEQ ID NO 68
<211> LENGTH: 951
<212> TYPE: DNA
<213> ORGANISM: Artificial Sequence
<220> FEATURE:
<223> OTHER INFORMATION: Synthetic sequence TCR3 beta chain (full-length)

<400> SEQUENCE: 68

| | |
|---|---|
| atgggaatta gactgctgtg cagagtggcc ttctgcttcc tggctgttgg cctggtggac | 60 |
| gtgaaagtga cccagagcag cagataccg gtcaagagaa ccggcgagaa ggtgttcctg | 120 |
| gaatgcgtgc aggacatgga ccacgagaat atgttctggt acagacagga ccccggcctg | 180 |
| ggcctgagac tgatctactt cagctacgac gtgaagatga aggaaaaggg cgacatcccc | 240 |
| gagggctaca gcgtgtccag agagaagaaa gagcggttca gcctgatcct ggaaagcgcc | 300 |
| agcaccaacc agaccagcat gtacctgtgt gccagctctc tgtctgctgc cggcggaggc | 360 |
| tatggctaca ccttcaatta cggctacaca ttcggcagcg gcaccagact gaccgtggtg | 420 |
| gaagatctga caaagtgttc cctccagag gtggccgtgt tcgagccttc tgaggccgag | 480 |
| atcagccaca cacagaaagc cacactcgtg tgcctggcca ccggcttttt tcccgatcac | 540 |
| gtggaactgt cttggtgggt caacggcaaa gaggtgcaca cgccgtctg taccgatcct | 600 |
| cagcctctga agagcagcc cgctctgaac gactccagat actgcctgag cagcaggctg | 660 |
| agagtgtccg ccaccttctg gcagaacccc agaaaccact tcagatgcca ggtgcagttc | 720 |
| tacggcctga gcgagaacga tgagtggacc caggatagag ccaagcctgt gacacagatc | 780 |
| gtgtctgccg aagcctgggg cagagccgat tgtggcttta cctccgtgtc ctatcagcag | 840 |
| ggcgtgctgt ctgccaccat cctgtatgag atcctgctgg gcaaagccac tctgtacgcc | 900 |
| gtgctggtgt ctgccctggt gctgatggcc atggtcaagc ggaaggattt t | 951 |

<210> SEQ ID NO 69
<211> LENGTH: 602
<212> TYPE: PRT
<213> ORGANISM: Artificial Sequence
<220> FEATURE:
<223> OTHER INFORMATION: Synthetic sequence TCR1 (beta-P2A-alpha)

<400> SEQUENCE: 69

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Asn Glu Gly Asn Ser Gly Asn Thr Ile Tyr Phe Gly Glu Gly Ser Trp
        115                 120                 125

Leu Thr Val Val Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Glu Thr Leu Leu
                325                 330                 335

Gly Leu Leu Ile Leu Trp Leu Gln Leu Gln Trp Val Ser Ser Lys Gln
            340                 345                 350

Glu Val Thr Gln Ile Pro Ala Ala Leu Ser Val Pro Glu Gly Glu Asn
        355                 360                 365

Leu Val Leu Asn Cys Ser Phe Thr Asp Ser Ala Ile Tyr Asn Leu Gln
370                 375                 380

Trp Phe Arg Gln Asp Pro Gly Lys Gly Leu Thr Ser Leu Leu Leu Ile
385                 390                 395                 400

Gln Ser Ser Gln Arg Glu Gln Thr Ser Gly Arg Leu Asn Ala Ser Leu
                405                 410                 415

Asp Lys Ser Ser Gly Arg Ser Thr Leu Tyr Ile Ala Ala Ser Gln Pro
        420                 425                 430

Gly Asp Ser Ala Thr Tyr Leu Cys Ala Val Arg Arg Gly Asn Asn Asp
            435                 440                 445

Met Arg Phe Gly Ala Gly Thr Arg Leu Thr Val Lys Pro Asn Ile Gln
    450                 455                 460

Asn Pro Asp Pro Ala Val Tyr Gln Leu Arg Asp Ser Lys Ser Ser Asp
465                 470                 475                 480

Lys Ser Val Cys Leu Phe Thr Asp Phe Asp Ser Gln Thr Asn Val Ser
                485                 490                 495

Gln Ser Lys Asp Ser Asp Val Tyr Ile Thr Asp Lys Cys Val Leu Asp
            500                 505                 510

Met Arg Ser Met Asp Phe Lys Ser Asn Ser Ala Val Ala Trp Ser Asn
        515                 520                 525

Lys Ser Asp Phe Ala Cys Ala Asn Ala Phe Asn Asn Ser Ile Ile Pro
    530                 535                 540

Glu Asp Thr Phe Phe Pro Ser Pro Glu Ser Ser Cys Asp Val Lys Leu
545                 550                 555                 560

Val Glu Lys Ser Phe Glu Thr Asp Thr Asn Leu Asn Phe Gln Asn Leu
                565                 570                 575

Ser Val Ile Gly Phe Arg Ile Leu Leu Leu Lys Val Ala Gly Phe Asn
            580                 585                 590

Leu Leu Met Thr Leu Arg Leu Trp Ser Ser
        595                 600

<210> SEQ ID NO 70
<211> LENGTH: 598
<212> TYPE: PRT
<213> ORGANISM: Artificial Sequence
<220> FEATURE:
<223> OTHER INFORMATION: Synthetic sequence TCR2-1 (beta-P2A-alpha)

<400> SEQUENCE: 70

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Gly Ala Arg Gln Ile Pro Tyr Thr Phe Gly Ser Gly Thr Arg Leu Thr
        115                 120                 125

Val Val Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

-continued

```
Val Asn Gly Lys Glu Val His Ser Gly Val Cys Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Arg Leu Val Ala Arg Val
                325                 330                 335

Thr Val Phe Leu Thr Phe Gly Thr Ile Ile Asp Ala Lys Thr Thr Gln
            340                 345                 350

Pro Thr Ser Met Asp Cys Ala Glu Gly Arg Ala Ala Asn Leu Pro Cys
        355                 360                 365

Asn His Ser Thr Ile Ser Gly Asn Glu Tyr Val Tyr Trp Tyr Arg Gln
    370                 375                 380

Ile His Ser Gln Gly Pro Gln Tyr Ile Ile His Gly Leu Lys Asn Asn
385                 390                 395                 400

Glu Thr Asn Glu Met Ala Ser Leu Ile Ile Thr Glu Asp Arg Lys Ser
                405                 410                 415

Ser Thr Leu Ile Leu Pro His Ala Thr Leu Arg Asp Thr Ala Val Tyr
            420                 425                 430

Tyr Cys Ile Val Arg Ala Tyr Ser Gly Tyr Ser Thr Leu Thr Phe Gly
        435                 440                 445

Lys Gly Thr Met Leu Leu Val Ser Pro Asp Ile Gln Asn Pro Asp Pro
    450                 455                 460

Ala Val Tyr Gln Leu Arg Asp Ser Lys Ser Ser Asp Lys Ser Val Cys
465                 470                 475                 480

Leu Phe Thr Asp Phe Asp Ser Gln Thr Asn Val Ser Gln Ser Lys Asp
                485                 490                 495

Ser Asp Val Tyr Ile Thr Asp Lys Cys Val Leu Asp Met Arg Ser Met
            500                 505                 510

Asp Phe Lys Ser Asn Ser Ala Val Ala Trp Ser Asn Lys Ser Asp Phe
        515                 520                 525

Ala Cys Ala Asn Ala Phe Asn Asn Ser Ile Ile Pro Glu Asp Thr Phe
    530                 535                 540

Phe Pro Ser Pro Glu Ser Ser Cys Asp Val Lys Leu Val Glu Lys Ser
545                 550                 555                 560

Phe Glu Thr Asp Thr Asn Leu Asn Phe Gln Asn Leu Ser Val Ile Gly
                565                 570                 575

Phe Arg Ile Leu Leu Leu Lys Val Ala Gly Phe Asn Leu Leu Met Thr
            580                 585                 590
```

Leu Arg Leu Trp Ser Ser
        595

<210> SEQ ID NO 71
<211> LENGTH: 605
<212> TYPE: PRT
<213> ORGANISM: Artificial Sequence
<220> FEATURE:
<223> OTHER INFORMATION: Synthetic sequence TCR2-2 amino acid
      (beta-P2A-alpha)

<400> SEQUENCE: 71

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Gly Ala Arg Gln Ile Pro Tyr Thr Phe Gly Ser Gly Thr Arg Leu Thr
        115                 120                 125

Val Val Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Cys Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Lys Ser Leu Arg Val Leu
                325                 330                 335

Leu Val Ile Leu Trp Leu Gln Leu Ser Trp Val Trp Ser Gln Gln Lys
            340                 345                 350

```
Glu Val Glu Gln Asn Ser Gly Pro Leu Ser Val Pro Glu Gly Ala Ile
            355                 360                 365

Ala Ser Leu Asn Cys Thr Tyr Ser Asp Arg Gly Ser Gln Ser Phe Phe
        370                 375                 380

Trp Tyr Arg Gln Tyr Ser Gly Lys Ser Pro Glu Leu Ile Met Phe Ile
385                 390                 395                 400

Tyr Ser Asn Gly Asp Lys Glu Asp Gly Arg Phe Thr Ala Gln Leu Asn
                405                 410                 415

Lys Ala Ser Gln Tyr Val Ser Leu Leu Ile Arg Asp Ser Gln Pro Ser
                420                 425                 430

Asp Ser Ala Thr Tyr Leu Cys Ala Val Ile Thr Leu Asn Asn Asn Ala
            435                 440                 445

Gly Asn Met Leu Thr Phe Gly Gly Gly Thr Arg Leu Met Val Lys Pro
        450                 455                 460

His Ile Gln Asn Pro Asp Pro Ala Val Tyr Gln Leu Arg Asp Ser Lys
465                 470                 475                 480

Ser Ser Asp Lys Ser Val Cys Leu Phe Thr Asp Phe Asp Ser Gln Thr
                485                 490                 495

Asn Val Ser Gln Ser Lys Asp Ser Asp Val Tyr Ile Thr Asp Lys Cys
                500                 505                 510

Val Leu Asp Met Arg Ser Met Asp Phe Lys Ser Asn Ser Ala Val Ala
            515                 520                 525

Trp Ser Asn Lys Ser Asp Phe Ala Cys Ala Asn Ala Phe Asn Asn Ser
        530                 535                 540

Ile Ile Pro Glu Asp Thr Phe Phe Pro Ser Pro Glu Ser Ser Cys Asp
545                 550                 555                 560

Val Lys Leu Val Glu Lys Ser Phe Glu Thr Asp Thr Asn Leu Asn Phe
                565                 570                 575

Gln Asn Leu Ser Val Ile Gly Phe Arg Ile Leu Leu Leu Lys Val Ala
                580                 585                 590

Gly Phe Asn Leu Leu Met Thr Leu Arg Leu Trp Ser Ser
        595                 600                 605

<210> SEQ ID NO 72
<211> LENGTH: 476
<212> TYPE: PRT
<213> ORGANISM: Artificial Sequence
<220> FEATURE:
<223> OTHER INFORMATION: Synthetic sequence TCR3 amino acid
      (beta-P2A-alpha)

<400> SEQUENCE: 72

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
```

```
            100                 105                 110
Ser Leu Ser Ala Ala Gly Gly Gly Tyr Gly Tyr Thr Phe Asn Tyr Gly
            115                 120                 125

Tyr Thr Phe Gly Ser Gly Thr Arg Leu Thr Val Val Glu Asp Leu Asn
            130                 135                 140

Lys Val Phe Pro Pro Glu Val Ala Val Phe Glu Pro Ser Glu Ala Glu
145                 150                 155                 160

Ile Ser His Thr Gln Lys Ala Thr Leu Val Cys Leu Ala Thr Gly Phe
            165                 170                 175

Phe Pro Asp His Val Glu Leu Ser Trp Trp Val Asn Gly Lys Glu Val
            180                 185                 190

His Ser Gly Val Cys Thr Asp Pro Gln Pro Leu Lys Glu Gln Pro Ala
            195                 200                 205

Leu Asn Asp Ser Arg Tyr Cys Leu Ser Ser Arg Leu Arg Val Ser Ala
            210                 215                 220

Thr Phe Trp Gln Asn Pro Arg Asn His Phe Arg Cys Gln Val Gln Phe
225                 230                 235                 240

Tyr Gly Leu Ser Glu Asn Asp Glu Trp Thr Gln Asp Arg Ala Lys Pro
            245                 250                 255

Val Thr Gln Ile Val Ser Ala Glu Ala Trp Gly Arg Ala Asp Cys Gly
            260                 265                 270

Phe Thr Ser Val Ser Tyr Gln Gln Gly Val Leu Ser Ala Thr Ile Leu
            275                 280                 285

Tyr Glu Ile Leu Leu Gly Lys Ala Thr Leu Tyr Ala Val Leu Val Ser
            290                 295                 300

Ala Leu Val Leu Met Ala Met Val Lys Arg Lys Asp Phe Gly Ser Gly
305                 310                 315                 320

Ala Thr Asn Phe Ser Leu Leu Lys Gln Ala Gly Asp Val Glu Glu Asn
            325                 330                 335

Pro Gly Pro Met Lys Ser Leu Arg Val Leu Leu Val Ile Leu Trp Leu
            340                 345                 350

Gln Leu Ser Trp Val Trp Ser Gln Gln Lys Glu Val Glu Gln Asn Ser
            355                 360                 365

Gly Pro Leu Ser Val Pro Glu Gly Ala Ile Ala Ser Leu Asn Cys Thr
            370                 375                 380

Tyr Ser Asp Arg Gly Ser Gln Ser Phe Phe Trp Tyr Arg Gln Tyr Ser
385                 390                 395                 400

Gly Lys Ser Pro Glu Leu Ile Met Phe Ile Tyr Ser Asn Gly Asp Lys
            405                 410                 415

Glu Asp Gly Arg Phe Thr Ala Gln Leu Asn Lys Ala Ser Gln Tyr Val
            420                 425                 430

Ser Leu Leu Ile Arg Asp Ser Gln Pro Ser Asp Ser Ala Thr Tyr Leu
            435                 440                 445

Cys Ala Val Thr Ser Asn Ala Gly Lys Ser Thr Phe Gly Asp Gly Thr
            450                 455                 460

Thr Leu Thr Val Lys Pro Asn Ile Gln Asn Pro Asp
465                 470                 475

<210> SEQ ID NO 73
<211> LENGTH: 1809
<212> TYPE: DNA
<213> ORGANISM: Artificial Sequence
<220> FEATURE:
<223> OTHER INFORMATION: Synthetic sequence TCR1 (beta-P2A-alpha)
```

<400> SEQUENCE: 73

```
atgggaatta gactgctgtg cagagtggcc ttctgcttcc tggctgttgg cctggtggac    60
gtgaaagtga cccagagcag cagatacctg gtcaagagaa ccggcgagaa ggtgttcctg   120
gaatgcgtgc aggacatgga ccacgagaat atgttctggt acagacagga ccccggcctg   180
ggcctgagac tgatctactt cagctacgac gtgaagatga aggaaaaggg cgacatcccc   240
gagggctaca gcgtgtccag agagaagaaa gagcggttca gcctgatcct ggaaagcgcc   300
agcaccaacc agaccagcat gtacctgtgc gccagcaacg agggcaatag cggcaacacc   360
atctacttcg gcgaaggcag ctggctgacc gtggtggaag atctgaacaa agtgttccct   420
ccagaggtgg ccgtgttcga gccttctgag ccgagatca gccacacaca gaaagccaca   480
ctcgtgtgcc tggccaccgg cttttttccc gatcacgtgg aactgtcttg gtgggtcaac   540
ggcaaagagg tgcacagcgg cgtctgtacc gatcctcagc ctctgaaaga gcagcccgct   600
ctgaacgact ccagatactg cctgagcagc aggctgagag tgtccgccac cttctggcag   660
aaccccagaa accacttcag atgccaggtg cagttctacg gcctgagcga gaacgatgag   720
tggacccagg atagagccaa gcctgtgaca cagatcgtgt ctgccgaagc tggggcaga   780
gccgattgtg gctttacctc cgtgtcctat cagcagggcg tgctgtctgc caccatcctg   840
tatgagatcc tgctgggcaa agccactctg tacgccgtgc tggtgtctgc cctggtgctg   900
atggccatgg tcaagcggaa ggattttggc agcggcgcca ccaactttag cctgctgaaa   960
caggctggcg acgtggaaga gaaccccgga cctatggaaa cactgctggg cctgctgatc  1020
ctgtggctgc aactgcaatg ggtgtccagc aagcaagaag tgactcagat ccctgccgct  1080
ctgtctgtgc ctgagggcga aaacctggtc ctgaactgca gcttcaccga cagcgccatc  1140
tacaacctgc agtggttcag gcaggatcca ggcaagggcc tgacatccct gctgctgatt  1200
cagagcagcc agagagagca gaccagcggc agactgaatg ccagcctgga taagtcctcc  1260
ggcagaagca ccctgtatat cgccgcttct cagccaggcg atagcgccac atatctgtgt  1320
gccgttcgga gaggcaacaa cgacatgaga ttcggagccg gcaccagact gaccgtgaag  1380
cccaacattc agaaccccga tcctgcagtg taccagctgc gggacagcaa gagcagcgac  1440
aagagcgtgt gcctgttcac cgacttcgac agccagacca cgtgtcccca gagcaaggac  1500
agcgacgtgt acatcaccga taagtgcgtg ctggacatgc ggagcatgga cttcaagagc  1560
aacagcgccg tggcctggtc caacaagagc gacttcgcct gcgccaacgc cttcaacaac  1620
agcattatcc ccgaggacac attcttccca agccccgaga gcagctgcga cgtgaagctg  1680
gtggaaaaga gcttcgagac agacaccaac ctgaacttcc agaacctcag cgtgatcggc  1740
ttccggatcc tgctgctgaa ggtggccggc ttcaacctgc tgatgaccct gcggctgtgg  1800
tccagctga                                                          1809
```

<210> SEQ ID NO 74
<211> LENGTH: 1797
<212> TYPE: DNA
<213> ORGANISM: Artificial Sequence
<220> FEATURE:
<223> OTHER INFORMATION: Synthetic sequence TCR2-1 (beta-P2A-alpha)

<400> SEQUENCE: 74

```
atgggaatta gactgctgtg cagagtggcc ttctgcttcc tggctgttgg cctggtggac    60
gtgaaagtga cccagagcag cagatacctg gtcaagagaa ccggcgagaa ggtgttcctg   120
gaatgcgtgc aggacatgga ccacgagaat atgttctggt acagacagga ccccggcctg   180
```

```
ggcctgagac tgatctactt cagctacgac gtgaagatga aggaaaaggg cgacatcccc    240
gagggctaca gcgtgtccag agagaagaaa gagcggttca gcctgatcct ggaaagcgcc    300
agcaccaacc agaccagcat gtacctgtgt gccagcggcg ccagacagat cccttacaca    360
tttggctccg gcaccagact gaccgtggtg gaagatctga caaagtgtt ccctccagag    420 gtggccgtgt tcgagccttc tgaggccgag atcagccaca cacagaaagc cacactcgtg    480
tgcctggcca ccggcttttt tcccgatcac gtggaactgt cttggtgggt caacggcaaa    540
gaggtgcaca gcggcgtctg taccgatcct cagcctctga agagcagcc cgctctgaac    600 gactccagat actgcctgag cagcaggctg agagtgtccg ccaccttctg cagaaccccc    660
agaaaccact tcagatgcca ggtgcagttc tacggcctga gcgagaacga tgagtggacc    720
caggatagag ccaagcctgt gacacagatc gtgtctgccg aagcctgggg cagagccgat    780
tgtggcttta cctccgtgtc ctatcagcag ggcgtgctgt ctgccaccat cctgtatgag    840
atcctgctgg gcaaagccac tctgtacgcc gtgctggtgt ctgccctggt gctgatggcc    900
atggtcaagc ggaaggattt tgctctggc gccaccaact ttagcctgct gaaacaggct    960
ggcgacgtgg aagagaaccc cggacctatg agactggtgg ccagagtgac agtgttcctg   1020
accttcggca ccatcatcga cgccaagacc acacagccca ccagcatgga ttgtgccgag   1080
ggcagagctg ccaacctgcc ttgtaatcac agcaccatca gcggcaacga gtacgtgtac   1140
tggtacaggc agatccactc tcagggccct cagtacatca tccacggcct gaagaacaac   1200
gagacaaacg agatggcctc tctgatcatc accgaggacc gcaagagcag caccctgatt   1260
ctgcctcacg ccacactgag agacaccgcc gtgtactact gtatcgtgcg ggcctacagc   1320
ggctacagca cactgactat tggcaagggc accatgctgc tcgtgtcccc agacattcag   1380
aaccccgatc ctgcagtgta ccagctgcgg gacagcaaga gcagcgacaa gagcgtgtgc   1440
ctgttcaccg acttcgacag ccagaccaac gtgtcccaga gcaaggacag cgacgtgtac   1500
atcaccgata agtgcgtgct ggacatgcgg agcatggact tcaagagcaa cagcgccgtg   1560
gcctggtcca acaagagcga cttcgcctgc gccaacgcct tcaacaacag cattatcccc   1620
gaggacacat tcttcccaag ccccgagagc agctgcgacg tgaagctggt ggaaaagagc   1680
ttcgagacag acaccaacct gaacttccag aacctcagcg tgatcggctt ccggatcctg   1740
ctgctgaagg tggccggctt caacctgctg atgaccctgc ggctgtggtc cagctga     1797
```

<210> SEQ ID NO 75
<211> LENGTH: 1818
<212> TYPE: DNA
<213> ORGANISM: Artificial Sequence
<220> FEATURE:
<223> OTHER INFORMATION: Synthetic sequence TCR2-2 amino acid
      (beta-P2A-alpha)

<400> SEQUENCE: 75

```
atgggaatta gactgctgtg cagagtggcc ttctgcttcc tggctgttgg cctggtggac     60
gtgaaagtga cccagagcag cagatacctg gtcaagagaa ccggcgagaa ggtgttcctg    120
gaatgcgtgc aggacatgga ccacgagaat atgttctggt acagacagga ccccggcctg    180
ggcctgagac tgatctactt cagctacgac gtgaagatga aggaaaaggg cgacatcccc    240
gagggctaca gcgtgtccag agagaagaaa gagcggttca gcctgatcct ggaaagcgcc    300
agcaccaacc agaccagcat gtacctgtgt gccagcggcg ccagacagat cccttacaca    360
tttggctccg gcaccagact gaccgtggtg gaagatctga caaagtgtt ccctccagag    420
```

```
gtggccgtgt tcgagccttc tgaggccgag atcagccaca cacagaaagc cacactcgtg    480
tgcctggcca ccggctttt tcccgatcac gtggaactgt cttggtgggt caacggcaaa    540
gaggtgcaca gcggcgtctg taccgatcct cagcctctga agagcagcc cgctctgaac    600 gactccagat actgcctgag cagcaggctg agagtgtccg ccaccttctg cagaaacccc    660
agaaaccact tcagatgcca ggtgcagttc tacggcctga gcgagaacga tgagtggacc    720
caggatagag ccaagcctgt gacacagatc gtgtctgccg aagcctgggg cagagccgat    780
tgtggcttta cctccgtgtc ctatcagcag ggcgtgctgt ctgccaccat cctgtatgag    840
atcctgctgg gcaaagccac tctgtacgcc gtgctggtgt ctgccctggt gctgatggcc    900
atggtcaagc ggaaggattt tggctctggc gccaccaact ttagcctgct gaaacaggct    960
ggcgacgtgg aagagaaccc cggacctatg aagtccctga gagtgctgct ggtcatcctg   1020
tggctgcagc tgtcttgggt ctggtcccag cagaaagagg tggaacagaa cagcggccct   1080
ctgtctgttc ctgaaggcgc tatcgcctct ctgaattgca cctacagcga cagaggcagc   1140
cagagcttct tctggtatcg gcagtacagc ggcaagagcc ccgagctgat catgttcatc   1200
tacagcaacg gcgacaaaga ggacggccgg tttacagccc agctgaacaa ggccagccag   1260
tacgtgtcac tgctgatcag agacagccag cctagcgaca gcgccaccta tctgtgtgcc   1320
gtgatcaccc tgaacaacaa cgccggcaac atgctgacct ttggcggcgg aacacggctg   1380
atggttaagc cccacattca gaaccccgat cctgcagtgt accagctgcg ggacagcaag   1440
agcagcgaca gagcgtgtg cctgttcacc gacttcgaca gccagaccaa cgtgtcccag   1500
agcaaggaca gcgacgtgta catcaccgat aagtgcgtgc tggacatgcg gagcatggac   1560
ttcaagagca cagcgccgt ggcctggtcc aacaagagcg acttcgcctg cgccaacgcc   1620
ttcaacaaca gcattatccc cgaggacaca ttcttcccaa gccccgagag cagctgcgac   1680
gtgaagctgg tggaaaagag cttcgagaca gacaccaacc tgaacttcca gaaccctcagc   1740 gtgatcggct tccggatcct gctgctgaag gtggccggct caaccctgct gatgacctg   1800 cggctgtggt ccagctga                                                  1818
```

<210> SEQ ID NO 76
<211> LENGTH: 1429
<212> TYPE: DNA
<213> ORGANISM: Artificial Sequence
<220> FEATURE:
<223> OTHER INFORMATION: Synthetic sequence TCR3 amino acid
      (beta-P2A-alpha)

<400> SEQUENCE: 76

```
atgggaatta gactgctgtg cagagtggcc ttctgcttcc tggctgttgg cctggtggac     60
gtgaaagtga cccagagcag cagataccrg gtcaagagaa ccggcgagaa ggtgttcctg    120
gaatgcgtgc aggacatgga ccacgagaat atgttctggt acagacagga ccccggcctg    180
ggcctgagac tgatctactt cagctacgac gtgaagatga aggaaaaggg cgacatcccc    240
gagggctaca gcgtgtccag agagaagaaa gagcggttca gcctgatcct ggaaagcgcc    300
agcaccaacc agaccagcat gtacctgtgt gccagctctc tgtctgctgc cggcggaggc    360
tatggctaca ccttcaatta cggctacaca ttcggcagcg gcaccagact gaccgtggtg    420
gaagatctga caaagtgtt ccctccagag gtggccgtgt tcgagccttc tgaggccgag    480
atcagccaca cacagaaagc cacactcgtg tgcctggcca ccggctttt tcccgatcac    540 gtggaactgt cttggtgggt caacggcaaa gaggtgcaca gcggcgtctg taccgatcct    600
```

```
cagcctctga aagagcagcc cgctctgaac gactccagat actgcctgag cagcaggctg    660
agagtgtccg ccaccttctg gcagaacccc agaaaccact tcagatgcca ggtgcagttc    720
tacggcctga gcgagaacga tgagtggacc caggatagag ccaagcctgt gacacagatc    780
gtgtctgccg aagcctgggg cagagccgat tgtggcttta cctccgtgtc ctatcagcag    840
ggcgtgctgt ctgccaccat cctgtatgag atcctgctgg gcaaagccac tctgtacgcc    900
gtgctggtgt ctgccctggt gctgatggcc atggtcaagc ggaaggattt tggcagcggc    960
gccaccaact ttagcctgct gaaacaggct ggcgacgtgg aagagaaccc cggacctatg   1020
aagtccctga gagtgctgct ggtcatcctg tggctgcagc tgtcttgggt ctggtcccag   1080
cagaaagagg tggaacagaa cagcggccct ctgtccgttc ctgaaggcgc cattgctagc   1140
ctgaattgca cctacagcga ccgggggcagc cagagcttct tctggtatag cagtacagc   1200 ggcaagagcc ccgagctgat catgttcatc tacagcaacg gcgacaaaga ggacggccgg   1260
tttacagccc agctgaacaa ggccagccag tacgtgtcac tgctgatcag agacagccag   1320
cctagcgaca gcgccaccta tctgtgtgcc gtgacaagca atgccggcaa gtccacattt   1380
ggcgacggca aaccctgac cgtgaagccc aacattcaga ccccgatc                 1429
```

<210> SEQ ID NO 77
<211> LENGTH: 8298
<212> TYPE: DNA
<213> ORGANISM: Artificial Sequence
<220> FEATURE:
<223> OTHER INFORMATION: Synthetic sequence pRRLSIN-P2A-aWPRE-PST1

<400> SEQUENCE: 77

```
tcgagggaat gaaagacccc acctgtaggt ttggcaagct agcttaagta acgccatttt     60
gcaaggcatg gaaaatacat aactgagaat agagaagttc agatcaaggt taggaacaga    120
gagacagcag aatatgggcc aaacaggata tctgtggtaa gcagttcctg ccccggctca    180
gggccaagaa cagatggtcc ccagatgcgg tcccgccctc agcagtttct agagaaccat    240
cagatgtttc cagggtgccc caaggacctg aaaatgaccc tgtgccttat ttgaactaac    300
caatcagttc gcttctcgct tctgttcgcg cgcttctgct ccccgagctc aataaaagag    360
cccacaaccc ctcactcggc gcgccggcca ccatgagcaa ccaggtgctg tgctgcgtgg    420
tgctgtgttt cctgggcgcc aacaccgtgg acggcggcat cacccagagc cccaagtacc    480
tgttccggaa agagggccag aacgtcaccc tgagctgcga gcagaacctg aaccacgacg    540
ccatgtactg gtacagacag gaccccgcca gggcctgcg gctgatctac tacagccaga    600
tcgtgaacga cttccagaag ggagatatcg ccgagggcta cagcgtgtcc agagagaaga    660
aagagtcctt cccactgacc gtgaccagcg cccagaagaa ccccaccgcc ttctacctgt    720
gcgccagctc tcctggcgcc ctgtacgagc agtacttcgg ccctggcacc cggctgacag    780
tgaccgagga cctgaagaac gtgttccccc cagaggtggc cgtgttcgag cctagcgagg    840
ccgagatcag ccacacccag aaagccaccc tcgtgtgcct ggccaccggc ttttaccccg    900
accacgtgga actgtcttgg tgggtcaacg gcaaagaggt gcacagcggc gtctgcaccg    960
acccccagcc cctgaaagag cagcccgccc tgaacgacag ccggtactgt ctgagcagca   1020
gactgagagt gtccgccacc ttctggcaga acccccggaa ccacttcaga tgccaggtgc   1080
agttctacgg cctgagcgag aacgacgagt ggacccagga ccgggccaag cccgtgaccc   1140
agatcgtgtc tgctgaggcc tggggcagag ccgattgcgg cttcaccagc gagagctacc   1200
```

```
agcagggcgt gctgagcgcc accatcctgt acgagatcct gctgggcaag gccaccctgt    1260
acgccgtgct ggtgtccgcc ctggtgctga tggccatggt caagcggaag gacagccggg    1320
gcggttccgg agccacgaac ttctctctgt taaagcaagc aggagacgtg gaagaaaacc    1380
ccggtcccat gaccagcatc cgggccgtgt tcatcttcct gtggctgcag ctggacctcg    1440
tcaacggcga gaacgtggaa cagcacccca gcaccctgag cgtgcaggaa ggcgacagcg    1500
ccgtcatcaa gtgcacctac agcgactccg ccagcaacta cttcccctgg tacaagcagg    1560
aactgggcaa gcggccccag ctgatcatcg acatccggtc caacgtgggc gagaagaagg    1620
accagcggat cgccgtgacc ctgaacaaga ccgccaagca cttcagcctg cacatcaccg    1680
agacacagcc cgaggactcc gccgtgtact tctgtgccgc caccgaggac taccagctga    1740
tctggggagc cggcaccaag ctgatcatta gccccgacat ccagaacccc gaccctgcag    1800
tgtaccagct gcgggacagc aagagcagcg acaagagcgt gtgcctgttc accgacttcg    1860
acagccagac caacgtgtcc cagagcaagg acagcgacgt gtacatcacc gataagtgcg    1920
tgctggacat gcggagcatg gacttcaaga gcaacagcgc cgtggcctgg tccaacaaga    1980
gcgacttcgc ctgcgccaac gccttcaaca acagcattat ccccgaggac acattcttcc    2040
caagccccga gagcagctgc gacgtgaagc tggtggaaaa gagcttcgag acagacacca    2100
acctgaactt ccagaacctc agcgtgatcg gcttccggat cctgctgctg aaggtggccg    2160
gcttcaacct gctgatgacc ctgcggctgt ggtccagctg agtcgacaat caacctctgg    2220
attacaaaat ttgtgaaaga ttgactggta ttcttaacta tgttgctcct tttacgctat    2280
gtggatacgc tgctttaatg cctttgtatc atgctattgc ttcccgtatg ctttcatttt    2340
tctcctcctt gtataaatcc tggttgctgt ctctttatga ggagttgtgg cccgttgtca    2400
ggcaacgtgg cgtggtgtgc actgtgtttg ctgacgcaac ccccactggt tggggcattg    2460
ccaccacctg tcagctcctt tccgggactt tcgctttccc cctccctatt gccacggcgg    2520
aactcatcgc cgcctgcctt gcccgctgct ggacaggggc tcggctgttg ggcactgaca    2580
attccgtggt gttgtcgggg aaatcatcgt cctttccttg gctgctcgcc tgtgttgcca    2640
cctggattct gcgcgggacg tccttctgct acgtcccttc ggccctcaat ccagcggacc    2700
ttccttcccg cggcctgctg ccggctctgc ggcctcttcc gcgtcttcgc cttcgccctc    2760
agacgagtcg atctccctt tgggccgcct ccccgcctgg aattcgagct cggtacccttt    2820 aagaccaatg acttacaagg cagctgtaga tcttagccac ttttttaaaag aaaaggggg    2880 actggaaggg ctaattcact cccaacgaag acaagatctg cttttttgctt gtactgggtc    2940 tctctggtta gaccagatct gagcctggga gctctctggc taactaggga acccactgct    3000
taagcctcaa taaagcttgc cttgagtgct tcaagtagtg tgtgcccgtc tgttgtgtga    3060
ctctggtaac tagagatccc tcagaccctt ttagtcagtg tggaaaatct ctagcagtag    3120
tagttcatgt catcttatta ttcagtattt ataacttgca aagaaatgaa tatcagagag    3180
tgagaggaac ttgtttattg cagcttataa tggttacaaa taaagcaata gcatcacaaa    3240
tttcacaaat aaagcatttt tttcactgca ttctagttgt ggtttgtcca aactcatcaa    3300
tgtatcttat catgtctggc tctagctatc ccgcccctaa ctccgcccag ttccgcccat    3360
tctccgcccc atggctgact aattttttttt atttatgcag aggccgaggc cgcctcggcc    3420
tctgagctat tccagaagta gtgaggaggc ttttttggag gcctaggctt ttgcgtcgag    3480
acgtacccaa ttcgccctat agtgagtcgt attacgcgcg ctcactggcc gtcgttttac    3540
aacgtcgtga ctgggaaaac cctggcgtta cccaacttaa tcgccttgca gcacatcccc    3600
```

```
ctttcgccag ctggcgtaat agcgaagagg cccgcaccga tcgcccttcc aacagttgc   3660 gcagcctgaa tggcgaatgg cgcgacgcgc cctgtagcgg cgcattaagc gcggcgggtg   3720
tggtggttac gcgcagcgtg accgctacac ttgccagcgc cctagcgccc gctccttcg    3780 ctttcttccc ttcctttctc gccacgttcg ccggctttcc ccgtcaagct ctaaatcggg   3840
ggctcccttt agggttccga tttagtgctt tacggcacct cgaccccaaa aaacttgatt   3900
agggtgatgg ttcacgtagt gggccatcgc cctgatagac ggttttttcgc cctttgacgt  3960 tggagtccac gttctttaat agtggactct tgttccaaac tggaacaaca ctcaaccta    4020 tctcggtcta ttcttttgat ttataaggga ttttgccgat ttcggcctat tggttaaaaa   4080
atgagctgat ttaacaaaaa tttaacgcga attttaacaa atattaacg tttacaattt    4140 cccaggtggc acttttcggg gaaatgtgcg cggaacccct atttgtttat ttttctaaat   4200
acattcaaat atgtatccgc tcatgagaca ataaccctga taaatgcttc aataatattg   4260
aaaaaggaag agtatgagta ttcaacattt ccgtgtcgcc cttattccct tttttgcggc    4320
attttgcctt cctgtttttg ctcacccaga aacgctggtg aaagtaaaag atgctgaaga   4380
tcagttgggt gcacgagtgg gttacatcga actggatctc aacagcggta agatccttga   4440
gagttttcgc cccgaagaac gttttccaat gatgagcact tttaaagttc tgctatgtgg   4500
cgcggtatta tcccgtattg acgccgggca agagcaactc ggtcgccgca tacactattc   4560
tcagaatgac ttggttgagt actcaccagt cacagaaaag catcttacgg atggcatgac   4620
agtaagagaa ttatgcagtg ctgccataac catgagtgat aacactgcgg ccaacttact   4680
tctgacaacg atcggaggac cgaaggagct aaccgctttt ttgcacaaca tgggggatca   4740
tgtaactcgc cttgatcgtt gggaaccgga gctgaatgaa gccataccaa acgacgagcg   4800
tgacaccacg atgcctgtag caatggcaac aacgttgcgc aaactattaa ctggcgaact   4860
acttactcta gcttcccggc aacaattaat agactggatg gaggcggata agttgcagg    4920 accacttctg cgctcggccc ttccggctgg ctggtttatt gctgataaat ctggagccgg   4980
tgagcgtggg tctcgcggta tcattgcagc actggggcca gatggtaagc cctcccgtat   5040
cgtagttatc tacacgacgg ggagtcaggc aactatggat gaacgaaata gacagatcgc   5100
tgagataggt gcctcactga ttaagcattg gtaactgtca gaccaagttt actcatatat   5160
actttagatt gatttaaaac ttcattttta atttaaaagg atctaggtga agatcctttt   5220
tgataatctc atgaccaaaa tcccttaacg tgagttttcg ttccactgag cgtcagaccc   5280
cgtagaaaag atcaaaggat cttcttgaga tccttttttt ctgcgcgtaa tctgctgctt   5340
gcaaacaaaa aaccaccgc taccagcggt ggtttgtttg ccggatcaag agctaccaac    5400 tcttttccg aagtaactg gcttcagcag agcgcagata ccaaatactg tccttctagt    5460
gtagccgtag ttaggccacc acttcaagaa ctctgtagca ccgcctacat acctcgctct   5520
gctaatcctg ttaccagtgg ctgctgccag tggcgataag tcgtgtctta ccgggttgga   5580
ctcaagacga tagttaccgg ataaggcgca gcggtcgggc tgaacggggg gttcgtgcac   5640
acagcccagc ttggagcgaa cgacctacac cgaactgaga tacctacagc gtgagctatg   5700
agaaagcgcc acgcttcccg aagggagaaa ggcggacagg tatccggtaa gcggcagggt   5760
cggaacagga gagcgcacga gggagcttcc agggggaaac gcctggtatc tttatagtcc   5820
tgtcgggttt cgccacctct gacttgagcg tcgatttttg tgatgctcgt caggggggcg   5880
gagcctatgg aaaaacgcca gcaacgcggc cttttacgg ttcctggcct tttgctggcc    5940
```

```
ttttgctcac atgttctttc ctgcgttatc ccctgattct gtggataacc gtattaccgc    6000
ctttgagtga gctgataccg ctcgccgcag ccgaacgacc gagcgcagcg agtcagtgag    6060
cgaggaagcg gaagagcgcc caatacgcaa accgcctctc cccgcgcgtt ggccgattca    6120
ttaatgcagc tggcacgaca ggtttcccga ctggaaagcg ggcagtgagc gcaacgcaat    6180
taatgtgagt tagctcactc attaggcacc ccaggcttta cactttatgc ttccggctcg    6240
tatgttgtgt ggaattgtga gcggataaca atttcacaca ggaaacagct atgaccatga    6300
ttacgccaag cgcgcaatta accctcacta agggaacaa  aagctggagc tgcaagctta    6360
atgtagtctt atgcaatact cttgtagtct tgcaacatgg taacgatgag ttagcaacat    6420
gccttacaag gagagaaaaa gcaccgtgca tgccgattgg tggaagtaag gtggtacgat    6480
cgtgccttat taggaaggca acagacgggt ctgacatgga ttggacgaac cactgaattg    6540
ccgcattgca gagatattgt atttaagtgc ctagctcgat acaataaacg ggtctctctg    6600
gttagaccag atctgagcct gggagctctc tggctaacta gggaacccac tgcttaagcc    6660
tcaataaagc ttgccttgag tgcttcaagt agtgtgtgcc cgtctgttgt gtgactctgg    6720
taactagaga tccctcagac ccttttagtc agtgtggaaa atctctagca gtggcgcccg    6780
aacagggacc tgaaagcgaa agggaaacca gagctctctc gacgcaggac tcggcttgct    6840
gaagcgcgca cggcaagagg cgaggggcgg cgactggtga gtacgccaaa aattttgact    6900
agcggaggct agaaggagag agatgggtgc gagagcgtca gtattaagcg gggagaatt     6960
agatcgcgat gggaaaaaat tcggttaagg ccaggggga  agaaaaaata taaattaaaa    7020
catatagtat gggcaagcag ggagctagaa cgattcgcag ttaatcctgg cctgttagaa    7080
acatcagaag gctgtagaca atactggga  cagctacaac catcccttca gacaggatca    7140
gaagaactta gatcattata taatacagta gcaaccctct attgtgtgca tcaaaggata    7200
gagataaaag acaccaagga agctttagac aagatagagg aagagcaaaa caaaagtaag    7260
accaccgcac agcaagcggc cgctgatctt cagacctgga ggaggagata tgagggacaa    7320
ttggagaagt gaattatata aatataaagt agtaaaaatt gaaccattag gagtagcacc    7380
caccaaggca agagaagag  tggtgcagag agaaaaaaga gcagtgggaa taggagcttt    7440
gttccttggg ttcttgggag cagcaggaag cactatgggc gcagcctcaa tgacgctgac    7500
ggtacaggcc agacaattat tgtctggtat agtgcagcag cagaacaatt tgctgagggc    7560
tattgaggcg caacagcatc tgttgcaact cacagtctgg ggcatcaagc agctccaggc    7620
aagaatcctg gctgtggaaa gatacctaaa ggatcaacag ctcctgggga tttggggttg    7680
ctctggaaaa ctcatttgca ccactgctgt gccttggaat gctagttgga gtaataaatc    7740
tctggaacag atttggaatc acacgacctg gatggagtgg gacagagaaa ttaacaatta    7800
cacaagctta atacactcct taattgaaga atcgcaaaac cagcaagaaa agaatgaaca    7860
agaattattg gaattagata atgggcaag  tttgtggaat tggtttaaca taacaaattg    7920
gctgtggtat ataaaattat tcataatgat agtaggaggc ttggtaggtt taagaatagt    7980
ttttgctgta ctttctatag tgaatagagt taggcaggga tattcaccat tatcgtttca    8040
gacccacctc ccaaccccga ggggacccga caggcccgaa ggaatagaag aagaaggtgg    8100
agagagagac agagacagat ccattcgatt agtgaacgga tctcgacggt atcggttaac    8160
ttttaaaaga aaaggggga  ttggggggta cagtgcaggg gaaagaatag tagacataat    8220
agcaacagac atacaaacta aagaattaca aaaacaaatt acaaaaattc aaaattttat    8280
cgatcacgag actagccg                                                 8298
```

<210> SEQ ID NO 78
<211> LENGTH: 2949
<212> TYPE: DNA
<213> ORGANISM: Artificial Sequence
<220> FEATURE:
<223> OTHER INFORMATION: Synthetic sequence Human BRAF

<400> SEQUENCE: 78

```
cgcctccctt cccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccggaggagg tgtggaatat caaacaaatg attaagttga cacaggaaca     240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgattttc tgtttctagc tctgcatcaa tggataccgt     420
tacatcttct tcctcttcta gcctttcagt gctaccttca tctctttcag ttttcaaaa      480
tcccacagat gtggcacgga gcaaccccaa gtcaccacaa aaacctatcg ttagagtctt     540
cctgcccaac aaacagagga cagtggtacc tgcaaggtgt ggagttacag tccgagacag     600
tctaaagaaa gcactgatga tgagaggtct aatcccagag tgctgtgctg tttacagaat     660
tcaggatgga gagaagaaac caattggttg gacactgat atttcctggc ttactggaga     720
agaattgcat gtggaagtgt tggagaatgt tccacttaca cacacaact ttgtacgaaa      780
aacgttttc accttagcat tttgtgactt ttgtcgaaag ctgcttttcc agggtttccg     840
ctgtcaaaca tgtggttata aatttccaca gcgttgtagt acagaagttc cactgatgtg     900
tgttaattat gaccaacttg atttgctgtt tgtctccaag ttctttgaac accacccaat     960
accacaggaa gaggcgtcct tagcagagac tgccctaaca tctggatcat cccttccgc    1020
acccgcctcg gactctattg gccccaaat tctcaccagt ccgtctcctt caaaatccat    1080
tccaattcca cagcccttcc gaccagcaga tgaagatcat cgaaatcaat ttgggcaacg    1140
agaccgatcc tcatcagctc ccaatgtgca tataaacaca atagaacctg tcaatattga    1200
tgacttgatt agagaccaag gatttcgtgg tgatggagga tcaaccacag gtttgtctgc    1260
taccccccct gcctcattac ctggctcact aactaacgtg aaagccttac agaaatctcc    1320
aggacctcag cgagaaagga agtcatcttc atcctcagaa gacaggaatc gaatgaaaac    1380
acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
tgcacagggc atggattact acacgccaa gtcaatcatc cacagagacc tcaagagtaa    1800
taatatatt cttcatgaag acctcacagt aaaaataggt gattttggtc tagctacagt    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
```

```
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct ttccccaaat tctcgcctct attgagctgc tggcccgctc   2220
attgccaaaa attcaccgca gtgcatcaga accctccttg aatcgggctg gtttccaaac   2280
agaggatttt agtctatatg cttgtgcttc tccaaaaaca cccatccagg caggggata    2340 tggtgcgttt cctgtccact gaaacaaatg agtgagagag ttcaggagag tagcaacaaa   2400
aggaaaataa atgaacatat gtttgcttat atgttaaatt gaataaaata ctctcttttt   2460
ttttaaggtg aaccaaagaa cacttgtgtg gttaaagact agatataatt tttccccaaa   2520
ctaaaattta tacttaacat tggattttta acatccaagg gttaaaatac atagacattg   2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag   2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaaatgtgg atgtctttta tttccttgaa gcaataaact aagtttcttt    2940
ttataaaaa                                                          2949
```

<210> SEQ ID NO 79
<211> LENGTH: 27
<212> TYPE: PRT
<213> ORGANISM: Artificial Sequence
<220> FEATURE:
<223> OTHER INFORMATION: Synthetic sequence AP1M1

<400> SEQUENCE: 79

Val Ile Glu Lys His Ser His Ser Arg Ile Glu Tyr Met Leu Lys Ala
1               5                   10                  15

Lys Ser Gln Phe Lys Arg Arg Ser Thr Ala Asn
            20                  25

<210> SEQ ID NO 80
<211> LENGTH: 20
<212> TYPE: PRT
<213> ORGANISM: Artificial Sequence
<220> FEATURE:
<223> OTHER INFORMATION: Synthetic sequence AP1M1

<400> SEQUENCE: 80

Val Ile Glu Lys His Ser His Ser Arg Ile Glu Tyr Met Leu Lys Ala
1               5                   10                  15

Lys Ser Gln Phe
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic sequence AP1M1

<400> SEQUENCE: 81

Ser Arg Ile Glu Tyr Met Leu Lys Ala Lys Ser Gln Phe Lys Arg Arg
1               5                   10                  15

Ser Thr Ala Asn
            20

```
<210> SEQ ID NO 82
<211> LENGTH: 27
<212> TYPE: PRT
<213> ORGANISM: Artificial Sequence
<220> FEATURE:
<223> OTHER INFORMATION: Synthetic sequence DCAF6

<400> SEQUENCE: 82

Glu Gln Phe Leu Gln Pro Ser Thr Ser Ser Thr Met Ser Thr Gln Ala
1               5                   10                  15

His Ser Thr Ser Ser Pro Thr Glu Ser Pro His
            20                  25

<210> SEQ ID NO 83
<211> LENGTH: 20
<212> TYPE: PRT
<213> ORGANISM: Artificial Sequence
<220> FEATURE:
<223> OTHER INFORMATION: Synthetic sequence DCAF6

<400> SEQUENCE: 83

Glu Gln Phe Leu Gln Pro Ser Thr Ser Ser Thr Met Ser Thr Gln Ala
1               5                   10                  15

His Ser Thr Ser
            20

<210> SEQ ID NO 84
<211> LENGTH: 20
<212> TYPE: PRT
<213> ORGANISM: Artificial Sequence
<220> FEATURE:
<223> OTHER INFORMATION: Synthetic sequence DCAF6

<400> SEQUENCE: 84

Thr Ser Ser Thr Met Ser Thr Gln Ala His Ser Thr Ser Ser Pro Thr
1               5                   10                  15

Glu Ser Pro His
            20

<210> SEQ ID NO 85
<211> LENGTH: 27
<212> TYPE: PRT
<213> ORGANISM: Artificial Sequence
<220> FEATURE:
<223> OTHER INFORMATION: Synthetic sequence GTF2H4

<400> SEQUENCE: 85

Phe Ile Val Val Glu Thr Asn Tyr Arg Leu Tyr Ala Tyr Met Glu Ser
1               5                   10                  15

Glu Leu Gln Ile Ala Leu Ile Ala Leu Phe Ser
            20                  25

<210> SEQ ID NO 86
<211> LENGTH: 20
<212> TYPE: PRT
<213> ORGANISM: Artificial Sequence
<220> FEATURE:
<223> OTHER INFORMATION: Synthetic sequence GTF2H4

<400> SEQUENCE: 86

Phe Ile Val Val Glu Thr Asn Tyr Arg Leu Tyr Ala Tyr Met Glu Ser
1               5                   10                  15

Glu Leu Gln Ile
```

<210> SEQ ID NO 87
<211> LENGTH: 20
<212> TYPE: PRT
<213> ORGANISM: Artificial Sequence
<220> FEATURE:
<223> OTHER INFORMATION: Synthetic sequence GTF2H4

<400> SEQUENCE: 87

Tyr Arg Leu Tyr Ala Tyr Met Glu Ser Glu Leu Gln Ile Ala Leu Ile
1               5                   10                  15

Ala Leu Phe Ser
            20

<210> SEQ ID NO 88
<211> LENGTH: 27
<212> TYPE: PRT
<213> ORGANISM: Artificial Sequence
<220> FEATURE:
<223> OTHER INFORMATION: Synthetic sequence NBPF12

<400> SEQUENCE: 88

Asp Ser Cys Gln Pro Tyr Arg Ser Ser Phe Tyr Ala Leu Gly Glu Lys
1               5                   10                  15

His Val Gly Phe Ser Leu Asp Val Gly Glu Ile
            20                  25

<210> SEQ ID NO 89
<211> LENGTH: 20
<212> TYPE: PRT
<213> ORGANISM: Artificial Sequence
<220> FEATURE:
<223> OTHER INFORMATION: Synthetic sequence NBPF12

<400> SEQUENCE: 89

Asp Ser Cys Gln Pro Tyr Arg Ser Ser Phe Tyr Ala Leu Gly Glu Lys
1               5                   10                  15

His Val Gly Phe
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic sequence NBPF12

<400> SEQUENCE: 90

Ser Ser Phe Tyr Ala Leu Gly Glu Lys His Val Gly Phe Ser Leu Asp
1               5                   10                  15

Val Gly Glu Ile
            20

<210> SEQ ID NO 91
<211> LENGTH: 27
<212> TYPE: PRT
<213> ORGANISM: Artificial Sequence
<220> FEATURE:
<223> OTHER INFORMATION: Synthetic sequence ORC3

<400> SEQUENCE: 91

Glu Ser Phe Ala Thr Lys Val Leu Gln Asp Phe Ile Ile Leu Ser Ser
1               5                   10                  15

```
Gln His Leu His Glu Phe Pro Leu Ile Leu Ile
        20                  25

<210> SEQ ID NO 92
<211> LENGTH: 20
<212> TYPE: PRT
<213> ORGANISM: Artificial Sequence
<220> FEATURE:
<223> OTHER INFORMATION: Synthetic sequence ORC3

<400> SEQUENCE: 92

Glu Ser Phe Ala Thr Lys Val Leu Gln Asp Phe Ile Ile Leu Ser Ser
1               5                   10                  15

Gln His Leu His
        20

<210> SEQ ID NO 93
<211> LENGTH: 20
<212> TYPE: PRT
<213> ORGANISM: Artificial Sequence
<220> FEATURE:
<223> OTHER INFORMATION: Synthetic sequence ORC3

<400> SEQUENCE: 93

Leu Gln Asp Phe Ile Ile Leu Ser Ser Gln His Leu His Glu Phe Pro
1               5                   10                  15

Leu Ile Leu Ile
        20

<210> SEQ ID NO 94
<211> LENGTH: 27
<212> TYPE: PRT
<213> ORGANISM: Artificial Sequence
<220> FEATURE:
<223> OTHER INFORMATION: Synthetic sequence ROR1

<400> SEQUENCE: 94

Leu Val Pro Thr Ser Ser Trp Asn Ile Ser Ser Glu Leu Ser Lys Asp
1               5                   10                  15

Ser Tyr Leu Thr Leu Asp Glu Pro Met Asn Asn
        20                  25

<210> SEQ ID NO 95
<211> LENGTH: 20
<212> TYPE: PRT
<213> ORGANISM: Artificial Sequence
<220> FEATURE:
<223> OTHER INFORMATION: Synthetic sequence ROR1

<400> SEQUENCE: 95

Leu Val Pro Thr Ser Ser Trp Asn Ile Ser Ser Glu Leu Ser Lys Asp
1               5                   10                  15

Ser Tyr Leu Thr
        20

<210> SEQ ID NO 96
<211> LENGTH: 20
<212> TYPE: PRT
<213> ORGANISM: Artificial Sequence
<220> FEATURE:
<223> OTHER INFORMATION: Synthetic sequence ROR1

<400> SEQUENCE: 96

Asn Ile Ser Ser Glu Leu Ser Lys Asp Ser Tyr Leu Thr Leu Asp Glu
1               5                   10                  15
```

```
Pro Met Asn Asn
            20

<210> SEQ ID NO 97
<211> LENGTH: 27
<212> TYPE: PRT
<213> ORGANISM: Artificial Sequence
<220> FEATURE:
<223> OTHER INFORMATION: Synthetic sequence SF3B1

<400> SEQUENCE: 97

Gln Met Gly Gly Ser Thr Pro Val Leu Thr Pro Gly Lys Ala Pro Ile
1               5                   10                  15

Gly Thr Pro Ala Met Asn Met Ala Thr Pro Thr
            20                  25

<210> SEQ ID NO 98
<211> LENGTH: 20
<212> TYPE: PRT
<213> ORGANISM: Artificial Sequence
<220> FEATURE:
<223> OTHER INFORMATION: Synthetic sequence SF3B1

<400> SEQUENCE: 98

Gln Met Gly Gly Ser Thr Pro Val Leu Thr Pro Gly Lys Ala Pro Ile
1               5                   10                  15

Gly Thr Pro Ala
            20

<210> SEQ ID NO 99
<211> LENGTH: 20
<212> TYPE: PRT
<213> ORGANISM: Artificial Sequence
<220> FEATURE:
<223> OTHER INFORMATION: Synthetic sequence SF3B1

<400> SEQUENCE: 99

Val Leu Thr Pro Gly Lys Ala Pro Ile Gly Thr Pro Ala Met Asn Met
1               5                   10                  15

Ala Thr Pro Thr
            20

<210> SEQ ID NO 100
<211> LENGTH: 27
<212> TYPE: PRT
<213> ORGANISM: Artificial Sequence
<220> FEATURE:
<223> OTHER INFORMATION: Synthetic sequence UNKL

<400> SEQUENCE: 100

Ala His Gly Pro Leu Asp Leu Arg Pro Pro Val Cys Asp Ile Arg Glu
1               5                   10                  15

Leu Gln Ala Gln Glu Ala Leu Gln Asn Gly Gln
            20                  25

<210> SEQ ID NO 101
<211> LENGTH: 20
<212> TYPE: PRT
<213> ORGANISM: Artificial Sequence
<220> FEATURE:
<223> OTHER INFORMATION: Synthetic sequence UNKL

<400> SEQUENCE: 101

Ala His Gly Pro Leu Asp Leu Arg Pro Pro Val Cys Asp Ile Arg Glu
```

```
                1               5                  10                  15

Leu Gln Ala Gln
            20

<210> SEQ ID NO 102
<211> LENGTH: 20
<212> TYPE: PRT
<213> ORGANISM: Artificial Sequence
<220> FEATURE:
<223> OTHER INFORMATION: Synthetic sequence UNKL

<400> SEQUENCE: 102

Arg Pro Pro Val Cys Asp Ile Arg Glu Leu Gln Ala Gln Glu Ala Leu
1               5                   10                  15

Gln Asn Gly Gln
            20

<210> SEQ ID NO 103
<211> LENGTH: 27
<212> TYPE: PRT
<213> ORGANISM: Artificial Sequence
<220> FEATURE:
<223> OTHER INFORMATION: Synthetic sequence ZNF700

<400> SEQUENCE: 103

Gly Glu Lys Pro Tyr Glu Cys Ser Lys Cys Asp Lys Ala Leu His Ser
1               5                   10                  15

Ser Ser Ser Tyr His Arg His Glu Arg Ser His
            20                  25

<210> SEQ ID NO 104
<211> LENGTH: 20
<212> TYPE: PRT
<213> ORGANISM: Artificial Sequence
<220> FEATURE:
<223> OTHER INFORMATION: Synthetic sequence ZNF700

<400> SEQUENCE: 104

Gly Glu Lys Pro Tyr Glu Cys Ser Lys Cys Asp Lys Ala Leu His Ser
1               5                   10                  15

Ser Ser Ser Tyr
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic sequence ZNF700

<400> SEQUENCE: 105

Ser Lys Cys Asp Lys Ala Leu His Ser Ser Ser Tyr His Arg His
1               5                   10                  15

Glu Arg Ser His
            20

<210> SEQ ID NO 106
<211> LENGTH: 27
<212> TYPE: PRT
<213> ORGANISM: Artificial Sequence
<220> FEATURE:
<223> OTHER INFORMATION: Synthetic sequence NVL

<400> SEQUENCE: 106
```

```
Ala Pro Cys Ile Ile Phe Ile Asp Glu Ile Asp Ala Ile Pro Pro Lys
1               5                   10                  15

Arg Glu Val Ala Ser Lys Asp Met Glu Arg Arg
            20                  25
```

<210> SEQ ID NO 107
<211> LENGTH: 20
<212> TYPE: PRT
<213> ORGANISM: Artificial Sequence
<220> FEATURE:
<223> OTHER INFORMATION: Synthetic sequence NVL

<400> SEQUENCE: 107

```
Ala Pro Cys Ile Ile Phe Ile Asp Glu Ile Asp Ala Ile Pro Pro Lys
1               5                   10                  15

Arg Glu Val Ala
            20
```

<210> SEQ ID NO 108
<211> LENGTH: 20
<212> TYPE: PRT
<213> ORGANISM: Artificial Sequence
<220> FEATURE:
<223> OTHER INFORMATION: Synthetic sequence NVL

<400> SEQUENCE: 108

```
Asp Glu Ile Asp Ala Ile Pro Pro Lys Arg Glu Val Ala Ser Lys Asp
1               5                   10                  15

Met Glu Arg Arg
            20
```

<210> SEQ ID NO 109
<211> LENGTH: 27
<212> TYPE: PRT
<213> ORGANISM: Artificial Sequence
<220> FEATURE:
<223> OTHER INFORMATION: Synthetic sequence MATN1

<400> SEQUENCE: 109

```
Ser Arg Ser Pro Asp Ile Ser Lys Val Val Ile Val Val Pro Asp Gly
1               5                   10                  15

Arg Pro Gln Asp Ser Val Gln Asp Val Ser Ala
            20                  25
```

<210> SEQ ID NO 110
<211> LENGTH: 20
<212> TYPE: PRT
<213> ORGANISM: Artificial Sequence
<220> FEATURE:
<223> OTHER INFORMATION: Synthetic sequence MATN1

<400> SEQUENCE: 110

```
Ser Arg Ser Pro Asp Ile Ser Lys Val Val Ile Val Val Pro Asp Gly
1               5                   10                  15

Arg Pro Gln Asp
            20
```

<210> SEQ ID NO 111
<211> LENGTH: 20
<212> TYPE: PRT
<213> ORGANISM: Artificial Sequence
<220> FEATURE:
<223> OTHER INFORMATION: Synthetic sequence MATN1

<400> SEQUENCE: 111

-continued

```
Lys Val Val Ile Val Val Pro Asp Gly Arg Pro Gln Asp Ser Val Gln
1               5                   10                  15

Asp Val Ser Ala
            20

<210> SEQ ID NO 112
<211> LENGTH: 27
<212> TYPE: PRT
<213> ORGANISM: Artificial Sequence
<220> FEATURE:
<223> OTHER INFORMATION: Synthetic sequence CTNNA2

<400> SEQUENCE: 112

Val Arg Gln Ala Leu Gln Asp Leu Leu Ser Glu Tyr Met His Asn Thr
1               5                   10                  15

Gly Arg Lys Glu Lys Gly Asp Pro Leu Asn Ile
            20                  25

<210> SEQ ID NO 113
<211> LENGTH: 20
<212> TYPE: PRT
<213> ORGANISM: Artificial Sequence
<220> FEATURE:
<223> OTHER INFORMATION: Synthetic sequence CTNNA2

<400> SEQUENCE: 113

Val Arg Gln Ala Leu Gln Asp Leu Leu Ser Glu Tyr Met His Asn Thr
1               5                   10                  15

Gly Arg Lys Glu
            20

<210> SEQ ID NO 114
<211> LENGTH: 20
<212> TYPE: PRT
<213> ORGANISM: Artificial Sequence
<220> FEATURE:
<223> OTHER INFORMATION: Synthetic sequence CTNNA2

<400> SEQUENCE: 114

Leu Leu Ser Glu Tyr Met His Asn Thr Gly Arg Lys Glu Lys Gly Asp
1               5                   10                  15

Pro Leu Asn Ile
            20

<210> SEQ ID NO 115
<211> LENGTH: 27
<212> TYPE: PRT
<213> ORGANISM: Artificial Sequence
<220> FEATURE:
<223> OTHER INFORMATION: Synthetic sequence GET4

<400> SEQUENCE: 115

Arg Tyr Met Ser Gln Ser Lys His Thr Glu Ala Arg Glu Arg Met Tyr
1               5                   10                  15

Ser Gly Ala Leu Leu Phe Phe Ser His Gly Gln
            20                  25

<210> SEQ ID NO 116
<211> LENGTH: 20
<212> TYPE: PRT
<213> ORGANISM: Artificial Sequence
<220> FEATURE:
<223> OTHER INFORMATION: Synthetic sequence GET4
```

```
<400> SEQUENCE: 116

Arg Tyr Met Ser Gln Ser Lys His Thr Glu Ala Arg Glu Arg Met Tyr
1               5                   10                  15

Ser Gly Ala Leu
            20

<210> SEQ ID NO 117
<211> LENGTH: 20
<212> TYPE: PRT
<213> ORGANISM: Artificial Sequence
<220> FEATURE:
<223> OTHER INFORMATION: Synthetic sequence GET4

<400> SEQUENCE: 117

His Thr Glu Ala Arg Glu Arg Met Tyr Ser Gly Ala Leu Leu Phe Phe
1               5                   10                  15

Ser His Gly Gln
            20

<210> SEQ ID NO 118
<211> LENGTH: 27
<212> TYPE: PRT
<213> ORGANISM: Artificial Sequence
<220> FEATURE:
<223> OTHER INFORMATION: Synthetic sequence NTNG1

<400> SEQUENCE: 118

Thr Val Thr Asp Leu Arg Ile Arg Leu Leu Arg Pro Ala Ile Gly Glu
1               5                   10                  15

Ile Phe Val Asp Glu Leu His Leu Ala Arg Tyr
            20                  25

<210> SEQ ID NO 119
<211> LENGTH: 20
<212> TYPE: PRT
<213> ORGANISM: Artificial Sequence
<220> FEATURE:
<223> OTHER INFORMATION: Synthetic sequence NTNG1

<400> SEQUENCE: 119

Thr Val Thr Asp Leu Arg Ile Arg Leu Leu Arg Pro Ala Ile Gly Glu
1               5                   10                  15

Ile Phe Val Asp
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic sequence NTNG1

<400> SEQUENCE: 120

Arg Leu Leu Arg Pro Ala Ile Gly Glu Ile Phe Val Asp Glu Leu His
1               5                   10                  15

Leu Ala Arg Tyr
            20

<210> SEQ ID NO 121
<211> LENGTH: 27
<212> TYPE: PRT
<213> ORGANISM: Artificial Sequence
<220> FEATURE:
<223> OTHER INFORMATION: Synthetic sequence SPTBN5
```

<400> SEQUENCE: 121

Thr Leu Leu Leu Asp Ala Trp Leu Thr Thr Lys Ala Ala Ile Ala Glu
1               5                   10                  15

Ser Gln Asp Tyr Gly Gln Asp Leu Glu Gly Val
            20                  25

<210> SEQ ID NO 122
<211> LENGTH: 20
<212> TYPE: PRT
<213> ORGANISM: Artificial Sequence
<220> FEATURE:
<223> OTHER INFORMATION: Synthetic sequence SPTBN5

<400> SEQUENCE: 122

Thr Leu Leu Leu Asp Ala Trp Leu Thr Thr Lys Ala Ala Ile Ala Glu
1               5                   10                  15

Ser Gln Asp Tyr
            20

<210> SEQ ID NO 123
<211> LENGTH: 20
<212> TYPE: PRT
<213> ORGANISM: Artificial Sequence
<220> FEATURE:
<223> OTHER INFORMATION: Synthetic sequence SPTBN5

<400> SEQUENCE: 123

Leu Thr Thr Lys Ala Ala Ile Ala Glu Ser Gln Asp Tyr Gly Gln Asp
1               5                   10                  15

Leu Glu Gly Val
            20

<210> SEQ ID NO 124
<211> LENGTH: 27
<212> TYPE: PRT
<213> ORGANISM: Artificial Sequence
<220> FEATURE:
<223> OTHER INFORMATION: Synthetic sequence DPP6

<400> SEQUENCE: 124

Leu Leu Val Ile Leu Val Ile Cys Ser Leu Ile Val Thr Leu Val Ile
1               5                   10                  15

Leu Leu Thr Pro Ala Glu Asp Asn Ser Leu Ser
            20                  25

<210> SEQ ID NO 125
<211> LENGTH: 20
<212> TYPE: PRT
<213> ORGANISM: Artificial Sequence
<220> FEATURE:
<223> OTHER INFORMATION: Synthetic sequence DPP6

<400> SEQUENCE: 125

Leu Leu Val Ile Leu Val Ile Cys Ser Leu Ile Val Thr Leu Val Ile
1               5                   10                  15

Leu Leu Thr Pro
            20

<210> SEQ ID NO 126
<211> LENGTH: 20
<212> TYPE: PRT
<213> ORGANISM: Artificial Sequence
<220> FEATURE:

<223> OTHER INFORMATION: Synthetic sequence DPP6

<400> SEQUENCE: 126

Cys Ser Leu Ile Val Thr Leu Val Ile Leu Thr Pro Ala Glu Asp
1               5                   10                  15

Asn Ser Leu Ser
            20

<210> SEQ ID NO 127
<211> LENGTH: 27
<212> TYPE: PRT
<213> ORGANISM: Artificial Sequence
<220> FEATURE:
<223> OTHER INFORMATION: Synthetic sequence HIAT1

<400> SEQUENCE: 127

Val Lys Gly Leu Leu Ser Phe Leu Ser Ala Pro Leu Ile Cys Ala Leu
1               5                   10                  15

Ser Asp Val Trp Gly Arg Lys Ser Phe Leu Leu
            20                  25

<210> SEQ ID NO 128
<211> LENGTH: 20
<212> TYPE: PRT
<213> ORGANISM: Artificial Sequence
<220> FEATURE:
<223> OTHER INFORMATION: Synthetic sequence HIAT1

<400> SEQUENCE: 128

Val Lys Gly Leu Leu Ser Phe Leu Ser Ala Pro Leu Ile Cys Ala Leu
1               5                   10                  15

Ser Asp Val Trp
            20

<210> SEQ ID NO 129
<211> LENGTH: 20
<212> TYPE: PRT
<213> ORGANISM: Artificial Sequence
<220> FEATURE:
<223> OTHER INFORMATION: Synthetic sequence HIAT1

<400> SEQUENCE: 129

Leu Ser Ala Pro Leu Ile Cys Ala Leu Ser Asp Val Trp Gly Arg Lys
1               5                   10                  15

Ser Phe Leu Leu
            20

<210> SEQ ID NO 130
<211> LENGTH: 27
<212> TYPE: PRT
<213> ORGANISM: Artificial Sequence
<220> FEATURE:
<223> OTHER INFORMATION: Synthetic sequence ITGA4

<400> SEQUENCE: 130

Gly Ser Gly Ala Val Met Asn Ala Met Glu Thr Asn Leu Phe Gly Ser
1               5                   10                  15

Asp Lys Tyr Ala Ala Arg Phe Gly Glu Ser Ile
            20                  25

<210> SEQ ID NO 131
<211> LENGTH: 20
<212> TYPE: PRT
<213> ORGANISM: Artificial Sequence

```
<220> FEATURE:
<223> OTHER INFORMATION: Synthetic sequence ITGA4

<400> SEQUENCE: 131

Gly Ser Gly Ala Val Met Asn Ala Met Glu Thr Asn Leu Phe Gly Ser
1               5                   10                  15

Asp Lys Tyr Ala
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic sequence ITGA4

<400> SEQUENCE: 132

Ala Met Glu Thr Asn Leu Phe Gly Ser Asp Lys Tyr Ala Ala Arg Phe
1               5                   10                  15

Gly Glu Ser Ile
            20

<210> SEQ ID NO 133
<211> LENGTH: 27
<212> TYPE: PRT
<213> ORGANISM: Artificial Sequence
<220> FEATURE:
<223> OTHER INFORMATION: Synthetic sequence MYO1A

<400> SEQUENCE: 133

Ser Val Arg Phe Lys Glu Asn Ser Val Ala Val Lys Val Ile Gln Gly
1               5                   10                  15

Pro Ala Gly Gly Asp Asn Ser Lys Leu Arg Tyr
            20                  25

<210> SEQ ID NO 134
<211> LENGTH: 20
<212> TYPE: PRT
<213> ORGANISM: Artificial Sequence
<220> FEATURE:
<223> OTHER INFORMATION: Synthetic sequence MYO1A

<400> SEQUENCE: 134

Ser Val Arg Phe Lys Glu Asn Ser Val Ala Val Lys Val Ile Gln Gly
1               5                   10                  15

Pro Ala Gly Gly
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic sequence MYO1A

<400> SEQUENCE: 135

Ser Val Ala Val Lys Val Ile Gln Gly Pro Ala Gly Gly Asp Asn Ser
1               5                   10                  15

Lys Leu Arg Tyr
            20

<210> SEQ ID NO 136
<211> LENGTH: 20
<212> TYPE: DNA
```

```
<213> ORGANISM: Artificial Sequence
<220> FEATURE:
<223> OTHER INFORMATION: Synthetic sequence TRAC-gRNA-1

<400> SEQUENCE: 136
agagtctctc agctggtaca                                                     20

<210> SEQ ID NO 137
<211> LENGTH: 20
<212> TYPE: DNA
<213> ORGANISM: Artificial Sequence
<220> FEATURE:
<223> OTHER INFORMATION: Synthetic sequenceTRAC-gRNA-2

<400> SEQUENCE: 137
tgtgctagac atgaggtcta                                                     20

<210> SEQ ID NO 138
<211> LENGTH: 20
<212> TYPE: DNA
<213> ORGANISM: Artificial Sequence
<220> FEATURE:
<223> OTHER INFORMATION: Synthetic sequence TRBC-gRNA-1

<400> SEQUENCE: 138
gcagtatctg gagtcattga                                                     20

<210> SEQ ID NO 139
<211> LENGTH: 20
<212> TYPE: DNA
<213> ORGANISM: Artificial Sequence
<220> FEATURE:
<223> OTHER INFORMATION: Synthetic sequence TRBC-gRNA-2

<400> SEQUENCE: 139
ggagaatgac gagtggaccc                                                     20

<210> SEQ ID NO 140
<211> LENGTH: 20
<212> TYPE: DNA
<213> ORGANISM: Artificial Sequence
<220> FEATURE:
<223> OTHER INFORMATION: Synthetic sequence B2M-gRNA

<400> SEQUENCE: 140
cgcgagcaca gctaaggcca                                                     20

<210> SEQ ID NO 141
<211> LENGTH: 20
<212> TYPE: DNA
<213> ORGANISM: Artificial Sequence
<220> FEATURE:
<223> OTHER INFORMATION: Synthetic sequence PD-1-gRNA

<400> SEQUENCE: 141
ggccaggatg gttcttaggt                                                     20

<210> SEQ ID NO 142
<211> LENGTH: 25
<212> TYPE: DNA
<213> ORGANISM: Artificial Sequence
<220> FEATURE:
<223> OTHER INFORMATION: Synthetic sequence sgRNA Forward Oligo:
      TRAC_sgRNA_pLenti_F1

<400> SEQUENCE: 142
```
caccggagaa tcaaaatcgg tgaat                                              25

<210> SEQ ID NO 143
<211> LENGTH: 25
<212> TYPE: DNA
<213> ORGANISM: Artificial Sequence
<220> FEATURE:
<223> OTHER INFORMATION: Synthetic sequence sgRNA Reverse Oligo:
      TRAC_sgRNA_pLenti_R1

<400> SEQUENCE: 143
aaacattcac cgattttgat tctcc                                              25

<210> SEQ ID NO 144
<211> LENGTH: 24
<212> TYPE: DNA
<213> ORGANISM: Artificial Sequence
<220> FEATURE:
<223> OTHER INFORMATION: Synthetic sequence PD1_sgRNA_F1

<400> SEQUENCE: 144
caccgcagtt gtgtgacacg gaag                                               24

<210> SEQ ID NO 145
<211> LENGTH: 24
<212> TYPE: DNA
<213> ORGANISM: Artificial Sequence
<220> FEATURE:
<223> OTHER INFORMATION: Synthetic sequence PD1_sgRNA_R1

<400> SEQUENCE: 145
aaaccttccg tgtcacacaa ctgc                                               24

<210> SEQ ID NO 146
<211> LENGTH: 25
<212> TYPE: DNA
<213> ORGANISM: Artificial Sequence
<220> FEATURE:
<223> OTHER INFORMATION: Synthetic sequence CTLA4_sgRNA_F1

<400> SEQUENCE: 146
caccggcaaa ggtgagtgag acttt                                              25

<210> SEQ ID NO 147
<211> LENGTH: 25
<212> TYPE: DNA
<213> ORGANISM: Artificial Sequence
<220> FEATURE:
<223> OTHER INFORMATION: Synthetic sequence CTLA4_sgRNA_R1

<400> SEQUENCE: 147
aaacaaagtc tcactcacct ttgcc                                              25

<210> SEQ ID NO 148
<211> LENGTH: 25
<212> TYPE: DNA
<213> ORGANISM: Artificial Sequence
<220> FEATURE:
<223> OTHER INFORMATION: Synthetic sequence LAG3_sgRNA_F1

<400> SEQUENCE: 148
caccggtttc tgcagccgct ttggg                                              25

<210> SEQ ID NO 149
<211> LENGTH: 25
<212> TYPE: DNA

```
<213> ORGANISM: Artificial Sequence
<220> FEATURE:
<223> OTHER INFORMATION: Synthetic sequence LAG3_sgRNA_R1

<400> SEQUENCE: 149
aaaccccaaa gcggctgcag aaacc                                         25
```

BRAF-SPECIFIC TCRS AND USES THEREOF

STATEMENT OF GOVERNMENT INTEREST

This invention was made with government support under CA015704 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_454USPC_SEQUENCE_LISTING.txt. The text file is 126 KB, was created on Aug. 9, 2020, and is being submitted electronically via EFS-Web.

BACKGROUND

Adoptive transfer of tumor-specific T cells is an appealing strategy to eliminate existing tumors and requires the establishment of a robust population of antigen-specific T cells in vivo to eliminate existing tumor and prevent recurrences (Stromnes et al., *Immunol. Rev.* 257:145, 2014). In recent years, there is increasing evidence that immune responses to antigens created by mutations in cancer can be recognized by T cells and that these T cells can mediate clinical responses to treatment with adoptive cell therapy and immune checkpoint inhibitors. Antigens that arise from such mutations are particularly appealing targets for immunotherapies due to being completely specific for the cancer relative to normal tissue, and also because they lack central tolerance mechanisms that could limit T cell function against other antigen types.

However, although administration of autologous or engineered allogeneic tumor-specific CD8$^+$ cytotoxic T lymphocytes (CTLs) can mediate direct anti-tumor activity in select patients (Chapuis et al., *Cancer Res.* 72:LB-136, 2012; Chapuis et al., *Sci. Transl. Med.* 5:174ra127, 2013; Chapuis et al., *Proc. Nat'l. Acad. Sci. U.S.A.* 109:4592, 2012)$^{2-4}$, identifying and isolating tumor-reactive T cells with desired characteristics is a laborious and complex endeavor (see Stone and Kranz, *Frontiers Immunol.* 4:244, 2013; Chapuis et al., 2013; Schmitt et al., *Hum. Gene Ther.* 20:1240, 2009; Ho et al., *J. Immunol. Methods* 310:40, 2006). Further, the variability in the avidity of the CTLs isolated from each patient or donor limits the anti-tumor efficacy in clinical trials (Chapuis et al., 2013). Moreover, most antigen-specific mutations that lead to immune responses are found only in the cancer of one individual, and not in multiple patients.

There is a clear need for alternative antigen-specific TCR immunotherapies directed against various cancers, such as hairy cell leukemia, malignant melanoma, thyroid, lung, and colon cancers. In particular, TCR immunotherapies targeting antigens that are both cancer-specific and widely prevalent in cancers are needed. Presently disclosed embodiments address these needs and provide other related advantages.

DETAILED DESCRIPTION

Figure 1A:
FIGS. 1A-1I show the identification and characterization of patient-derived CD4$^+$ T cells specific for BRAF$^{V600E}$. (1A) Positron emission tomography showing recurrent tumor in left iliac region (left) and left thigh (right). (1B-1D) Specificity and HLA restriction of BRAF$^{V600E}$-specific T cells: (1B) IFN-γ production by the patient-derived T cell line incubated with autologous B cells pulsed with wildtype and mutant BRAF peptide; (1C) recognition of autologous B cells pulsed with mutant BRAF peptide or transfected with mRNA encoding mutant or wildtype BRAF sequences; (1D) recognition of autologous B cells pulsed with mutant BRAF peptide in the presence or absence of HLA blocking antibodies. (1E) Recognition by BRAF$^{V600E}$-specific CD4$^+$ T cells of the B-LCL line 1331, which is matched at HLA-DQ with the patient, and the HLA-mismatched B-LCL line VAVY, prior to and after transduction with HLA-DRB1*0404 (DR4) or HLA-DQB1*0302/DQA1*03 (DQ3). (1F) IFN-γ release by patient-derived BRAF$^{V600E}$-specific T cells incubated with allogeneic B-LCL cell lines expressing HLA DQB1*03 alleles and pulsed with the indicated amount of 21-mer BRAF$^{V600E}$ peptide. Three technical replicates were performed. (1G) IFN-γ release by patient-derived BRAF$^{V600E}$-specific T cells incubated with autologous B cells pulsed with BRAF$^{V600E}$ peptide or the indicated tumor cell lines with and without pretreatment with human IFN-γ 500 U/ml for 3 days. (1H, 1I) Expression (mean fluorescence intensity) of HLA-DQ (1H) and HLA-DR (1I) on tumor cell lines with and without IFN-γ pretreatment, quantitated by flow cytometry relative to the isotype control. Experiments were performed in technical duplicate or triplicate as indicated, and are representative of two independent experiments.
Figure 1A:

In certain aspects, the present disclosure provides binding proteins, such as T cell receptors (TCRs), that are capable of specifically binding to a $BRAF^{V600E}$ peptide antigen, such as a $BRAF^{V600E}$ peptide antigen associated with a major histocompatibility complex (MHC) (e.g., human leukocyte antigen, HLA). Binding proteins of this disclosure are useful in, for example, therapies to treat hyperproliferative diseases, such as cancer, characterized by $BRAF^{V600E}$ expression.

By way of background, antigens created by cancer-associated mutations are appealing targets for therapeutic intervention, but are generally unique to an individual patient. Thus, antigens caused by essential "driver" mutations of cancer are of interest since they are both specific to cancer cells and occur at high frequencies in patient populations. BRAF protein is involved in cell growth signaling, while mutant BRAF is implicated in a number of cancers (see, e.g., Frasca et al., *Endocrine-Related Cancer* 15:191(2008)). In particular, the substitution mutation V600E ($BRAF^{V600E}$) arising in exon 15 of the BRAF gene, activates BRAF to drive a growth signaling pathway that is an early event in carcinogenesis. This mutation is found in all instances of hairy cell leukemia, about half of malignant melanoma cases, and significant numbers of patients with advanced thyroid, lung and colon cancer.

The compositions and methods described herein will in certain embodiments have therapeutic utility for the treatment of diseases and conditions associated with $BRAF^{V600E}$ expression. Such diseases include various forms of hyperproliferative disorders, such as hairy cell leukemia, melanoma, thyroid cancers including poorly differentiated thyroid cancer, non-small cell lung cancer, colorectal cancer, papillary cancer, non-Hodgkin lymphoma, glioblastoma, and pilocytic astrocytoma, breast cancer, ovarian cancer, Langerhans cell histiocytosis, and sarcomas (e.g., fibrosarcoma (fibroblastic sarcoma), Dermatofibrosarcoma protuberans (DFSP), osteosarcoma, rhabdomyosarcoma, Ewing's sarcoma, a gastrointestinal stromal tumor, Leiomyosarcoma; angiosarcoma (vascular sarcoma), Kaposi's sarcoma, liposarcoma, pleomorphic sarcoma, and synovial sarcoma). Non-limiting examples of these and related uses are described herein and include in vitro, ex vivo and in vivo stimulation of $BRAF^{V600E}$ antigen-specific T cell responses, such as by the use of recombinant T cells expressing TCR specific for a $BRAF^{V600E}$ peptide.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" is not equivalent to "comprising," and refers to the specified materials or steps of a claimed invention, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells, including Natural Killer T (NK-T) cells). Exemplary immune system cells include a $CD4^+$ T cell, a $CD8^+$ T cell, a $CD4^-$ $CD8^-$ double negative T cell, a γδ T cell, a regulatory T cell, a natural killer cell, a natural killer T cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

"Major histocompatibility complex" (MHC) refers to glycoproteins that deliver peptide antigens to a cell surface. MHC class I molecules are heterodimers having a membrane spanning α chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by $CD8^+$ T cells. MHC class II molecules deliver peptides originating in the vesicular system to the cell surface, where a peptide:MHC complex is recognized by $CD4^+$ T cells. Human MHC is referred to as human leukocyte antigen (HLA). HLA-II types include DP, DM, DOA, DOB, DQ, and DR. Numerous alleles encoding the subunits of the various HLA types are known, including, for example, HLA-DQA1*03, HLA-DQB1*0301, HLA-DQB1*0302, HLA-DQB1*0303. In certain embodiments, a binding protein according to the present disclosure is capable of recognizing a $BRAF^{V600E}$ peptide complexed with HLA-DQ. In certain embodiments, the HLA complex comprises HLA-DQB1*0301, *0302, or *0303. In certain embodiments, the HLA complex comprises HLA-DQB1*0302. In further embodiments, the HLA complex comprises HLA-DQA1*03.

A "T cell" or "T lymphocyte" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of: central memory T cells ($T_{CM}$, increased expression of CD62L, CCR7, CD28, CD127, CD45RO, and CD95, and decreased expression of CD54RA as compared to naïve T cells); and effector memory T cells ($T_{EM}$, decreased expression of CD62L, CCR7, CD28, CD45RA, and increased expression of CD127 as compared to naïve T cells or $T_{CM}$).

Effector T cells ($T_E$) refers to antigen-experienced $CD8^+$ cytotoxic T lymphocytes that have decreased expression of CD62L, CCR7, CD28, and are positive for granzyme and perforin as compared to $T_{CM}$. Helper T cells ($T_H$) are $CD4^+$ cells that influence the activity of other immune cells by releasing cytokines. $CD4^+$ T cells can activate and suppress an adaptive immune response, and which of those two functions is induced will depend on presence of other cells and signals. T cells can be collected using known techniques, and the various subpopulations or combinations thereof can be enriched or depleted by known techniques, such as by affinity binding to antibodies, flow cytometry, or immunomagnetic selection. Other exemplary T cells include regulatory T cells, such as $CD4^+$ $CD25^+$ ($Foxp3^+$) regulatory T cells and Treg17 cells, as well as Tr1, Th3, $CD8^+$ $CD28^-$, and Qa-1 restricted T cells.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease*, $3^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). Like immunoglobulins, the extracellular portion of TCR chains (e.g., α-chain, β-chain) contain two immunoglobulin domains: a variable domain (e.g., α-chain variable domain or $V_α$, β-chain variable domain or $V_β$; typically amino acids 1 to 116 based on Kabat numbering (Kabat et al., "Sequences of Proteins of Immunological Interest, US Dept. Health and Human Services, Public Health Service National Institutes of Health, 1991, $5^{th}$ ed.)) at the N-terminus; and one constant domain (e.g., α-chain constant domain or $C_α$, typically amino acids 117 to 259 based on Kabat, β-chain constant domain or $C_β$, typically amino acids 117 to 295 based on Kabat) adjacent to the cell membrane. Also, like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). TCR variable domain sequences can be aligned to a numbering scheme (e.g., Kabat, EU, International Immunogenetics Information System (IMGT) and Aho), which can allow equivalent residue positions to be annotated and for different molecules to be compared using Antigen receptor Numbering And Receptor Classification (ANARCI) software tool (2016, Bioinformatics 15:298-300). A numbering scheme provides a standardized delineation of framework regions and CDRs in the TCR variable domains.

In certain embodiments, a TCR is found on the surface of T cells (or T lymphocytes) and associates with the CD3 complex. The source of a TCR as used in the present disclosure may be from various animal species, such as a human, mouse, rat, rabbit or other mammal.

"CD3" is known in the art as a multi-protein complex of six chains (see, Abbas and Lichtman, 2003; Janeway et al., p. 172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three ITAMs. Without wishing to be bound by theory, it is believed that the ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

"CD4" refers to an immunoglobulin co-receptor glycoprotein that assists the TCR in communicating with antigen-presenting cells (see, Campbell & Reece, *Biology* 909 (Benjamin Cummings, Sixth Ed., 2002); UniProtKB P01730). CD4 is found on the surface of immune cells such as T helper cells, monocytes, macrophages, and dendritic cells, and includes four immunoglobulin domains (D1 to D4) that are expressed at the cell surface. During antigen presentation, CD4 is recruited, along with the TCR complex, to bind to different regions of the MHCII molecule (CD4 binds MHCII β2, while the TCR complex binds MHCII α1/β1). Without wishing to be bound by theory, it is believed that close proximity to the TCR complex allows CD4-associated kinase molecules to phosphorylate the immunoreceptor tyrosine activation motifs (ITAMs) present on the cytoplasmic domains of CD3. This activity is thought to amplify the signal generated by the activated TCR in order to produce various types of T helper cells.

As used herein, the term "CD8 co-receptor" or "CD8" means the cell surface glycoprotein CD8, either as an alpha-alpha homodimer or an alpha-beta heterodimer. The CD8 co-receptor assists in the function of cytotoxic T cells (CD8+) and functions through signaling via its cytoplasmic tyrosine phosphorylation pathway (Gao and Jakobsen, *Immunol. Today* 21:630-636, 2000; Cole and Gao, *Cell. Mol. Immunol.* 1:81-88, 2004). In humans, there are five (5) different CD8 beta chains (see UniProtKB identifier P10966) and a single CD8 alpha chain (see UniProtKB identifier P01732)

The term "variable region" or "variable domain" refers to the domain of a TCR α-chain or β-chain (or γ-chain and δ-chain for γδ TCRs) that is involved in binding of the TCR to antigen. The variable domains of the α-chain and β-chain (Vα and Vβ, respectively) of a native TCR generally have similar structures, with each domain comprising four generally conserved framework regions (FRs) and three CDRs. The Vα domain is encoded by two separate DNA segments, the variable gene segment and the joining gene segment (V-J); the Vβ domain is encoded by three separate DNA segments, the variable gene segment, the diversity gene segment, and the joining gene segment (V-D-J). A single Vα or Vβ domain may be sufficient to confer antigen-binding specificity. Furthermore, TCRs that bind a particular antigen may be isolated using a Vα or Vβ domain from a TCR that binds the antigen to screen a library of complementary Vα or Vβ domains, respectively.

The terms "complementarity determining region," and "CDR," are synonymous with "hypervariable region" or "HVR," and are known in the art to refer to non-contiguous sequences of amino acids within TCR variable regions, which confer antigen specificity and/or binding affinity. In general, there are three CDRs in each α-chain variable region (αCDR1, αCDR2, αCDR3) and three CDRs in each β-chain variable region (βCDR1, βCDR2, βCDR3). CDR3 is thought to be the main CDR responsible for recognizing processed antigen. CDR1 and CDR2 mainly interact with the MHC. In certain embodiments, a binding protein of the present disclosure comprises an αCDR1, an αCDR2, and/or an αCDR3 amino acid sequence of a Vα domain as set forth in any one of SEQ ID NOs:1-4. In certain embodiments, a binding protein of the present disclosure comprises a βCDR1, a βCDR2, and/or a βCDR3 amino acid sequence of a Vβ domain as set forth in any one of SEQ ID NOs:5-7.

"Antigen" or "Ag" as used herein refers to an immunogenic molecule that provokes an immune response. This immune response may involve antibody production, activation of specific immunologically-competent cells (e.g., T cells), or both. An antigen (immunogenic molecule) may be, for example, a peptide, glycopeptide, polypeptide, glycopolypeptide, polynucleotide, polysaccharide, lipid or the like. It is readily apparent that an antigen can be synthesized, produced recombinantly, or derived from a biological sample. Exemplary biological samples that can contain one or more antigens include tissue samples, tumor samples, cells, biological fluids, or combinations thereof. Antigens can be produced by cells that have been modified or genetically engineered to express an antigen. Exemplary antigens include BRAF$^{V600E}$.

The term "epitope" or "antigenic epitope" includes any molecule, structure, amino acid sequence or protein determinant that is recognized and specifically bound by a cognate binding molecule, such as an immunoglobulin, T cell receptor (TCR), chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics.

A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target (e.g., BRAF$^{V600E}$). A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for their specific ability to bind to a biological molecule, a molecular complex or other target of interest.

As used herein, "specifically binds" or "specific for" refers to an association or union of a binding protein (e.g., TCR receptor) or a binding domain (or fusion protein thereof) to a target molecule with an affinity or $K_a$ (i.e., an equilibrium association constant of a particular binding interaction with units of 1/M) equal to or greater than $10^5$ M$^{-1}$ (which equals the ratio of the on-rate [$k_{on}$] to the off-rate [$k_{off}$] for this association reaction), while not significantly associating or uniting with any other molecules or components in a sample. Binding proteins or binding domains (or fusion proteins thereof) may be classified as "high-affinity" binding proteins or binding domains (or fusion proteins thereof) or as "low-affinity" binding proteins or binding domains (or fusion proteins thereof). "High-affinity" binding proteins or binding domains refer to those binding proteins or binding domains having a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low-affinity" binding proteins or binding domains refer to those binding proteins or binding domains having a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a $K_a$ (equilibrium association constant) for the target antigen that is higher than the wild type binding domain, due to a $K_d$ (dissociation constant) for the target antigen that is less than that of the wild type binding domain, due to an off-rate ($k_{off}$) for the target antigen that is less than that of the wild type binding domain, or a combination thereof. In certain embodiments, enhanced affinity TCRs may be codon optimized to enhance expression in a particular host cell, such as T cells (Scholten et al., *Clin. Immunol.* 119:135, 2006).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent). Assays for assessing affinity or apparent affinity or relative affinity are also known. In certain examples, apparent affinity for a TCR is measured by assessing binding to various concentrations of tetramers, for example, by flow cytometry using labeled tetramers. In some examples, apparent $K_D$ of a TCR is measured using 2-fold dilutions of labeled tetramers at a range of concentrations, followed by determination of binding curves by non-linear regression, apparent $K_D$ being determined as the concentration of ligand that yielded half-maximal binding.

The term "BRAF$^{V600E}$-specific binding protein" refers to a protein or polypeptide that specifically binds to a BRAF$^{V600E}$ peptide antigen or a BRAF$^{V600E}$ peptide antigen:HLA complex, e.g., on a cell surface, and does not bind a HLA complex on a cell surface comprising a BRAF peptide not containing the BRAF$^{V600E}$ mutation.

In certain embodiments, a BRAF$^{V600E}$-specific binding protein binds a BRAF$^{V600E}$-containing peptide:HLA complex (or BRAF$^{V600E}$-containing peptide:MHC complex) with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M, or with an affinity that is about the same as, at least about the same as, or is greater than at or about the affinity exhibited by an exemplary BRAF$^{V600E}$-specific binding protein provided herein, such as any of the BRAF$^{V600E}$-specific TCRs provided herein, for example, as measured by the same assay. In certain embodiments, a BRAF$^{V600E}$-specific binding protein comprises a BRAF$^{V600E}$-specific immunoglobulin superfamily binding protein or binding portion thereof.

The term "BRAF$^{V600E}$ binding domain" or "BRAF$^{V600E}$ binding fragment" refers to a domain or portion of a BRAF$^{V600E}$-specific binding protein responsible for the specific BRAF$^{V600E}$ binding. A BRAF$^{V600E}$-specific binding domain alone (i.e., without any other portion of a BRAF$^{V600E}$-specific binding protein) can be soluble and can bind to BRAF$^{V600E}$ (e.g., in complex with an MHC receptor molecule or functional fragment thereof) with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M. Exemplary BRAF$^{V600E}$-specific binding domains include BRAF$^{V600E}$-specific scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker) and scFv fragments as described herein, which can be derived from an anti-BRAF$^{V600E}$ TCR or antibody.

Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an MHC gene that is relevant for antigen presentation) APC and T cells, are well established (see, e.g., Murphy, Janeway's Immunobiology (8$^{th}$ Ed.) 2011 Garland Science, NY; chapters 6, 9 and 16). For example, processed antigen peptides originating in the cytosol (e.g., tumor antigen, intracellular pathogen) are generally from about 7 amino acids to about 11 amino acids in length and will associate with class I MHC molecules, whereas peptides processed in the vesicular system (e.g., bacterial, viral) will generally vary in length from about 10 amino acids to about 25 amino acids and associate with class II MHC molecules.

"BRAF$^{V600E}$ antigen" or "BRAF$^{V600E}$ peptide antigen" or "BRAF$^{V600E}$-containing peptide antigen" refers to a naturally or synthetically produced portion of a BRAF protein ranging in length from about 7 amino acids to about 20 amino acids and comprising the V600E substitution mutation (e.g., a peptide from BRAF$^{597-603}$, or BRAF$^{590-610}$, that includes a glutamic acid substituted for a valine at the residue corresponding to position 600 of the full-length wild-type BRAF; see, e.g., Uniprot entry no. P15056 and NCBI Reference identifier NP_004324.2), which can form a complex with a MHC (e.g., HLA) molecule and such a complex can bind with a binding protein specific fora BRAF$^{V600E}$ peptide:MHC (e.g., HLA) complex. Exemplary BRAF$^{V600E}$ peptide antigens include those having the amino acid sequence set forth in SEQ ID NO.: 38 or 39.

A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, for instance, or about four to about 20 amino acids or about eight to about 15 amino acids or about 15 to about 25 amino acids.

"Junction amino acids" or "junction amino acid residues" refer to one or more (e.g., about 2-10) amino acid residues between two adjacent motifs, regions or domains of a polypeptide, such as between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein).

An "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain) of at least 85% (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%).

As used herein, "nucleic acid" or "nucleic acid molecule" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region ("leader and trailer") as well as intervening sequences (introns) between individual coding segments (exons).

As used herein, the term "recombinant" refers to a cell, microorganism, nucleic acid molecule, or vector that has been genetically engineered by human intervention—that is, modified by introduction of a heterologous nucleic acid molecule, or refers to a cell or microorganism that has been altered such that expression of an endogenous nucleic acid molecule or gene is controlled, deregulated, deleted, attenuated, or constitutive. Human generated genetic alterations may include, for example, modifications that introduce nucleic acid molecules (which may include an expression control element, such as a promoter) that encode one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, NY, pp. 71-77, 1975; Lewin, Genes IV, Oxford University Press, NY and Cell Press, Cambridge, MA, p. 8, 1990).

The term "construct" refers to any polynucleotide that contains a recombinant nucleic acid molecule. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Exemplary vectors are those capable of autonomous replication (episomal vector) or expression of nucleic acid molecules to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

The term "operably linked" refers to the association of two or more nucleic acid molecules on a single nucleic acid fragment so that the function of one is affected by the other. For example, a promoter is operably linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

The term "introduced" in the context of inserting a nucleic acid molecule into a cell, means "transfection", or "transformation" or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, "heterologous" nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous nucleic acid molecule, construct or sequence may be from a different genus or species. In certain embodiments, a heterologous nucleic acid molecule is added (i.e., is not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein or other activity encoded by a heterologous polynucleotide introduced into the host cell, even if the host cell encodes a homologous protein or activity.

As described herein, more than one heterologous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more heterologous nucleic acid molecules encoding desired binding proteins specific for a BRAF$^{V600E}$ antigen peptide (e.g., TCRα and TCRβ). When two or more heterologous nucleic acid molecules are introduced into a host cell, it is understood that the two or more heterologous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous polynucleotide may be homologous to a native host cell gene, and may optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a CD24$^{Lo}$ Lin$^-$ CD117$^+$ phenotype or those found in the thymus (referred to as progenitor thymocytes).

As used herein, the term "host" refers to a cell (e.g., T cell) or microorganism targeted for genetic modification with a heterologous nucleic acid molecule to produce a polypeptide of interest (e.g., an anti-BRAF$^{V600E}$ TCR). In certain embodiments, a host cell may optionally already possess or be modified to include other genetic modifications that confer desired properties related or unrelated to, e.g., biosynthesis of the heterologous protein (e.g., inclusion of a detectable marker; deleted, altered or truncated endogenous TCR; or increased co-stimulatory factor expression). In certain embodiments, a host cell is a human hematopoietic progenitor cell transduced with a heterologous nucleic acid molecule encoding a TCRα chain specific for a BRAF$^{V600E}$ antigen peptide.

As used herein, "hyperproliferative disorder" refers to excessive growth or proliferation as compared to a normal or undiseased cell. Exemplary hyperproliferative disorders include tumors, cancers, neoplastic tissue, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like).

Binding Proteins Specific for BRAF$^{V600E}$ Peptide:HLA Complexes

BRAF (also known as B-RAF1, BRAF1, NS7, RAFB1, B-Raf, B-Raf proto-oncogene, and serine/threonine kinase) refers to a 766-amino acid protein encoded by the BRAF gene. The transcript sequence for human wild-type BRAF is set forth in NCBI Reference identifier NM_004333.4 (SEQ ID NO:78), and the protein sequence is set forth in NCBI Reference identifier NP_004324.2 (SEQ ID NO:36). BRAF is a member of the Raf kinase family of growth signal transduction protein kinases, and plays a role in regulating the MAP kinase/ERKs signaling pathway, which affects cell division, differentiation, and secretion. In terms of structure, BRAF is composed of three conserved domains characteristic of Raf kinases: a Ras-GTP-binding self-regulatory domain; a serine-rich hinge region; and a catalytic kinase domain that phosphorylates a consensus sequence on protein substrates (CR1, CR2, and CR3, respectively). Active B-Raf forms dimers.

A mutant form of BRAF kinase comprising a V600E mutation (BRAF$^{V600E}$) is an oncogenic driver present in numerous neoplastic conditions, including 40% of melanoma cases, 10% of colorectal cancer cases, and 1% of non-small cell lung cancer cases, and confers constitutive signaling that promotes tumor cell growth and survival. Small molecule BRAF inhibitors have some efficacy in melanoma, but resistance evolves by recruitment of alternative signaling pathways without loss of expression of BRAF$^{V600E}$ protein. See Shi et al., *Cancer Disc.* 4(1):80 (2014).

In certain aspects, the present disclosure provides a binding protein comprising: (a) a T cell receptor (TCR) α chain variable (Vα) domain having a CDR3 amino acid sequence set forth in any one of SEQ ID NOS:29-32, or a CDR3 amino acid sequence set forth in any one of SEQ ID NOS:29-32 with up to five amino acid substitutions, insertions, and/or deletions, and a TCR β chain variable (Vβ) domain; (b) a Vα domain, and a Vβ domain having a CDR3 amino acid sequence as set forth in any one of SEQ ID NOS:33-35, or a CDR3 amino acid sequence set forth in any one of SEQ ID NOS:33-35 with up to five amino acid substitutions, insertions, and/or deletions; or (c) a Vα domain of (a) and a Vβ domain of (b), wherein the binding protein is capable of specifically binding to a HLA complex on a cell surface comprising a BRAF peptide containing a BRAF$^{V600E}$ mutation, and does not bind a HLA complex on a cell surface comprising a BRAF peptide not containing the BRAF$^{V600E}$ mutation. In certain embodiments, the HLA complex comprises HLA-DQ.

In certain embodiments, (a) the Vα domain comprises the CDR3 amino acid sequence of SEQ ID NO:29 and the Vβ domain comprises the CDR3 amino acid sequence of SEQ ID NO:33, (b) the Vα domain comprises the CDR3 amino acid sequence of SEQ ID NO: 30 and the Vβ domain comprises the CDR3 amino acid sequence of SEQ ID NO:34, (c) the Vα domain comprises the CDR3 amino acid sequence of SEQ ID NO:31 and the Vβ domain comprises the CDR3 amino acid sequence of SEQ ID NO:34, (d) the Vα domain comprises the CDR3 amino acid sequence of SEQ ID NO:32 and the Vβ domain comprises the CDR3 amino acid sequence of SEQ ID NO:35, (e) the Vα domain comprises the CDR3 amino acid sequence of SEQ ID NO:29 and the Vβ domain comprises the CDR3 amino acid sequence of SEQ ID NO:34, (f) the Vα domain comprises the CDR3 amino acid sequence of SEQ ID NO:29 and the Vβ domain comprises the CDR3 amino acid sequence of SEQ ID NO:35, (g) the Vα domain comprises the CDR3 amino acid sequence of SEQ ID NO:30 and the Vβ domain comprises the CDR3 amino acid sequence of SEQ ID NO:33, (h) the Vα domain comprises the CDR3 amino acid of SEQ ID NO:30 and the Vβ domain comprises the CDR3 amino acid sequence of SEQ ID NO:35, (i) the Vα domain comprises the CDR3 amino acid of SEQ ID NO:31 and the Vβ domain comprises the CDR3 amino acid sequence of SEQ ID NO:33, (j) the Vα domain comprises the CDR3 amino acid sequence of SEQ ID NO:31 and the Vβ domain comprises the CDR3 amino acid sequence of SEQ ID NO:35, (k) the Vα domain comprises the CDR3 amino acid sequence of SEQ ID NO:32 and the Vβ domain comprises the CDR3 amino acid sequence of SEQ ID NO:33, or (l) the Vα domain comprises the CDR3 amino acid sequence of SEQ ID NO:32 and the Vβ domain comprises the CDR3 amino acid sequence of SEQ ID NO:34.

Peptide-MHC complexes, such as BRAF$^{V600E}$ peptide:HLA complexes, are recognized by and bound by a TCR through the Vα and Vβ domains. During lymphocyte development, Vα exons are assembled from different variable and joining gene segments (V-J), and Vβ exons are assembled from different variable, diversity, and joining gene segments (V-D-J). The TCRα chromosomal locus has 70-80 variable gene segments and 61 joining gene segments. The TCRβ chromosomal locus has 52 variable gene segments, and two separate clusters of each containing a single diversity gene segment, together with six or seven joining gene segments. Functional Vα and Vβ gene exons are generated by the recombination of a variable gene segment with a joining gene segment for Vα, and a variable gene segment with a diversity gene segment and a joining gene segment for Vβ.

The Vα and Vβ domains each comprise three hypervariable loops, also referred to as complementary determining regions (CDRs) that contact the peptide-MHC complex. CDR1 and CDR2 are encoded within the variable gene segment, whereas CDR3 is encoded by the region spanning the variable and joining segments for Vα, or the region spanning variable, diversity, and joining segments for Vβ. Compared with CDR1 and CDR2, CDR3 is significantly more diverse because of the addition and loss of nucleotides during the recombination process.

TCR variable domain sequences can be aligned to a numbering scheme (Kabat, Chothia, Enhanced Chothia, and Aho), allowing equivalent residue positions to be annotated and for different molecules to be compared using ANARCI software tool (2016, Bioinformatics 15:298-300). A numbering scheme provides a standardized delineation of framework regions and CDRs in the TCR variable domains.

Accordingly, CDR1 and CDR2 sequences may be deduced from the corresponding variable gene segments (e.g., TCRBV28-01, TCRAV21-01, TCRAV26-01, TCRAV12-02 alleles). In certain embodiments, (a) the Vα CDR3 amino acid sequence comprises the amino acid sequence set forth in SEQ ID NO:29 and the Vα domain further comprises a CDR1 amino acid sequence and CDR2 amino acid sequence encoded by the polynucleotide sequence set forth in SEQ ID NO:11, (b) the Vα CDR3 amino acid sequence comprises the amino acid sequence set forth in SEQ ID NO:30 and the Vα domain further comprises a CDR1 amino acid sequence and CDR2 amino acid sequence encoded by the polynucleotide sequence set forth in SEQ ID NO:12, (c) the Vα CDR3 amino acid sequence comprises the amino acid sequence set forth in SEQ ID NO:31 and the Vα domain further comprises a CDR1 amino acid sequence and CDR2 amino acid sequence encoded by the polynucleotide sequence set forth in SEQ ID NO:13, or (d) the Vα CDR3 amino acid sequence comprises the amino acid sequence set forth in SEQ ID NO:32 and the Vα domain further comprises a CDR1 amino acid sequence and CDR2 amino acid sequence encoded by the polynucleotide sequence set forth in SEQ ID NO:13. In certain embodiments, the Vβ CDR3 amino acid sequence comprises the amino acid sequence set forth in any one of SEQ ID NOS:33-35 and the Vβ domain further comprises a CDR1 amino acid sequence and CDR2 amino acid sequence encoded by the polynucleotide sequence set forth in SEQ ID NO:8.

Methods of identifying binding pairs of TCR Vα and Vβ domains include, for example, those described in PCT Patent Publication No. WO 2016/161273; Redmond et al., 2016, Genome Med. 8: 80; Munson et al., 2016, Proc. Natl. Acad. Sci. 113:8272-7; Kim et al., 2012, PLoS ONE 7:e37338 (each of the methods from which are incorporated by reference in its entirety). Accordingly, a Vα domain for the BRAF$^{V600E}$-specific Vβ domains described herein (e.g., a Vβ domain comprising CDR3 as set forth in any one of SEQ ID NOS:33-35), or vice versa, may be identified.

A BRAF$^{V600E}$-specific binding protein described herein may possess one or more amino acid substitutions, deletions, or insertions relative to a naturally occurring binding protein (e.g., TCR). Conservative substitutions of amino acids are known and may occur naturally or may be introduced when the binding protein or TCR is recombinantly produced. Amino acid substitutions, deletions, and insertions may be introduced into a protein using mutagenesis methods (see, e.g., Sambrook et al., *Molecular Cloning: A Laboratory Manual,* 3d ed., Cold Spring Harbor Laboratory Press, NY, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra).

A variety of criteria known in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

Accordingly, in certain embodiments, the binding protein of the instant disclosure comprises a Vα domain that is at least about 90% (e.g., at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or at least about 99.9%) identical to the amino acid sequence set forth in any one of SEQ ID NOS:1-4, and comprises a Vβ domain that is at least about 90% (e.g., at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or at least about 99.9%) identical to the amino acid sequence set forth in any one of SEQ ID NOS:5-7, provided that (a) at least three or four of the CDRs have no mutations and (b) the CDRs that do have mutations have only up to three amino acid substitutions, insertions, deletions or combinations thereof. In certain embodiments, the Vα domain comprises or consists of the amino acid sequence set forth in any one of SEQ ID NOS:1-4. In certain embodiments, the Vβ domain comprises or consists of the amino acid sequence set forth in any one of SEQ ID NOS:5-7.

In particular embodiments, the Vα domain comprises or consists of the amino acid sequence set forth in SEQ ID NO:1 and the Vβ domain comprises or consists of the amino acid sequence set forth in SEQ ID NO:5.

In other embodiments, the Vα domain comprises or consists of the amino acid sequence set forth in SEQ ID NO:1 and the Vβ domain comprises or consists of the amino acid sequence set forth in SEQ ID NO:6.

In other embodiments, the Vα domain comprises or consists of the amino acid sequence set forth in SEQ ID NO:1 and the Vβ domain comprises or consists of the amino acid sequence set forth in SEQ ID NO:7.

In particular embodiments, the Vα domain comprises or consists of the amino acid sequence set forth in SEQ ID NO:2 and the Vβ domain comprises or consists of the amino acid sequence set forth in SEQ ID NO:5.

In other embodiments, the Vα domain comprises or consists of the amino acid sequence set forth in SEQ ID NO:2 and the Vβ domain comprises or consists of the amino acid sequence set forth in SEQ ID NO:6.

In other embodiments, the Vα domain comprises or consists of the amino acid sequence set forth in SEQ ID NO:2 and the Vβ domain comprises or consists of the amino acid sequence set forth in SEQ ID NO:7.

In particular embodiments, the Vα domain comprises or consists of the amino acid sequence set forth in SEQ ID NO:3 and the Vβ domain comprises or consists of the amino acid sequence set forth in SEQ ID NO:5.

In other embodiments, the Vα domain comprises or consists of the amino acid sequence set forth in SEQ ID NO:3 and the Vβ domain comprises or consists of the amino acid sequence set forth in SEQ ID NO:6.

In other embodiments, the Vα domain comprises or consists of the amino acid sequence set forth in SEQ ID NO:3 and the Vβ domain comprises or consists of the amino acid sequence set forth in SEQ ID NO:7.

In particular embodiments, the Vα domain comprises or consists of the amino acid sequence set forth in SEQ ID NO:4 and the Vβ domain comprises or consists of the amino acid sequence set forth in SEQ ID NO:5.

In other embodiments, the Vα domain comprises or consists of the amino acid sequence set forth in SEQ ID NO:4 and the Vβ domain comprises or consists of the amino acid sequence set forth in SEQ ID NO:6.

In other embodiments, the Vα domain comprises or consists of the amino acid sequence set forth in SEQ ID NO:4 and the Vβ domain comprises or consists of of the amino acid sequence set forth in SEQ ID NO:7.

In further embodiments, a BRAF$^{V600E}$-specific binding protein is a TCR, an antigen-binding fragment of a TCR, or a chimeric antigen receptor. A "chimeric antigen receptor" (also called a CAR) is a fusion protein comprising an antigen binding domain (e.g., obtained or derived from an immunoglobulin or immunoglobulin-like molecule, such as an scFv derived from an antibody or TCR specific for a cancer antigen, or an antigen-binding domain obtained or derived from a killer immunoreceptor from an NK cell) linked to a transmembrane domain and one or more intracellular signaling domains (optionally containing co-stimulatory domain(s)) (see, e.g., Sadelain et al., *Cancer Discov.*, 3(4): 388-398, 2013; see also Harris and Kranz, *Trends Pharmacol. Sci.*, 37(3): 220-230, 2016; Stone et al., *Cancer Immunol. Immunother.*, 63(11):1163-1176, 2014). In certain embodiments, a binding protein comprises a CAR comprising a BRAF$^{V600E}$-specific TCR binding domain (see, e.g., Walseng et al., *Scientific Reports* 7:10713, 2017; the TCR CAR constructs and methods of which are hereby incorporated by reference in their entirety). Methods of making CARs are described, for example, in U.S. Pat. Nos. 6,410,319; 7,446,191; U.S. Patent Publication No. 2010/065818; U.S. Pat. No. 8,822,647; PCT Publication No. WO 2014/031687; U.S. Pat. No. 7,514,537; and Brentjens et al., *Clin. Cancer Res.* 13:5426, 2007.

In certain embodiments, the antigen-binding fragment of the TCR comprises a single chain TCR (scTCR), which comprises both the TCR Vα and Vβ domains TCR, but only a single TCR constant domain (Cα or Cβ. In certain embodiments, the antigen-binding fragment of the TCR, or chimeric antigen receptor is chimeric (e.g., comprises amino acid residues or motifs from more than one donor or species), humanized (e.g., comprises residues from a non-human organism that are altered or substituted so as to reduce the risk of immunogenicity in a human), or human. Binding proteins according to the present disclosure, e.g., TCRs, may further comprise a TCR constant domain, e.g., joined to the C-terminus of a Vα domain, a Vβ domain, or both. A TCR β-chain constant domain may be encoded by a TRBC1 gene or TRBC2 gene, and a TCRα-chain may be encoded by a TRAC gene. In certain embodiments, the TCR comprises an α chain constant (Cα) domain having at least 90% (e.g., at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or at least about 99.9%) sequence identity to the amino acid sequence set forth in SEQ ID NO:25. In a particular embodiment, the Cα domain comprises the amino acid sequence set forth in SEQ ID NO:25. In certain embodiments, the TCR comprises a β chain (Cβ) constant domain having at least 90% (e.g., at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or at least about 99.9%) sequence identity to the amino acid sequence set forth in SEQ ID NO:26. In a particular embodiment, Cβ domain comprises the amino acid sequence set forth in SEQ ID NO:26.

In certain embodiments, a binding protein comprises a α-chain (comprised of a Vα domain and a Cα domain) comprising the amino acid sequence set forth in any one of SEQ ID NOS:55-58. In certain embodiments, a binding protein comprises a β-chain (comprised of a Vβ domain and a Cβ domain) comprising the amino acid sequence set forth in any one of SEQ ID NOS:59-61.

Methods useful for isolating and purifying recombinantly produced soluble binding proteins (e.g., TCRs), by way of example, may include obtaining supernatants from suitable host cell/vector systems that secrete the recombinant soluble TCR into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant soluble TCR described herein include batch cell culture, which is monitored and controlled to maintain appropriate culture conditions. Purification of the soluble TCR may be performed according to methods described herein and known in the art and that comport with laws and guidelines of domestic and foreign regulatory agencies.

In certain embodiments, nucleic acid molecules encoding a binding protein (e.g., a TCR) specific for a BRAF$^{V600E}$ peptide:HLA complex) are used to transfect/transduce a host cell (e.g., a T cell) for use in adoptive transfer therapy. Advances in TCR sequencing have been described (e.g., Robins et al., *Blood* 114:4099, 2009; Robins et al., *Sci. Translat. Med.* 2:47ra64, 2010; Robins et al., (September 10) *J. Imm. Meth*. Epub ahead of print, 2011; Warren et al., *Genome Res.* 21:790, 2011) and may be employed in the course of practicing embodiments according to the present disclosure. Similarly, methods for transfecting/transducing T cells with desired nucleic acids have been described (e.g., U.S. Patent Application Pub. No. US 2004/0087025) as have adoptive transfer procedures using T cells of desired antigen-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein, including those directed to TCRs specific for BRAF$^{V600E}$ peptide antigens complexed with an HLA receptor.

The BRAF$^{V600E}$-specific binding proteins or domains as described herein may be functionally characterized according to any of a large number of art-accepted methodologies for assaying T cell activity, including determination of T cell binding, activation or induction and also including determination of T cell responses that are antigen-specific. Examples include determination of T cell proliferation, T cell cytokine release, antigen-specific T cell stimulation, MHC restricted T cell stimulation, CTL activity (e.g., by detecting $^{51}$Cr release from pre-loaded target cells), changes in T cell phenotypic marker expression, and other measures of T-cell functions. Procedures for performing these and similar assays are may be found, for example, in Lefkovits (*Immunology Methods Manual: The Comprehensive Sourcebook of Techniques*, 1998). See, also, *Current Protocols in Immunology*; Weir, *Handbook of Experimental Immunology*, Blackwell Scientific, Boston, MA (1986); Mishell and Shigii (eds.) *Selected Methods in Cellular Immunology*, Freeman Publishing, San Francisco, CA (1979); Green and Reed, *Science* 281:1309 (1998) and references cited therein.

"MHC-peptide tetramer staining" refers to an assay used to detect antigen-specific T cells, which features a tetramer of MHC molecules, each comprising an identical peptide having an amino acid sequence that is cognate (e.g., identical or related to) at least one antigen (e.g., BRAF$^{V600E}$), wherein the complex is capable of binding T cell receptors specific for the cognate antigen. Each of the MHC molecules may be tagged with a biotin molecule. Biotinylated MHC/peptides are tetramerized by the addition of streptavidin, which can be fluorescently labeled. The tetramer may be detected by flow cytometry via the fluorescent label. In certain embodiments, an MHC-peptide tetramer assay is used to detect or select enhanced affinity TCRs of the instant disclosure.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

In further aspects, the present disclosure provides compositions comprising a binding protein according to the present disclosure and a pharmaceutically acceptable carrier, diluent, or excipient. Pharmaceutically acceptable excipients are biologically compatible vehicles, e.g., physiological saline, which are described in greater detail herein, that are suitable for administration to a human or other non-human mammalian subject.

Antigen presentation by immune cells (e.g., dendritic cells, phagocytes, and B cells) is determined in part by the HLA complexes present on the cells. Without wishing to be bound by theory, it is believed that HLA proteins encoded by different HLA alleles can vary in their ability to present particular antigen peptides and interact with immune cell proteins (e.g., TCRs). For example, a given antigen peptide may be presented by HLA-DQ complexes, but not HLA-DR complexes, or vice versa. In certain embodiments, a binding protein according to the present disclosure is capable of recognizing a BRAF$^{V600E}$ peptide complexed with HLA-DQ. In certain embodiments, the HLA complex comprises HLA-DQB1*0301, *0302, or *0303. In certain embodiments, the HLA complex comprises HLA-DQB1*0302. In further embodiments, the HLA complex comprises HLA-DQA1*03.

Peptide antigens targeted by binding proteins according to the present disclosure can also vary on size depending on, for example, the type of HLA molecule presenting the antigen. Generally, HLA Class I complexes present peptides that are about 8-10 amino acids length, while HLA Class II complexes present peptides that are about 15-24 amino acids in length, though the peptides may be shorter or longer than these general lengths. Accordingly, in certain embodiments, a BRAF$^{V600E}$ peptide specifically bound by a binding protein of the present disclosure comprises from about 7 to about 27 amino acids, from about 10 to about 25 amino acids, or from about 12 to about 20 amino acids, or from about 15 to about 19 amino acids. In particular embodiments, the BRAF$^{V600E}$ peptide comprises the amino acid sequence set forth in SEQ ID NO:38 or 39.

Polynucleotides Encoding BRAF$^{V600E}$-Specific Binding Proteins and Related Vectors In yet further aspects, isolated polynucleotides and expression vectors that encode binding proteins according to the present disclosure are provided. Construction of an expression vector that is used for genetically engineering and producing a binding protein or TCR specific for a BRAF$^{V600E}$ peptide of interest can be accomplished by using any suitable molecular biology engineering techniques known in the art. To obtain efficient transcription and translation, a polynucleotide in each recombinant expression construct includes at least one appropriate expression control sequence (also called a regulatory sequence), such as a leader sequence and particularly a promoter operably (i.e., operatively) linked to the nucleotide sequence encoding the immunogen.

Certain embodiments relate to polynucleotides that encode the binding proteins provided herein, such as binding proteins (e.g., TCRs or CARs) specific for a BRAF$^{V600E}$ peptide:HLA complex. A nucleic acid may be a single- or a double-stranded DNA, cDNA or RNA in any form, and may include a positive and a negative strand of the nucleic acid which complement each other, including anti-sense DNA, cDNA and RNA. Also included are siRNA, microRNA, RNA-DNA hybrids, ribozymes, and other various naturally occurring or synthetic forms of DNA or RNA. It will be appreciated that a polynucleotide of the present disclosure can vary (i.e., comprise a different nucleotide sequence) as compared to a reference polynucleotide sequence disclosed herein and still encode a same amino acid or polypeptide, due to, for example, the degeneracy of the genetic code. In certain embodiments, a polynucleotide encoding, for example, a binding protein or a portion thereof, a self-cleaving peptide, a linker peptide; or a binding protein-encoding construct, may have at least about 80% (e.g., at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or at least about 99.9%) identity to a polynucleotide according to any one of SEQ ID NOs:8-24; 27; 28; 44-48; 62-68; and 73-77.

In any of the aforementioned embodiments, a polynucleotide encoding a binding protein of the present disclosure is codon optimized for efficient expression in a target host cell.

Certain embodiments include polynucleotides of this disclosure contained in a vector. An exemplary vector may comprise a polynucleotide capable of transporting another polynucleotide to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector, retroviral vector). Additionally, some vectors are capable of directing the expression of genes to which they are operatively linked (these vectors may be referred to as "expression vectors"). According to related embodiments, it is further understood that, if one or more agents (e.g., polynucleotides encoding binding proteins or recombinant TCRs specific for BRAF$^{V600E}$, or variants thereof, as described herein) are co-administered to a subject, that each agent may reside in separate or the same vectors, and multiple vectors (each containing a different agent or the same agent) may be introduced to a cell or cell population or administered to a subject.

In certain embodiments, polynucleotides encoding binding proteins specific for a BRAF$^{V600E}$ peptide:HLA complex may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest. In certain embodiments, polynucleotides encoding binding proteins of the instant disclosure are contained in an expression vector that is a viral vector, such as a lentiviral vector or a γ-retroviral vector.

In certain embodiments, expression vectors are provided comprising a polynucleotide encoding a binding protein of the present disclosure, wherein the polynucleotide is operably linked to an expression control sequence (e.g., a promoter). In certain embodiments, the vector is capable of delivering the polynucleotide to a host cell. In certain embodiments, the host cell is a hematopoietic progenitor cell or a human immune system cell. In further embodiments, the immune system cell is a CD4+ T cell, a CD8+ T cell, a CD4−CD8− double negative T cell, a γδ T cell, a natural killer cell, a dendritic cell, or any combination thereof. In certain embodiments, the immune system cell is a CD4+ T cell. In certain embodiments, the T cell is a naïve T cell, a central memory T cell, an effector memory T cell, or any combination thereof.

In any of the embodiments herein, the vector is a viral vector. In certain embodiments, the viral vector is a lentiviral vector or a γ-retroviral vector.

Host Cells

In still further aspects, host cells are provided that comprise a heterologous polynucleotide according to the present disclosure, wherein the host cell expresses on its cell surface a binding protein encoded by the heterologous polynucleotide (i.e., expresses a binding protein according to the present disclosure). In particular embodiments, an expression vector is delivered to an appropriate cell, for example, a T cell or an antigen-presenting cell, i.e., a cell that displays a peptide/MHC complex on its cell surface (e.g., a dendritic cell). In certain embodiments, a host cell (e.g., a T cell, NK cell, or NK-T cell) lacks a CD8 co-receptor or a CD4 co-receptor and the encoded binding protein is capable of binding a BRAF$^{V600E}$ antigen:HLA complex in the absence of a CD4 or CD8 co-receptor. In certain embodiments, the host cell is a hematopoietic progenitor cell or a human immune system cell. For example, the immune system cell can be a CD4+ T cell, a CD8+ T cell, a CD4− CD8− double negative T cell, a γδ T cell, a natural killer cell, a natural killer T cell, a dendritic cell, or any combination thereof. In some embodiments, the encoded binding protein comprises a MHCII-restricted TCR binding domain and the host cell (e.g., a CD8+ T cell) comprises a polynucleotide encoding a heterologous CD4+ co-receptor.

In certain embodiments, wherein a T cell is the host, the T cell can be naïve, a central memory T cell, an effector memory T cell, a stem cell memory T cell, or any combination thereof. In certain embodiments, the T cell is a CD4+ T cell, a CD8+ T cell, or both. The expression vectors introduced into the host cells may also include, for example, lymphoid tissue-specific transcriptional regulatory elements (TREs), such as a B lymphocyte, T lymphocyte, or dendritic cell specific TREs. Lymphoid tissue specific TREs are known in the art (see, e.g., Thompson et al., *Mol. Cell. Biol.* 12:1043, 1992); Todd et al., *J. Exp. Med.* 177:1663, 1993); Penix et al., *J. Exp. Med.* 178:1483, 1993).

A host cell may include any individual cell or cell culture which may receive a vector or the incorporation of nucleic acids or express proteins. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989).

Accordingly, in one aspect, a host cell is provided that comprises a heterologous polynucleotide or an expression vector according to the present disclosure, wherein the host cell expresses on its cell surface a binding protein encoded by the heterologous polynucleotide. In certain embodiments, the portion of the heterologous polynucleotide that encodes the $V_\alpha$ domain is at least about 80% identical to the polynucleotide sequence set forth in any one of SEQ ID NOS:18-21. In certain embodiments, the portion of the heterologous polynucleotide that encodes the $V_\beta$ domain is at least about 80% identical to the polynucleotide sequence set forth in any one of SEQ ID NOS:22-24.

In certain embodiments, the portion of the heterologous polynucleotide that encodes the $V_\alpha$ domain comprises or consists of the polynucleotide sequence set forth in any one of SEQ ID NOS:18-21. In certain embodiments, the portion of the heterologous polynucleotide that encodes the $V_\beta$ domain comprises or consists of the polynucleotide sequence set forth in any one of SEQ ID NOS:22-24.

In certain embodiments, the portion of the heterologous polynucleotide that encodes the $V_\alpha$ domain comprises or consists of the polynucleotide sequence set forth in any one of SEQ ID NOS:18-21, and the portion of the heterologous polynucleotide that encodes the $V_\beta$ domain comprises or consists of the polynucleotide sequence set forth in any one of SEQ ID NOS:22-24.

In certain embodiments, the portion of the heterologous polynucleotide that encodes the $V_\alpha$ domain is linked to a portion that encodes a TCR α-chain constant domain, wherein the portion that encodes the α-chain constant domain comprises or consists of a sequence that is at least about 80% identical to the polynucleotide sequence set forth in SEQ ID NO:27.

In certain embodiments, the portion of the heterologous polynucleotide that encodes the $V_\beta$ domain is linked to a portion that encodes a TCR β-chain constant domain, wherein the portion that encodes the β-chain constant domain comprises or consists of a sequence that is at least about 80% identical to the polynucleotide sequence set forth in SEQ ID NO:28.

In particular embodiments, the portion of the polynucleotide that encodes the $V_\alpha$ domain comprises or consists of SEQ ID NO:18 and the portion that encodes the $V_\beta$ domain comprises or consists of SEQ ID NO:22.

In other embodiments, the portion of the polynucleotide that encodes the $V_\alpha$ domain comprises or consists of SEQ ID NO:19 and the portion that encodes the $V_\beta$ domain comprises or consists of SEQ ID NO:23.

In other embodiments, the portion of the polynucleotide that encodes the $V_\alpha$ domain comprises or consists of SEQ ID NO:20 and the portion that encodes the $V_\beta$ domain comprises or consists of SEQ ID NO:23.

In still other embodiments, the portion of the polynucleotide that encodes the $V_\alpha$ domain comprises or consists of SEQ ID NO:21 and the portion that encodes the $V_\beta$ domain comprises or consists of SEQ ID NO:24.

In any of the herein described embodiments, a host cell (e.g., a T cell) expressing a $BRAF^{V600E}$-specific binding protein of the present disclosure is capable of producing an interferon when co-cultured with an antigen-presenting cell presenting or expressing a $BRAF^{V600E}$-containing antigen. In certain embodiments, the produced interferon comprises interferon-gamma (IFN-γ). In some embodiments, the target cell has been pulsed with a peptide or polypeptide comprising or consisting of the $BRAF^{V600E}$-containing antigen. In some embodiments, the target cell has been transfected with a polynucleotide (e.g., DNA, cDNA, or mRNA) encoding a polypeptide or peptide comprising or consisting of the $BRAF^{V600E}$-containing antigen. In certain embodiments, a host cell of the present disclosure produces IFN-γ when cultured with an antigen-presenting cell that has been pulsed with a $BRAF^{V600E}$-containing antigen at a concentration of about 0.005 μg/mL to about 10 μg/mL antigen. In further embodiments, the host cell produces at least about 1,000 pg/mL IFN-γ when cultured with an antigen-presenting cell that has been pulsed with a $BRAF^{V600E}$-containing antigen at a concentration of at least about 0.1 μg/mL antigen. In some embodiments, the host cell produces at least about 1,000 pg/mL IFN-γ when cultured with an antigen-presenting cell pulsed with a $BRAF^{V600E}$-containing antigen at a concentration of at least about 0.1, 0.2, 0.3, 0.4, or 0.5 μg/mL antigen. In some embodiments, the host cell produces from about 1,000 pg/mL to about 10,000 pg/mL IFN-γ when cultured with an antigen-presenting cell pulsed with a $BRAF^{V600E}$-containing antigen at a concentration of about 0.5 μg/mL antigen to about 10 μg/mL antigen. In some embodiments, a target cell comprises a B cell. In further embodiments, the B cell expresses an HLA-DQ allele. In still further embodiments, the B cell is of B-LCL line 1331.

In certain embodiments, a portion of the polynucleotide encodes a self-cleaving peptide and is disposed between a TCR α-chain-encoding portion and a TCR β-chain-encoding portion. Self-cleaving peptides useful for expression of separable polypeptides by a single vector are known in the art and include, for example, Porcine teschovirus-1 2A (P2A) peptide, Thoseaasigna virus 2A (T2A) peptide, Equine rhinitis A virus (ERAV) 2A (E2A) peptide, and Foot-and-Mouth disease virus 2A (F2A) peptide. Accordingly, in certain embodiments, the portion of the heterologous polynucleotide that encodes the self-cleaving peptide comprises or consists of the polynucleotide sequence set forth in any one of SEQ ID NOS:44-48. In further embodiments, the encoded self-cleaving peptide comprises or consists of the amino acid sequence set forth in any one of SEQ ID NOS:49-52.

In certain embodiments, the host cell is a hematopoietic progenitor cell or a human immune system cell. In certain embodiments, the immune system cell is a CD4+ T cell, a CD8+ T cell, a CD4− CD8− double negative T cell, a γδ T cell, a natural killer cell, a dendritic cell, or any combination thereof. In certain embodiments, the immune system cell is a T cell. In particular embodiments, T cell is a naïve T cell, a central memory T cell, an effector memory T cell, or any combination thereof. In further embodiments, the T cell is a CD4+ T cell.

In certain embodiments, the binding protein or TCR expressed by the T cell is capable of more efficiently associating with a CD3 protein, a CD4 protein, or both, as compared to endogenous TCR. In certain embodiments, the binding protein or TCR higher surface expression on a T cell as compared to endogenous TCR.

In any of the foregoing embodiments, a host cell that comprises a heterologous polynucleotide encoding a $BRAF^{V600E}$-specific binding protein is an immune cell which is modified to reduce or eliminate expression of one or more endogenous genes that encode a polypeptide product selected from PD-1, LAG-3, CTLA4, TIM3, TIGIT, an HLA molecule, a TCR molecule, or any component or combination thereof. Without wishing to be bound by theory, certain endogenously expressed immune cell proteins may downregulate the immune activity of a modified immune host cell (e.g., PD-1, LAG-3, CTLA4, TIGIT), or may compete with a heterologous binding protein of the present disclosure for expression by the host cell, association with TCR complex components (e.g., CD3 proteins), or may interfere with the binding activity of a heterologously expressed binding protein of the present disclosure (e.g., an endogenous TCR that binds to a non-$BRAF^{V600E}$ antigen or a non-$BRAF^{V600E}$ antigen:HLA complex and interferes with binding of a presently disclosed binding protein to a $BRAF^{V600E}$ antigen) and interferes with the immune host cell binding a target cell that expresses $BRAF^{V600E}$ antigen), or any combination thereof. Further, endogenous proteins (e.g., immune host cell proteins, such as an HLA) expressed on a donor immune cell to be used in a cell transfer therapy may be recognized as foreign by an allogeneic recipient, which may result in elimination or suppression of the donor immune cell by the allogeneic recipient.

Accordingly, decreasing or eliminating expression or activity of such endogenous genes or proteins can improve the activity, tolerance, and persistence of the host cells in an autologous or allogeneic host setting, and allows universal administration of the cells (e.g., to any recipient regardless of HLA type). In certain embodiments, a modified host immune cell is a donor cell (e.g., allogeneic) or an autologous cell. In certain embodiments, a modified immune host cell of this disclosure comprises a chromosomal gene knockout of one or more of a gene that encodes PD-1, LAG-3, CTLA4, TIM3, TIGIT, an HLA component (e.g., a gene that encodes an α1 macroglobulin, an α2 macroglobulin, an α3 macroglobulin, a β1 microglobulin, or a β2 microglobulin), or a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8):1341 (2013) the gene editing techniques, compositions, and adoptive cell therapies of which are herein incorporated by reference in their entirety; e.g., SEQ ID NOs:142-149). As used herein, the term "chromosomal gene knockout" refers to a genetic alteration in a host cell that prevents production, by the host cell, of a functionally active endogenous polypeptide product. Alterations resulting in a chromosomal gene knockout can include, for example, introduced nonsense mutations (including the formation of premature stop codons), missense mutations, gene deletion, and strand breaks, as well as the heterologous expression of inhibitory nucleic acid molecules that inhibit endogenous gene expression in the host cell.

In certain embodiments, a chromosomal gene knock-out or gene knock-in is made by chromosomal editing of a host cell. Chromosomal editing can be performed using, for example, endonucleases. As used herein "endonuclease" refers to an enzyme capable of catalyzing cleavage of a phosphodiester bond within a polynucleotide chain. In certain embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for a donor gene "knock-in", for target gene "knock-out", and optionally to inactivate a target gene through a donor gene knock in or target gene knock out event. NHEJ is an error-prone repair process that often results in changes to the DNA sequence at the site of the cleavage, e.g., a substitution, deletion, or addition of at least one nucleotide. NHEJ may be used to "knock-out" a target gene. Examples of endonucleases include zinc finger nucleases, TALE-nucleases, CRISPR-Cas nucleases, meganucleases, and megaTALs.

As used herein, a "zinc finger nuclease" (ZFN) refers to a fusion protein comprising a zinc finger DNA-binding domain fused to a non-specific DNA cleavage domain, such as a FokI endonuclease. Each zinc finger motif of about 30 amino acids binds to about 3 base pairs of DNA, and amino acids at certain residues can be changed to alter triplet sequence specificity (see, e.g., Desjarlais et al., *Proc. Natl. Acad. Sci.* 90:2256-2260, 1993; Wolfe et al., *J. Mol. Biol.* 285:1917-1934, 1999). Multiple zinc finger motifs can be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In certain embodiments, a gene knockout comprises an insertion, a deletion, a mutation or a combination thereof, made using a ZFN molecule.

As used herein, a "transcription activator-like effector nuclease" (TALEN) refers to a fusion protein comprising a TALE DNA-binding domain and a DNA cleavage domain, such as a FokI endonuclease. A "TALE DNA binding domain" or "TALE" is composed of one or more TALE repeat domains/units, each generally having a highly conserved 33-35 amino acid sequence with divergent 12th and 13th amino acids. The TALE repeat domains are involved in binding of the TALE to a target DNA sequence. The divergent amino acid residues, referred to as the Repeat Variable Diresidue (RVD), correlate with specific nucleotide recognition. The natural (canonical) code for DNA recognition of these TALEs has been determined such that an HD (histine-aspartic acid) sequence at positions 12 and 13 of the TALE leads to the TALE binding to cytosine (C), NG (asparagine-glycine) binds to a T nucleotide, NI (asparagine-isoleucine) to A, NN (asparagine-asparagine) binds to a G or A nucleotide, and NG (asparagine-glycine) binds to a T nucleotide. Non-canonical (atypical) RVDs are also known (see, e.g., U.S. Patent Publication No. US 2011/0301073, which atypical RVDs are incorporated by reference herein in their entirety). TALENs can be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In certain embodiments, a gene knockout comprises an insertion, a deletion, a mutation or a combination thereof, and made using a TALEN molecule.

As used herein, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences can be introduced at the site of DSB via homology directed repair. The crRNA and tracrRNA can be engineered into a single guide RNA (sgRNA or gRNA) (see, e.g., Jinek et al., *Science* 337:816-21, 2012). Further, the region of the guide RNA complementary to the target site can be altered or programed to target a desired sequence (Xie et al., *PLOS One* 9:e100448, 2014; U.S. Pat. Appl. Pub. No. US 2014/0068797, U.S. Pat. Appl. Pub. No. US 2014/0186843; U.S. Pat. No. 8,697,359, and PCT Publication No. WO 2015/071474; each of which is incorporated by reference). In certain embodiments, a gene knockout comprises an insertion, a deletion, a mutation or a combination thereof, and made using a CRISPR/Cas nuclease system.

Exemplary gRNA sequences and methods of using the same to knock out endogenous genes that encode immune cell proteins include those described in Ren et al., *Clin. Cancer Res.* 23(9):2255-2266 (2017), the gRNAs, CAS9 DNAs, vectors, and gene knockout techniques of which are hereby incorporated by reference in their entirety.

In some embodiments, a gene knockout comprises a CRISPR-mediated gene knockout of a TCR α-chain constant region locus (Cα), a TCR β-chain constant region locus (Cβ), or both. In certain embodiments, a gRNA sequence targeting a TCR Cα locus comprises the nucleotide sequence AGAGTCTCTCAGCTGGTACA (SEQ ID NO:136). In certain embodiments, a gRNA sequence targeting a TCR Cα locus comprises the nucleotide sequence TGTGCTAGACATGAGGTCTA (SEQ ID NO:137). In certain embodiments, a gRNA sequence targeting a TCR Cβ locus comprises the nucleotide sequence GCAGTATCTGGAGTCATTGA (SEQ ID NO:138). In certain embodiments, a gRNA sequence targeting a TCR Cβ locus comprises the nucleotide sequence GGAGAATGACGAGTGGACCC (SEQ ID NO:139). In some embodiments, a gene knockout comprises a CRISPR-mediated gene knockout of a human β2M locus. In certain embodiments, a gRNA sequence targeting a human β2M comprises the nucleotide sequence CGCGAGCACAGCTAAGGCCA (SEQ ID NO:140). In some embodiments, a gene knockout comprises a CRISPR-mediated gene knockout of a PD-1 locus. In certain embodiments, a gRNA sequence targeting a PD-1 comprises the nucleotide sequence GGCCAGGATGGTTCTTAGGT (SEQ ID NO:141)

As used herein, a "meganuclease," also referred to as a "homing endonuclease," refers to an endodeoxyribonuclease characterized by a large recognition site (double stranded DNA sequences of about 12 to about 40 base pairs). Meganucleases can be divided into five families based on sequence and structure motifs: LAGLIDADG, GIY-YIG, HNH, His-Cys box and PD-(D/E)XK. Exemplary meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII, whose recognition sequences are known (see, e.g., U.S. Pat. Nos. 5,420,032 and 6,833,252; Belfort et al., *Nucleic Acids Res.* 25:3379-3388, 1997; Dujon et al., *Gene* 82:115-118, 1989; Perler et al., *Nucleic Acids Res.* 22:1125-1127, 1994; Jasin, *Trends Genet.* 12:224-228, 1996; Gimble et al., *J. Mol. Biol.* 263:163-180, 1996; Argast et al., *J. Mol. Biol.* 280:345-353, 1998).

In certain embodiments, naturally-occurring meganucleases may be used to promote site-specific genome modification of a target selected from PD-1, LAG3, TIM3, CTLA4, TIGIT, an HLA-encoding gene, or a TCR component-encoding gene. In other embodiments, an engineered meganuclease having a novel binding specificity for a target gene is used for site-specific genome modification (see, e.g., Porteus et al., *Nat. Biotechnol.* 23:967-73, 2005; Sussman et al., *J. Mol. Biol.* 342:31-41, 2004; Epinat et al., *Nucleic Acids Res.* 31:2952-62, 2003; Chevalier et al., *Molec. Cell* 10:895-905, 2002; Ashworth et al., *Nature* 441:656-659, 2006; Paques et al., *Curr. Gene Ther.* 7:49-66, 2007; U.S. Patent Publication Nos. US 2007/0117128; US 2006/0206949; US 2006/0153826; US 2006/0078552; and US 2004/0002092). In further embodiments, a chromosomal gene knockout is generated using a homing endonuclease that has been modified with modular DNA binding domains of TALENs to make a fusion protein known as a megaTAL. MegaTALs can be utilized to not only knock-out one or more target genes, but to also introduce (knock in) heterologous or exogenous polynucleotides when used in combination with an exogenous donor template encoding a polypeptide of interest, such as a TCRα chain, TCRβ chain or both, wherein the knocked-in TCR produced by the cell is specific for a BRAF$^{V600E}$ antigen or peptide.

In certain embodiments, a chromosomal gene knockout comprises an inhibitory nucleic acid molecule that is introduced into a host cell (e.g., an immune cell) comprising a heterologous polynucleotide encoding an antigen-specific receptor that specifically binds to a tumor associated antigen, wherein the inhibitory nucleic acid molecule encodes a target-specific inhibitor and wherein the encoded target-specific inhibitor inhibits endogenous gene expression (i.e., of PD-1, TIM3, LAG3, CTLA4, TIGIT, an HLA component, or a TCR component, or any combination thereof) in the host immune cell.

A chromosomal gene knockout can be confirmed directly by DNA sequencing of the host immune cell following use of the knockout procedure or agent. Chromosomal gene knockouts can also be inferred from the absence of gene expression (e.g., the absence of an mRNA or polypeptide product encoded by the gene) following the knockout.

Methods of Treatment

In some aspects, methods of the instant disclosure are for treating a hyperproliferative disorder, wherein the methods comprise administering to human subject in need thereof a composition comprising a binding protein specific for human BRAF$^{V600E}$ or a host cell according to the present disclosure.

In certain aspects, the instant disclosure is directed to methods for treating a hyperproliferative disorder or a condition characterized by BRAF$^{V600E}$ expression by administering to human subject in need thereof a composition comprising a binding protein or a host cell expressing a binding protein specific for a BRAF$^{V600E}$ peptide:HLA complex according to any the aforementioned binding proteins.

The presence of a hyperproliferative disorder or malignant condition in a subject refers to the presence of dysplastic, cancerous and/or transformed cells in the subject, including, for example neoplastic, tumor, non-contact inhibited or oncogenically transformed cells, or the like (e.g., solid cancers; hematologic cancers including lymphomas and leukemias, such as acute myeloid leukemia, chronic myeloid leukemia, etc. such as renal, gastric, ovarian, and colorectal cancers), which are known in the art and for which criteria for diagnosis and classification are established (e.g., Hanahan and Weinberg, *Cell* 144:646, 2011; Hanahan and Weinberg, *Cell* 100:57, 2000; Cavallo et al., *Canc. Immunol. Immunother.* 60:319, 2011; Kyrigideis et al., *J. Carcinog.* 9:3, 2010). In particular, for example, hairy cell leukemia, melanoma, non-small cell lung cancer, colorectal cancer, papillary cancer, and thyroid cancer, such as poorly differentiated thyroid cancer. Accordingly, in further embodiments, there are provided methods for treating a hyperproliferative disorder or other condition associated with BRAF$^{V600E}$ expression, including hairy cell leukemia, melanoma, thyroid cancer such as poorly differentiated thyroid cancer, non-small cell lung cancer, colorectal cancer, papillary cancer, non-Hodgkin lymphoma, adenocarcinoma of the lung, and brain tumors including glioblastoma and pilocytic astrocytomas.

As used herein, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide one or more of a binding protein or a BRAF$^{V600E}$ peptide:HLA complex or a host cell expressing the same, and optionally an adjunctive therapy (e.g., a cytokine such as IL-2, IL-15, IL-21 or any combination thereof), in an amount sufficient to provide therapeutic or prophylactic benefit. Therapeutic or prophylactic benefit resulting from therapeutic treatment or prophylactic or preventative methods include, for example an improved clinical outcome, wherein the object is to prevent or retard or otherwise reduce (e.g., decrease in a statistically significant manner relative to an untreated control) an undesired physiological change or disorder, or to prevent, retard or otherwise reduce the expansion or severity of such a disease or disorder. Beneficial or desired clinical results from treating a subject include abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

"Treatment" can also mean prolonging survival when compared to expected survival if a subject were not receiving treatment. Subjects in need of the methods and compositions described herein include those who already have the disease or disorder, as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the compositions (and preparations comprising the compositions) and methods described herein can be evaluated by design and execution of in vitro assays, preclinical studies, and clinical studies in subjects to whom administration of the compositions is intended to benefit, as described in the examples.

Cells expressing the binding protein as described herein may be administered to a subject in a pharmaceutically or physiologically acceptable or suitable excipient or carrier. Pharmaceutically acceptable excipients are biologically compatible vehicles, e.g., physiological saline, which are described in greater detail herein, that are suitable for administration to a human or other non-human mammalian subject.

A therapeutically effective dose, in the context of adoptive cell therapy, is an amount of host cells (expressing a binding protein according to the present disclosure) used in adoptive transfer that is capable of producing a clinically desirable result (i.e., a sufficient amount to induce or enhance a specific T cell immune response against cells expressing $BRAF^{V600E}$ (e.g., a cytotoxic T cell response) in a statistically significant manner) in a treated human or non-human mammal. As is well known in the medical arts, the dosage for any one patient depends upon many factors, including the patient's size, weight, body surface area, age, the particular therapy to be administered, sex, time and route of administration, general health, and other drugs being administered concurrently. Doses will vary, but a preferred dose for administration of a host cell comprising a recombinant expression vector as described herein is about $10^7$ cells/m$^2$, about $5\times10^7$ cells/m$^2$, about $10^8$ cells/m$^2$, about $5\times10^8$ cells/m$^2$, about $10^9$ cells/m$^2$, about $5\times10^9$ cells/m$^2$, about $10^{10}$ cells/m$^2$, about $5\times10^{10}$ cells/m$^2$, or about $10^{11}$ cells/m$^2$.

In any of the presently disclosed embodiments, a unit dose can comprise T cells, e.g., CD4$^+$ T cells, CD8$^+$ T cells, or both, wherein the T cells can comprise bulk T cells, naïve T cells, stem cell memory T cells, central memory T cells, or effector memory T cells. In certain embodiments, a unit dose comprises $BRAF^{V600E}$-specific CD4$^+$ T cells and does not comprise CD8$^+$ T cells. In other embodiments, a unit dose comprises $BRAF^{V600E}$-specific CD8$^+$ T cells, which may be engineered to express a heterologous CD4$^+$ co-receptor, and optionally does not comprise CD4$^+$ T cells. In certain embodiments, a unit dose comprises $BRAF^{V600E}$-specific CD4$^+$ T host cells of the present disclosure and further comprises CD4$^+$ T cells or CD8$^+$ T cells (e.g., allogeneic or autologous, modified (e.g., to express a heterologous protein such as a TCR, a CAR, a CD4 co-receptor, a CD8 co-receptor, or any combination thereof) or unmodified) that have binding specificity for one or more other antigens or antigen-HLA complexes, such as, for example: a $BRAF^{V600E}$ antigen, a BRAF antigen that does not comprise a V600E mutation; a $BRAF^{V600E}$-containing antigen that associates with a different HLA than does the binding protein of a presently disclosed host cell in the unit dose; or a different antigen that is associated with hyperproliferative disease or disorder; e.g., NY-ESO-1, SSX-2, Tyrosinase, TMG1-4, GP100, MAGE-A3, MART1, ROR1, EGFR, EGFRvIII, EGP-2, EGP-40, GD2, GD3, HPV E6, HPV E7, Her2, L1-CAM, Lewis A, Lewis Y, MUC1, MUC16, PSCA, PSMA, CD19, CD20, CD22, CD56, CD23, CD24, CD30, CD33, CD37, CD44v7/8, CD38, CD56, CD123, CA125, c-MET, FcRH5, WT-1, folate receptor α, VEGF-α, VEGFR1, VEGFR2, IL-13Rα2, IL-11Rα, MAGE-A1, PSA, ephrin A2, ephrin B2, an NKG2D, NY-ESO-1, TAG-72, mesothelin, NY-ESO, 5T4, BCMA, FAP, Carbonic anhydrase 9, ERBB2, or CEA, or any combination thereof).

In certain embodiments, a unit dose comprises (i) a composition comprising at least about 30%, at least about 40%, at least about 50%, at least about 60%, at least about 70%, at least about 80%, at least about 85%, at least about 90%, or at least about 95% engineered CD4$^+$ T cells, combined with (ii) a composition comprising at least about 30%, at least about 40%, at least about 50%, at least about 60%, at least about 70%, at least about 80%, at least about 85%, at least about 90%, or at least about 95% engineered CD8$^+$ T cells, in about a 1:1 ratio, wherein the unit dose contains a reduced amount or substantially no naïve T cells (i.e., has less than about 50%, less than about 40%, less than about 30%, less than about 20%, less than about 10%, less than about 5%, or less then about 1% the population of naïve T cells present in a unit dose as compared to a patient sample having a comparable number of PBMCs).

In some embodiments, a unit dose comprises (i) a composition comprising at least about 50% engineered CD4$^+$ T cells, combined with (ii) a composition comprising at least about 50% engineered CD8$^+$ T cells, in about a 1:1 ratio, wherein the unit dose contains a reduced amount or substantially no naïve T cells. In further embodiments, a unit dose comprises (i) a composition comprising at least about 60% engineered CD4$^+$ T cells, combined with (ii) a composition comprising at least about 60% engineered CD8$^+$ T cells, in about a 1:1 ratio, wherein the unit dose contains a reduced amount or substantially no naïve T cells. In still further embodiments, a unit dose comprises (i) a composition comprising at least about 70% engineered CD4$^+$ T cells, combined with (ii) a composition comprising at least about 70% engineered CD8$^+$ T cells, in about a 1:1 ratio, wherein the unit dose contains a reduced amount or substantially no naïve T cells. In some embodiments, a unit dose comprises (i) a composition comprising at least about 80% engineered CD4$^+$ T cells, combined with (ii) a composition comprising at least about 80% engineered CD8$^+$ T cells, in about a 1:1 ratio, wherein the unit dose contains a reduced amount or substantially no naïve T cells. In some embodiments, a unit dose comprises (i) a composition comprising at least about 85% engineered CD4$^+$ T cells, combined with (ii) a composition comprising at least about 85% engineered CD8$^+$ T cells, in about a 1:1 ratio, wherein the unit dose contains a reduced amount or substantially no naïve T cells. In some embodiments, a unit dose comprises (i) a composition comprising at least about 90% engineered CD4$^+$ T cells, combined with (ii) a composition comprising at least about 90% engineered CD8$^+$ T cells, in about a 1:1 ratio, wherein the unit dose contains a reduced amount or substantially no naïve T cells.

In any of the embodiments described herein, a unit dose comprises equal, or approximately equal numbers of engineered CD45RA$^-$ CD3$^+$ CD8$^+$ and engineered CD45RA$^-$ CD3$^+$ CD4$^+$ T$_M$ cells.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's disease, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

A condition associated with BRAF$^{V600E}$ expression includes any disorder or condition in which a BRAF$^{V600E}$-driven cellular or molecular event is present, and typically manifests in overgrowth of diseased cells relative to normal cells. Some conditions associated with BRAF$^{V600E}$ expression may include acute as well as chronic disorders and diseases, such as those pathological conditions that predispose the subject to a particular disorder.

Some examples of conditions associated with BRAF$^{V600E}$ expression include hyperproliferative disorders, which refer to states of activated and/or proliferating cells (which may also be transcriptionally overactive) in a subject including tumors, neoplasms, cancer, malignancy, etc. In addition to activated or proliferating cells, the hyperproliferative disorder may also include an aberration or dysregulation of cell death processes, whether by necrosis or apoptosis. Such aberration of cell death processes may be associated with a variety of conditions, including cancer (including primary, secondary malignancies as well as metastasis), or other conditions.

According to certain embodiments, a cancer that is characterized by BRAF$^{V600E}$ expression may be treated through the use of compositions and methods disclosed herein. Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer. Also contemplated within the presently disclosed embodiments are specific embodiments wherein only one of the above types of disease is included, or where specific conditions may be excluded regardless of whether or not they are characterized by BRAF$^{V600E}$ expression.

Certain methods of treatment or prevention contemplated herein include administering a host cell (which may be autologous, allogeneic or syngeneic) comprising a desired polynucleotide as described herein that is stably integrated into the chromosome of the cell. For example, such a cellular composition may be generated ex vivo using autologous, allogeneic or syngeneic immune system cells (e.g., T cells, antigen-presenting cells, natural killer cells) in order to administer a desired, BRAF$^{V600E}$-targeted T-cell composition to a subject as an adoptive immunotherapy. In certain embodiments, the host cell is a hematopoietic progenitor cell or a human immune cell. In certain embodiments, the immune system cell is a CD4$^+$ T cell, a CD8$^+$ T cell, a CD4$^-$ CD8$^-$ double-negative T cell, a γδ T cell, a natural killer cell, a natural killer T cell, a dendritic cell, or any combination thereof. In certain embodiments, the immune system cell is a naïve T cell, a central memory T cell, a stem cell memory T cell, an effector memory T cell, or any combination thereof. In particular embodiments, the cell is a CD4$^+$ T cell.

As used herein, administration of a composition or therapy refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., BRAF$^{V600E}$-specific recombinant (i.e., engineered) host cells with one or more cytokines; immunosuppressive therapy such as calcineurin inhibitors, corticosteroids, microtubule inhibitors, low dose of a mycophenolic acid prodrug, or any combination thereof).

In certain embodiments, a plurality of doses of a recombinant host cell as described herein is administered to the subject, which may be administered at intervals between administrations of about two to about four weeks. In further embodiments, a cytokine (e.g., IL-2, IL-15, IL-21) is administered sequentially, provided that the subject was administered the recombinant host cell at least three or four times before cytokine administration. In certain embodiments, the cytokine is administered concurrently with the host cell. In certain embodiments, the cytokine is administered subcutaneously.

In still further embodiments, the subject being treated is further receiving immunosuppressive therapy, such as calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant.

An effective amount of a therapeutic or pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

The level of a CTL immune response may be determined by any one of numerous immunological methods described herein and routinely practiced in the art. The level of a CTL immune response may be determined prior to and following administration of any one of the herein described BRAF$^{V600E}$-specific binding proteins expressed by, for example, a T cell. Cytotoxicity assays for determining CTL activity may be performed using any one of several techniques and methods routinely practiced in the art (see, e.g., Henkart et al., "Cytotoxic T-Lymphocytes" in *Fundamental Immunology*, Paul (ed.) (2003 Lippincott Williams & Wilkins, Philadelphia, PA), pages 1127-50, and references cited therein).

Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response to a BRAF$^{V600E}$-containing antigen peptide as described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

The pharmaceutical compositions described herein may be presented in unit-dose or multi-dose containers, such as sealed ampoules or vials. Such containers may be frozen to preserve the stability of the formulation until. In certain embodiments, a unit dose comprises a recombinant host cell as described herein at a dose of about $10^7$ cells/m$^2$ to about $10^{11}$ cells/m$^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polyethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of recombinant cells or active compound calculated to produce the desired therapeutic effect in association with an appropriate pharmaceutical carrier.

In general, an appropriate dosage and treatment regimen provides the active molecules or cells in an amount sufficient to provide therapeutic or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

In still further aspects, unit dose forms comprising host cells according to the present disclosure are provided.

Methods according to this disclosure may further include administering one or more additional agents to treat the disease or disorder in a combination therapy. For example, in certain embodiments, a combination therapy comprises administering a BRAF$^{V600E}$-specific binding protein (or an engineered host cell expressing the same) with (concurrently, simultaneously, or sequentially) an immune checkpoint inhibitor. In some embodiments, a combination therapy comprises administering a BRAF$^{V600E}$-specific binding protein of the present disclosure (or an engineered host cell expressing the same) with an agonist of a stimulatory immune checkpoint agent. In further embodiments, a combination therapy comprises administering a BRAF$^{V600E}$-specific binding protein of the present disclosure (or an engineered host cell expressing the same) with a secondary therapy, such as chemotherapeutic agent, a radiation therapy, a surgery, an antibody, or any combination thereof.

As used herein, the term "immune suppression agent" or "immunosuppression agent" refers to one or more cells, proteins, molecules, compounds or complexes providing inhibitory signals to assist in controlling or suppressing an immune response. For example, immune suppression agents include those molecules that partially or totally block immune stimulation; decrease, prevent or delay immune activation; or increase, activate, or up regulate immune suppression. Exemplary immunosuppression agents to target (e.g., with an immune checkpoint inhibitor) include PD-1, PD-L1, PD-L2, LAG3, CTLA4, B7-H3, B7-H4, CD244/2B4, HVEM, BTLA, CD160, TIM3, GAL9, KIR, PVR1G (CD112R), PVRL2, adenosine, A2aR, immunosuppressive cytokines (e.g., IL-10, IL-4, IL-1RA, IL-35), IDO, arginase, VISTA, TIGIT, LAIR1, CEACAM-1, CEACAM-3, CEACAM-5, Treg cells, or any combination thereof.

An immune suppression agent inhibitor (also referred to as an immune checkpoint inhibitor) may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments disclosed herein, a method may comprise administering a BRAF$^{V600E}$-specific binding protein of the present disclosure (or an engineered host cell expressing the same) with one or more inhibitor of any one of the following immune suppression components, singly or in any combination.

In certain embodiments, a BRAF$^{V600E}$-specific binding protein is used in combination with a PD-1 inhibitor, for example a PD-1-specific antibody or binding fragment thereof, such as pidilizumab, nivolumab (Keytruda, formerly MDX-1106), pembrolizumab (Opdivo, formerly MK-3475), MEDI0680 (formerly AMP-514), AMP-224, BMS-936558 or any combination thereof. In further embodiments, a BRAF$^{V600E}$-specific binding protein of the present disclosure (or an engineered host cell expressing the same) is used in combination with a PD-L1 specific antibody or binding fragment thereof, such as BMS-936559, durvalumab (MEDI4736), atezolizumab (RG7446), avelumab (MSB0010718C), MPDL3280A, or any combination thereof.

In certain embodiments, a BRAF$^{V600E}$-specific binding protein of the present disclosure (or an engineered host cell expressing the same) is used in combination with a LAG3 inhibitor, such as LAG525, IMP321, IMP701, 9H12, BMS-986016, or any combination thereof.

In certain embodiments, a BRAF$^{V600E}$-specific binding protein is used in combination with an inhibitor of CTLA4. In particular embodiments, a BRAF$^{V600E}$-specific binding protein of the present disclosure (or an engineered host cell expressing the same) is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, a BRAF$^{V600E}$-specific binding protein of the present disclosure (or an engineered host cell expressing the same) is used in combination with a B7-H3 specific antibody or binding fragment thereof, such as enoblituzumab (MGA271), 376.96, or both. A B7-H4 antibody binding fragment may be a scFv or fusion protein thereof, as described in, for example, Dangaj et al., *Cancer Res.* 73:4820, 2013, as well as those described in U.S. Pat. No. 9,574,000 and PCT Patent Publication Nos. WO/201640724A1 and WO 2013/025779A1.

In certain embodiments, a BRAF$^{V600E}$-specific binding protein of the present disclosure (or an engineered host cell expressing the same) is used in combination with an inhibitor of CD244.

In certain embodiments, a BRAF$^{V600E}$-specific binding protein of the present disclosure (or an engineered host cell expressing the same) is used in combination with an inhibitor of BLTA, HVEM, CD160, or any combination thereof. Anti CD-160 antibodies are described in, for example, PCT Publication No. WO 2010/084158.

In certain embodiments, a BRAF$^{V600E}$-specific binding protein of the present disclosure (or an engineered host cell expressing the same) is used in combination with an inhibitor of TIM3.

In certain embodiments, a BRAF$^{V600E}$-specific binding protein of the present disclosure (or an engineered host cell expressing the same) is used in combination with an inhibitor of Gal9.

In certain embodiments, a BRAF$^{V600E}$-specific binding protein of the present disclosure (or an engineered host cell expressing the same) is used in combination with an inhibitor of adenosine signaling, such as a decoy adenosine receptor.

In certain embodiments, a BRAF$^{V600E}$-specific binding protein of the present disclosure (or an engineered host cell expressing the same) is used in combination with an inhibitor of A2aR.

In certain embodiments, a BRAF$^{V600E}$-specific binding protein of the present disclosure (or an engineered host cell expressing the same) is used in combination with an inhibitor of KIR, such as lirilumab (BMS-986015).

In certain embodiments, a BRAF$^{V600E}$-specific binding protein of the present disclosure (or an engineered host cell expressing the same) is used in combination with an inhibitor of an inhibitory cytokine (typically, a cytokine other than TGFβ) or Treg development or activity.

In certain embodiments, a BRAF$^{V600E}$-specific binding protein of the present disclosure (or an engineered host cell expressing the same) is used in combination with an IDO inhibitor, such as levo-1-methyl tryptophan, epacadostat (INCB024360; Liu et al., *Blood* 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, a BRAF$^{V600E}$-specific binding protein of the present disclosure (or an engineered host cell expressing the same) is used in combination with an arginase inhibitor, such as N(omega)-Nitro-L-arginine methyl ester (L-NAME), N-omega-hydroxy-nor-l-arginine (nor-NOHA), L-NOHA, 2(S)-amino-6-boronohexanoic acid (ABH), S-(2-boronoethyl)-L-cysteine (BEC), or any combination thereof.

In certain embodiments, a BRAF$^{V600E}$-specific binding protein of the present disclosure (or an engineered host cell expressing the same) is used in combination with an inhibitor of VISTA, such as CA-170 (Curis, Lexington, Mass.).

In certain embodiments, a BRAF$^{V600E}$-specific binding protein of the present disclosure (or an engineered host cell expressing the same) is used in combination with an inhibitor of TIGIT such as, for example, COM902 (Compugen, Toronto, Ontario Canada), an inhibitor of CD155, such as, for example, COM701 (Compugen), or both.

In certain embodiments, a BRAF$^{V600E}$-specific binding protein of the present disclosure (or an engineered host cell expressing the same) is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, a BRAF$^{V600E}$-specific binding protein of the present disclosure (or an engineered host cell expressing the same) is used in combination with a LAIR1 inhibitor.

In certain embodiments, a BRAF$^{V600E}$-specific binding protein of the present disclosure (or an engineered host cell expressing the same) is used in combination with an inhibitor of CEACAM-1, CEACAM-3, CEACAM-5, or any combination thereof.

In certain embodiments, a BRAF$^{V600E}$-specific binding protein of the present disclosure (or an engineered host cell expressing the same) is used in combination with an agent that increases the activity (i.e., is an agonist) of a stimulatory immune checkpoint molecule. For example, a BRAF$^{V600E}$-specific binding protein of the present disclosure (or an engineered host cell expressing the same) can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering a BRAF$^{V600E}$-specific binding protein of the present disclosure (or an engineered host cell expressing the same) with one or more agonist of a stimulatory immune checkpoint molecule, including any of the foregoing, singly or in any combination.

In certain embodiments, a combination therapy comprises a BRAF$^{V600E}$-specific binding protein of the present disclosure (or an engineered host cell expressing the same) and a secondary therapy comprising one or more of: an antibody or antigen binding-fragment thereof that is specific for a cancer antigen expressed by the non-inflamed solid tumor, a radiation treatment, a surgery, a chemotherapeutic agent, a cytokine, RNAi, or any combination thereof.

In certain embodiments, a combination therapy method comprises administering a BRAF$^{V600E}$-specific binding protein and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer or non-inflamed solid tumor in a subject are well-known to those of ordinary skill in the art.

In certain embodiments, a combination therapy method comprises administering a BRAF$^{V600E}$-specific binding protein of the present disclosure (or an engineered host cell expressing the same) and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers, toxins such as Cholera toxin, ricin, Pseudomonas exotoxin, Bordetella pertussis adenylate cyclase toxin, or diphtheria toxin, and caspase activators; and chromatin disruptors.

Cytokines are increasingly used to manipulate host immune response towards anticancer activity. See, e.g., Floros & Tarhini, *Semin. Oncol.* 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with the binding proteins or cells expressing the same of this disclosure.

Another cancer therapy approach involves reducing expression of oncogenes and other genes needed for growth, maintenance, proliferation, and immune evasion by cancer cells. RNA interference, and in particular the use of microRNAs (miRNAs) and small inhibitory RNAs (siRNAs) provides an approach for knocking down expression of cancer genes (see, e.g., Larsson et al., *Cancer Treat. Rev.* 16(55): 128-135, 2017), which can be used in combination with the binding proteins or cells expressing the same of this disclosure.

In any of the embodiments disclosed herein, any of the therapeutic agents (e.g, a BRAF$^{V600E}$-specific binding protein or engineered host cell, an inhibitor of an immune suppression component, an agonist of a stimulatory immune checkpoint molecule, an antitumor lymphocyte, a chemotherapeutic agent, a radiation therapy, a surgery, a cytokine, or an inhibitory RNA) may be administered once or more than once to the subject over the course of a treatment, and, in combinations, may be administered to the subject in any order or any combination. An appropriate dose, suitable duration, and frequency of administration of a therapeutic agent will be determined by such factors as a condition of the patient; size, type, spread, growth, and severity of the tumor or cancer; particular form of the active ingredient; and the method of administration.

EXAMPLES

Example 1

Identification of CD4+ BRAF$^{V600E}$-Specific T Cells in a Melanoma Patient

A 52-year-old man presented with stage IIIC, BRAF$^{V600E}$-mutated melanoma originating on the left foot and was treated with wide excision, lymph node dissection and adjuvant ipilimumab. Shortly before completing one year of ipilimumab, he required resection of three in-transit metastases in his left leg, and an additional in-transit metastasis 3 months later. He subsequently progressed with a 3 cm left iliac nodal metastasis and soft tissue nodular FDG avid lesion in the left thigh (FIG. 1A). The iliac node was resected for whole exome sequencing and expansion of TIL, and the patient subsequently received TIL infusion following lymphodepleting chemotherapy. The left thigh lesion resolved and the patient remains free of disease 27 months after therapy.

Whole exome and RNA sequencing of purified tumor cells and normal tissue identified only 20 nonsynonymous missense mutations, shown in Table 1: (columns 2 and 3 from left); columns 4-6 from left: 27-mer peptides encompassing the encoded nonsynonymous mutations and the presence of the mutation in DNA or RNA-Seq (columns 4-6 from left); (columns 7 and 8 from left) engineered 20-mer peptides comprising the mutation; and RNA-seq expression in units of transcripts per million (TPM).

TABLE 1

Nonsynonymous Mutations in Purified Tumor Cells and Normal Tissue from a Melanoma Patient

| symbol | sub.nt | sub.aa | 27-mer aa sequence | Mut'n in DNA | Mut'n in RNA | 20-mer peptide 1 | 20-mer peptide 2 | TPM in RNA |
|---|---|---|---|---|---|---|---|---|
| AP1M1 | AP1M1.A>C | p.I295L | VIEKHSHSRI EYMLKAKSQ FKRRSTAN (SEQ ID NO: 79) | yes | yes | VIEKHSHS RIEYMLK AKSQF (SEQ ID NO: 80) | SRIEYML KAKSQFK RRSTAN SEQ ID NO: 81) | 61.33 |
| BRAF | BRAF.A>T | p.V600E | DLTVKIGDF GLATEKSRW SGSHQFEQL (SEQ ID NO: 37) | yes | yes | DLTVKIG DFGLATE KSRWSG (SEQ ID NO: 38) | DFGLA KSRWSGE HQFEQL (SEQ ID NO: 39) | 10.83 |
| DCAF6 | DCAF6.G>A | p.A419T | EQFLQPSTSS TMSTQAHST SSPTESPH (SEQ ID NO: 82) | yes | yes | EQFLQPST SSTMSTQ AHSTS (SEQ ID NO: 83) | TSSTMST QAHSTSS PTESPH (SEQ ID NO: 84) | 41.11 |
| GTF2H4 | GTF2H4.C>T | p.T319M | FIVVETNYRL YAYMESELQ IALIALFS (SEQ ID NO: 85) | yes | yes | FIVVETN YRLYAY MESELQI (SEQ ID NO: 86) | YRLYAY MESELQI ALIALFS (SEQ ID NO: 87) | 49.95 |
| NBPF12 | NBPF12.A>Gp. | E2471G | DSCQPYRSSF YALGEKHVG FSLDVGEI (SEQ ID NO: 88) | yes | yes | DSCQPYR SSFYALG EKHVGF (SEQ ID NO: 89) | SSFYALG EKHVGFS LDVGEI (SEQ ID NO: 90) | 12.5 |
| ORC3 | ORC3.A>C | p.I236L | ESFATKVLQ DFIILSSQHL HEFPLILI (SEQ ID NO: 91) | yes | yes | ESFATKV LQDFIILS SQHLH (SEQ ID NO: 92) | LQDFIILS SQHLHEF PLILI (SEQ ID NO: 93) | 19.92 |
| ROR1 | ROR1.A>G | p.N53S | LVPTSSWNIS SELSKDSYLT LDEPMNN (SEQ ID NO: 94) | yes | yes | LVPTSSW NISSELSK DSYLT (SEQ ID NO: 95) | NISSELSK DSYLTLD EPMNN (SEQ ID NO: 96) | 4.69 |
| SF3B1 | ZNF700.T>G | p.T358A | QMGGSTPVL TPGKAPIGTP AMNMATPT (SEQ ID NO: 97) | yes | yes | QMGGSTP VLTPGKA PIGTPA (SEQ ID NO: 98) | VLTPGKA PIGTPAM NMATPT (SEQ ID NO: 99) | 105.2 |

TABLE 1-continued

Nonsynonymous Mutations in Purified Tumor Cells and Normal Tissue from a Melanoma Patient

| symbol | sub.nt | sub.aa | 27-mer aa sequence | Mut'n in DNA | Mut'n in RNA | 20-mer peptide 1 | 20-mer peptide 2 | TPM in RNA |
|---|---|---|---|---|---|---|---|---|
| UNKL | UNKL.C>T | p.V154I | AHGPLDLRPPVCDIRELQAQEALQNGQ (SEQ ID NO: 100) | yes | yes | AHGPLDLRPPVCDIRELQAQ (SEQ ID NO: 101) | RPPVCDIRELQAQEALQNGQ (SEQ ID NO: 102) | 6.72 |
| ZNF700 | ZNF700.T>G | p.F287L | GEKPYECSKCDKALHSSSSYHRHERSH (SEQ ID NO: 103) | yes | yes | GEKPYECSKCDKALHSSSSY (SEQ ID NO: 104) | SKCDKALHSSSSYHRHERSH (SEQ ID NO: 105) | 8.69 |
| NVL | NVL.T>G | p.T370P | APCIIFIDEIDAIPPKREVASKDMERR (SEQ ID NO: 106) | yes | yes | APCIIFIDEIDAIPPKREVA (SEQ ID NO: 107) | DEIDAIPPKREVASKDMERR (SEQ ID NO: 108) | 18.42 |
| MATN1 | MATN1.T>G | p.T153P | SRSPDISKVVIVVPDGRPQDSVQDVSA (SEQ ID NO: 109) | yes | yes | SRSPDISKVVIVVPDGRPQD (SEQ ID NO: 110) | KVVIVVPDGRPQDSVQDVSA (SEQ ID NO: 111) | 0.14 |
| CTNNA2 | CTNNA2.A>C | p.N351H | VRQALQDLLSEYMHNTGRKEKGDPLNI (SEQ ID NO: 112) | yes | no | VRQALQDLLSEYMHNTGRKE (SEQ ID NO: 113) | LLSEYMHNTGRKEKGDPLNI (SEQ ID NO: 114) | 2.36 |
| GET4 | GET4.T>G | p.L65R | RYMSQSKHTEARERMYSGALLFFSHGQ (SEQ ID NO: 115) | yes | no | RYMSQSKHTEARERMYSGAL (SEQ ID NO: 116) | HTEARERMYSGALLFFSHGQ (SEQ ID NO: 117) | 26.97 |
| NTNG1 | NTNG1.G>A | p.V271I | TVTDLRIRLLRPAIGEIFVDELHLARY (SEQ ID NO: 118) | yes | yes | TVTDLRIRLLRPAIGEIFVD (SEQ ID NO: 119) | RLLRPAIGEIFVDELHLARY (SEQ ID NO: 120) | 0.73 |
| SPTBN5 | SPTBN5.G>A | p.T3127I | TLLLDAWLTTKAAIAESQDYGQDLEGV (SEQ ID NO: 121) | yes | yes | TLLLDAWLTTKAAIAESQDY (SEQ ID NO: 122) | LTTKAAIAESQDYGQDLEGV (SEQ ID NO: 123) | 1.11 |
| DPP6 | DPP6.C>T | p.5113L | LLVILVICSLIVTLVILLTPAEDNSLS (SEQ ID NO: 124) | yes | no | LLVILVICSLIVTLVILLTP (SEQ ID NO: 125) | CSLIVTLVILLTPAEDNSLS (SEQ ID NO: 126) | 0.03 |
| HIAT1 | HIAT1.G>T | p.G93C | VKGLLSFLSAPLICALSDVWGRKSFLL (SEQ ID NO: 127) | yes | no | VKGLLSFLSAPLICALSDVW (SEQ ID NO: 128) | LSAPLICALSDVWGRKSFLL (SEQ ID NO: 129) | 46.71 |
| ITGA4 | ITGA4.G>T | p.V359F | GSGAVMNAMETNLFGSDKYAARFGESI (SEQ ID NO: 130) | yes | no | GSGAVMNAMETNLFGSDKYA (SEQ ID NO: 131) | AMETNLFGSDKYAARFGESI (SEQ ID NO: 132) | 4.59 |
| MYO1A | MYO1A.C>T | p.V1017I | SVRFKENSVAVKVIQGPAGGDNSKLRY (SEQ ID NO: 133) | yes | no | SVRFKENSVAVKVIQGPAGG (SEQ ID NO: 134) | SVAVKVIQGPAGGDNSKLRY (SEQ ID NO: 135) | 0.05 |

Also determined, but not shown in Table 1, were chromosomal positions (using GRCh37/hg19 reference assembly) and the variant allele frequency (VAF) for each mutation. The VAF for the BRAF$^{V600E}$ mutation was 35.4%.

Figure 1B:
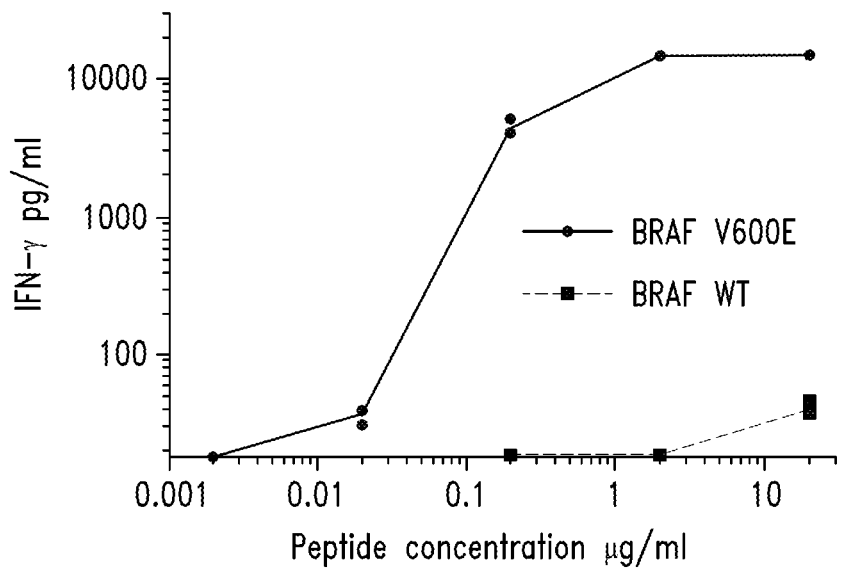
Figure 1C:
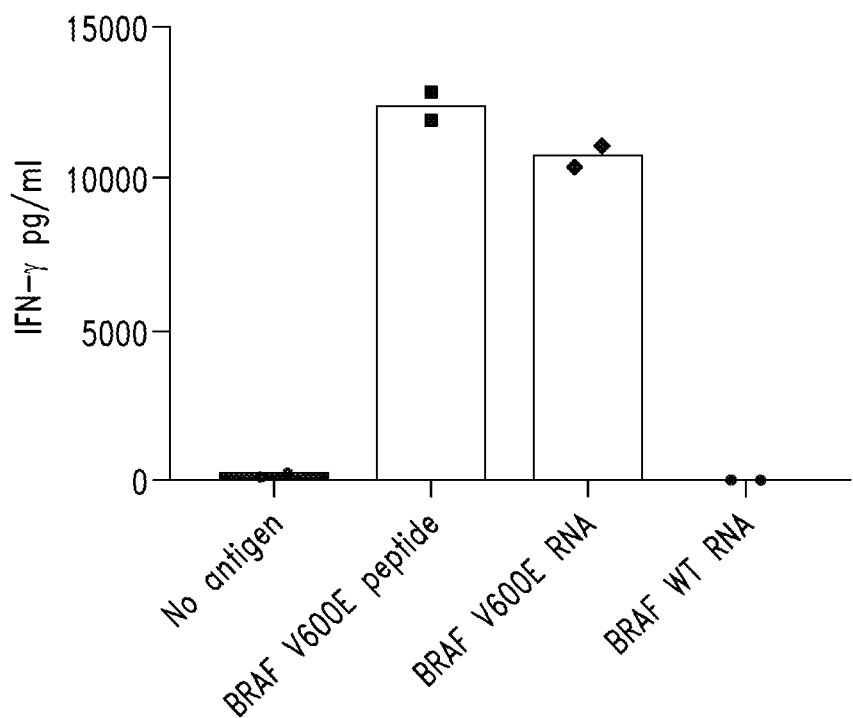

T cell responses to these potential neoantigens were evaluated by stimulating peripheral blood mononuclear cells (PBMC) obtained from the patient after TIL therapy with a pool of peptides flanking each of the 20 mutations. No CD8$^+$ T cell responses to the candidate neoantigens were detected; however, a CD4$^+$ T cell response specific for 20-mer peptides encompassing BRAF$^{V600E}$ was identified. The BRAF$^{V600E}$-reactive cells were purified by IFN-γ capture and shown to recognize autologous B cells pulsed with mutant but not wildtype BRAF peptide, confirming specificity for the mutant peptide (FIG. 1B). To determine whether BRAF$^{V600E}$ is processed and presented by class II MHC$^+$ APC, autologous B cells were transfected with mRNA encoding wildtype or mutant BRAF sequences targeted to the endosome. The T cells recognized B cells expressing mutant, but not wildtype BRAF (FIG. 1C).

Figure 1D:
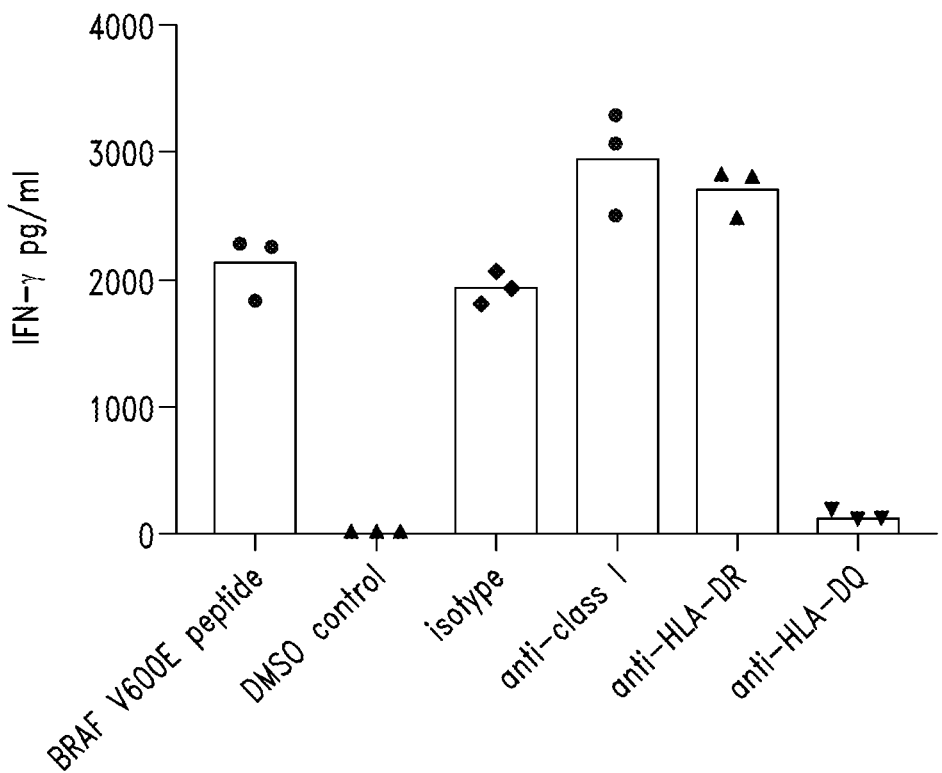

Recognition was blocked by anti-HLA-DQ but not anti-class I or anti HLA-DR antibodies, identifying HLA-DQ as the likely restricting allele (FIG. 1D). Analysis of multiple B cell lines of known genotype suggested restriction by HLA-DQA1*03 paired with HLA-DQB1*03, with weak recognition of DQB1*0301 and stronger recognition of DQB1*0302 and DQB1*0303 (FIG. 1F and Table 2).

TABLE 2

IFN-γ production by BRAF$^{V600E}$-specific CD4+ T cells following incubation with allogeneic B-LCL cell lines expressing different class II alleles and in the presence or absence of antigen.

| Cell line | BRAF V600E Peptide | Mean IFN-G pg/ml | HLA DRB1 | HLA DQB1 |
|---|---|---|---|---|
| 1331 | − | 10 | 404 | 302 |
|  | + | 41791 |  |  |
| CFS | − | 10 | 0401, 0101 | 0301, 0501 |
|  | + | 1547 |  |  |
| DEM | − | 23 | 0401, 1602 | 0302, 0502 |
|  | + | 29873 |  |  |
| DEU | − | 6 | 401 | 301 |
|  | + | 10359 |  |  |
| FAL | − | 9 | 0403, 0801 | 03BG, 0402 |
|  | + | 31620 |  |  |
| BM14 | − | 536 | 401 | 302 |
|  | + | 42832 |  |  |
| DMB | − | 38 | 0101, 1501 | 0501, 0602 |
|  | + | 7 |  |  |
| DLM | − | 26 | 0403, 0801 | 03BG, 0402 |
|  | + | 39388 |  |  |

TABLE 2-continued

IFN-γ production by BRAF$^{V600E}$-specific CD4+ T cells following incubation with allogeneic B-LCL cell lines expressing different class II alleles and in the presence or absence of antigen.

| Cell line | BRAF V600E Peptide | Mean IFN-G pg/ml | HLA DRB1 | HLA DQB1 |
|---|---|---|---|---|
| AMM | − | 6 | 0802, 1501 | 0402, 06WG |
|  | + | 9 |  |  |
| CLC | − | 9 | 0301, 1104 | 02AB, 0301 |
|  | + | 6 |  |  |
| BP | − | 35 | 1601, 1101 | 0502, 0301 |
|  | + | 36 |  |  |
| JWP | − | 12 | 0701, 0701 | 02AB, 0303 |
|  | + | 359 |  |  |
| DAH2 | − | 17 | 09, 1501 | 0303, 06W6 |
|  | + | 49784 |  |  |
| VRM | − | 6 | 0701, 10 | 0303, 0501 |
|  | + | 188 |  |  |

The complete patient HLA typing was as follows: A*11:01:01/A*24:02:01; B*15:01:01/B*40:01:02; C*03:03:01/C*03:04:01; DPA1*01:03:01/DPA1*01:03:01; DPB1*04:01:01/DPB1*04:01:01; DQA1*03:01:01/DQA1*03:02; DQB1*03:02:01/DQB1*03:03:02; DRB1*04:03:01/DRB1*09:01:02; DRB4*01:03:01/DRB4*01:03:02.

Figure 1E:
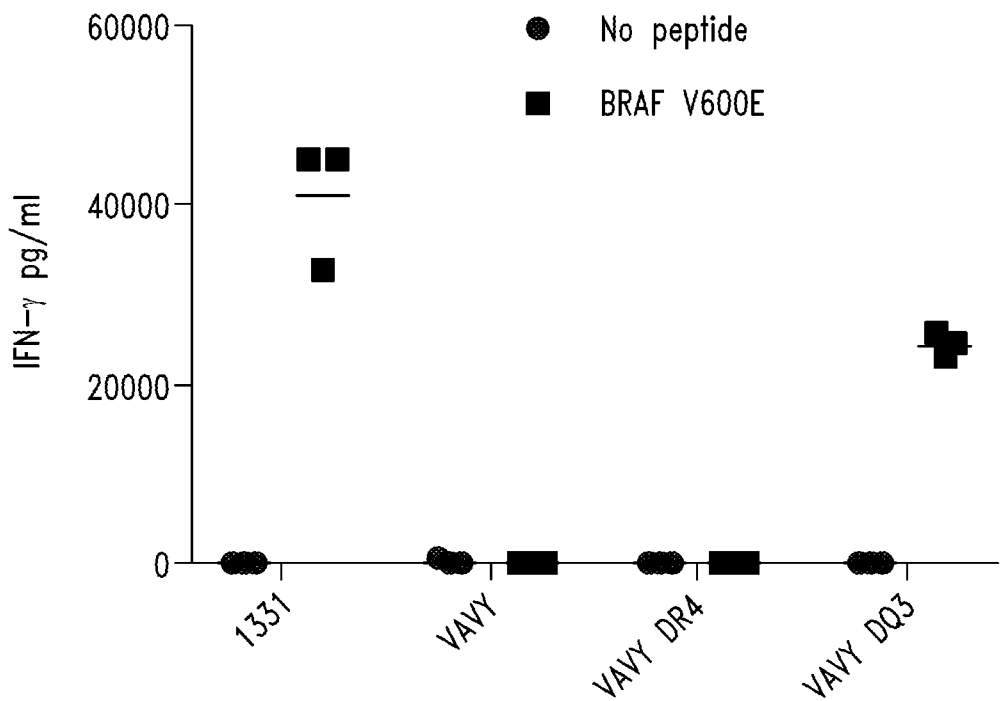
Figure 1F:
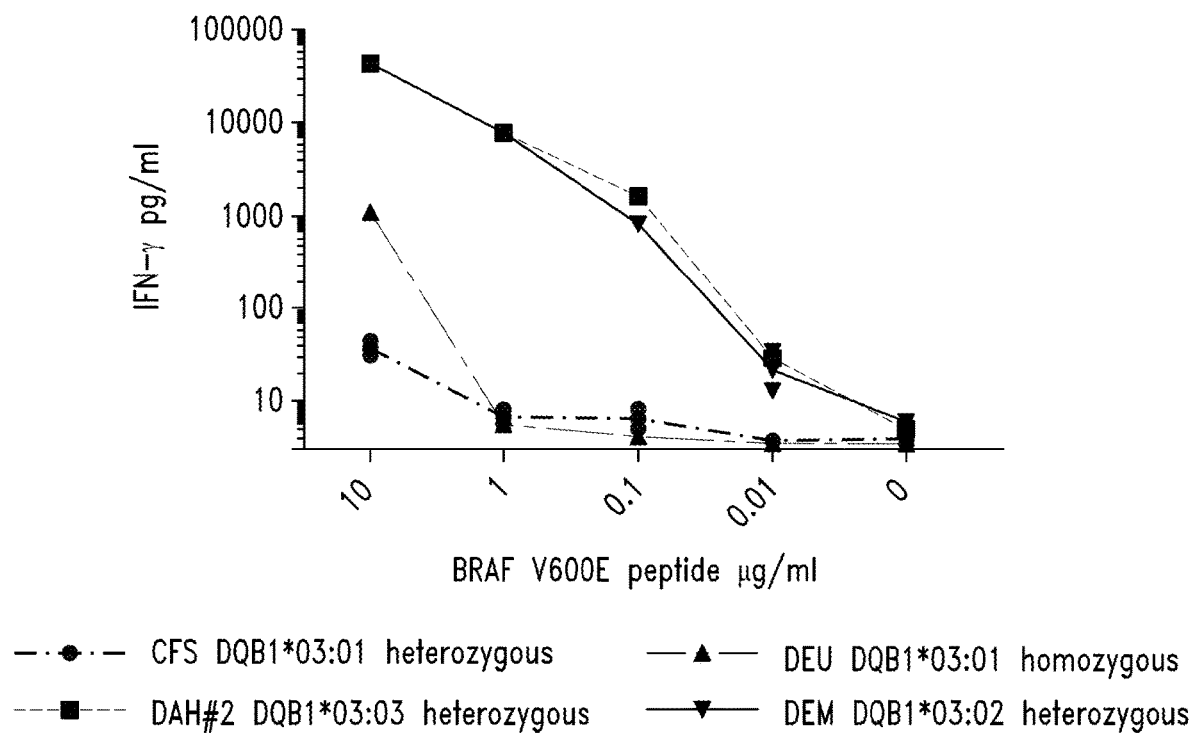

B-LCL transfected with HLA-DQA1*03 or DQB1*0302, but not the closely linked HLA-DRB1*04, were recognized by BRAF$^{V600E}$-specific CD4$^+$ T cells when pulsed with the mutant peptide, confirming the HLA restriction (FIG. 1E).

Figure 1G:
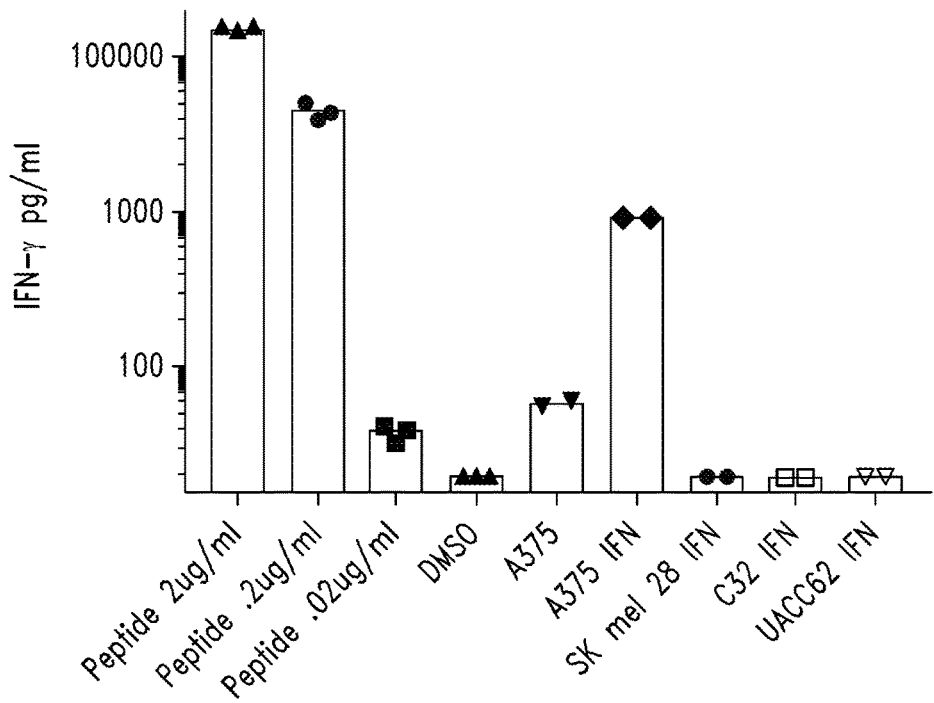
Figure 1H:
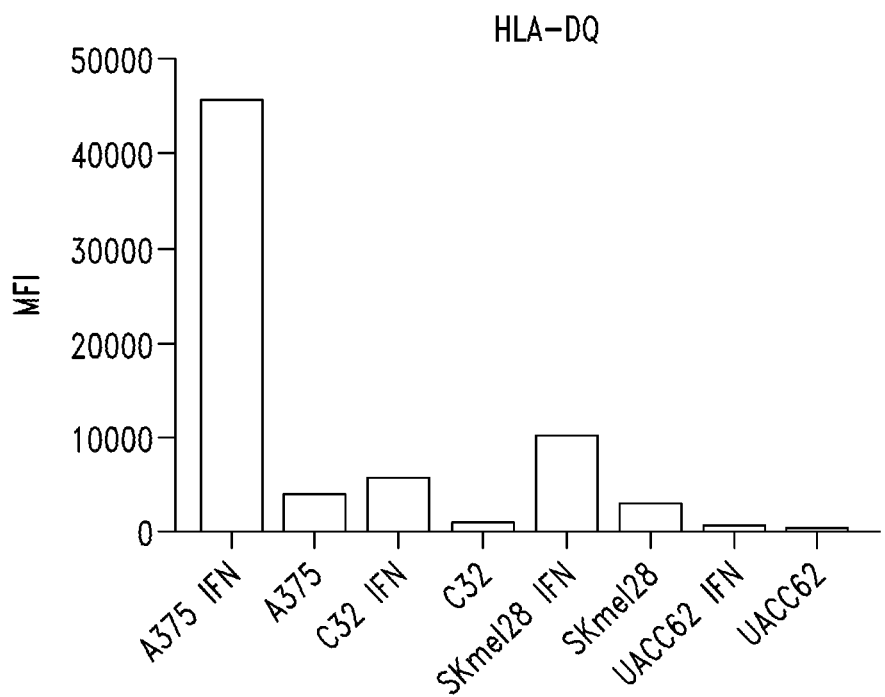
Figure 1I:
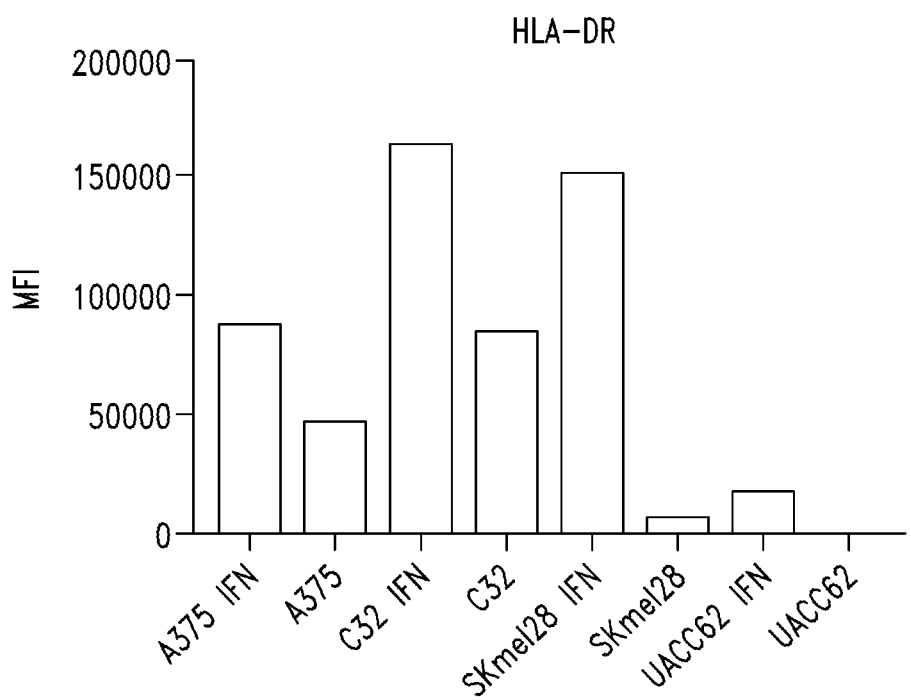

Recognition of three melanoma cell lines with an HLA-DQB1*0302 and BRAF$^{V600E}$ genotype was tested. One tumor cell line that expressed the greatest amount of HLA-DQ was recognized by the BRAF$^{V600E}$-specific CD4$^+$ T cells demonstrating that the epitope can be presented directly by tumor cells (FIGS. 1G-1I). Tumor-specific CD4$^+$ T cells can have anti-tumor activity through direct cell killing and cytokine release (see, e.g., Quezada et al., *J. Exp. Med.* 207(3):637-650 (2010); Manici et al., *J. Exp. Med.* 189(5):871-876 (1999)), but a major role is to support the development and function of CD8$^+$ T cells by licensing APC and producing cytokines (see, e.g., Sun and Bevan, *Science* 300(5617):339-342 (2003); Williams et al., *Nature* 441 (7095):890-893 (2006)). Although adoptively transferred TIL contained BRAF$^{V600E}$-specific CD4$^+$ T cells, CD8$^+$ T cells were the prevalent population in TIL (Table 3). Briefly, the final TIL product infused into the patient was analyzed by flow cytometry for phenotype and, following stimulation with PMA/Ionomycin, was stained intracellularly for cytokines. Percentages shown in Table 3 are percentages of CD45+ cells (top) or CD4 or CD8 cells (bottom)

TABLE 3

Phenotype of Final TIL product

| % of live | % of CD45 | | | | | |
|---|---|---|---|---|---|---|
| CD45 | CD3 T | Γδ T | NKT | CD8T | CD4T | Treg |
| 99.9 | 99.7 | 0.04 | 0.014 | 93.9 | 3.4 | 0.52 |

| % of CD45 | | | | | |
|---|---|---|---|---|---|
| CD8P1 | CD8 TIM3 | CD8 TM | CD8 naïve | CD8 EMRA | CD8EM |
| 51.6 | 93.4 | 0.002 | 0.003 | 36.5 | 58.6 |

TABLE 3-continued

| Phenotype of Final TIL product | | | |
|---|---|---|---|
| % of CD8 or CD4 | | | |
| CD8 IFN-γ+ | CD4 IL17+ | CD4 IL22 | CD4 IFN-γ+ |
| 99.3 | 3.6 | 0.42 | 98.8 |

Moreover, a majority of IFN-γ produced by stimulation of multiple independent TIL cultures with autologous tumor was blocked by a HLA class I blocking antibody (Table 4).

TABLE 4

Tumor specificity and class I blocking of initial TIL cultures

| | Pool T | Pool R | Pool B | Pool A | Pool S | Pool 1 | Pool 2 | Pool 3 | Pool 4 | Pool 5 | Pool 6 | Frag. 12 |
|---|---|---|---|---|---|---|---|---|---|---|---|---|
| Tumor | 2179.50 | 752.12 | 2993.64 | 4427.63 | 2313.73 | 3409.99 | 7213.00 | 3722.50 | 3866.23 | 2914.58 | 3916.23 | 2.44 |
| Tumor + Class I Block | 94.32 | 11.95 | 67.49 | 38.78 | 67.88 | 75.74 | 394.68 | 258.88 | 86.28 | 369.32 | 513.78 | 2.44 |
| Media only | 2.44 | 52.71 | 67.56 | 2.44 | 2.44 | 40.87 | 16.52 | 131.40 | 2.44 | 2.44 | 21.22 | 2.44 |
| PMA/ Iono | 2010.14 | 360.33 | 2563.22 | 2929.14 | 1203.62 | 2038.37 | 1565.83 | 1454.78 | 2757.56 | 2012.09 | 2155.09 | 2.44 |
| % Blocking | 96% | 98% | 98% | 99% | 97% | 98% | 95% | 93% | 98% | 87% | 87% | 0% |

Figure 2A:
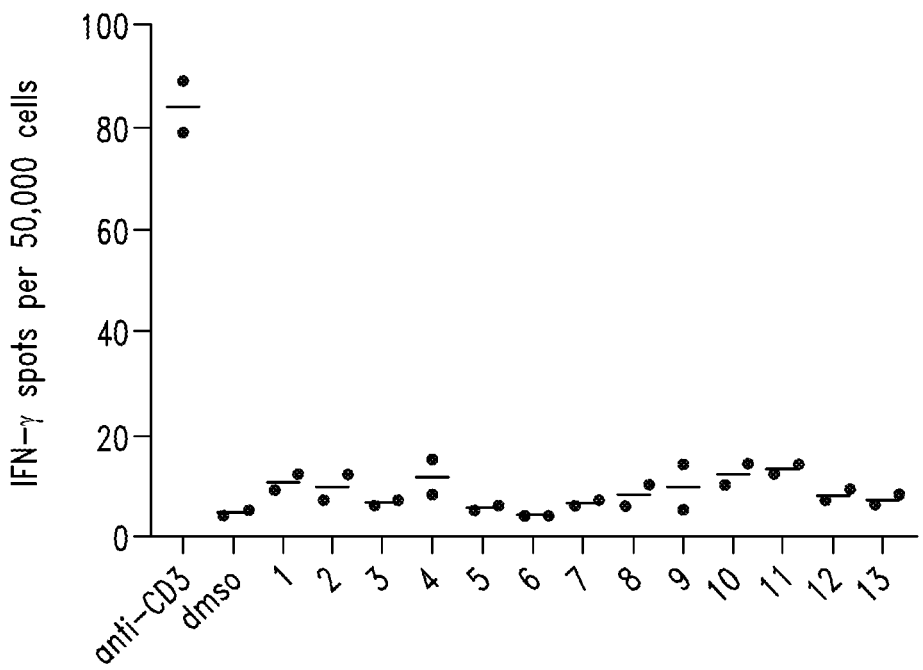
FIGS. 2A-2O show the specificity of CD8$^+$ T cells in TIL (tumor infiltrating lymphocytes) and TCR sequencing of T cell clonotypes in blood after adoptive transfer. (2A) IFN-γ production by TIL incubated with autologous CD40L-activated B cells pulsed with 13 pools of peptides encompassing 40 20-mer peptides containing the 20 nonsynonymous mutations present in the patient's melanoma by elispot assay. The final concentration of each peptide in the assay was 10 µg/ml. Three technical replicates were performed. (2B-2F) IFN-γ production by TILs incubated with B cells transduced with tandem minigenes encompassing 29 non-synonymous mutations or the coding sequences from self-antigens Tyrosinase, Mage A3, Mart1, SSX2, and GP100 in the presence of brefeldin A (2B-2E) or pulsed with tumor-associated self-antigens (2F). The final concentration of each peptide in the assay was 10 µg/ml. Three technical replicates were performed. (2G) Frequency of TCR Vβ sequences in peripheral blood mononuclear cells after mock stimulation, BRAF$^{V600E}$ peptide stimulation, or after sorting IFN-γ secreting cells following BRAF$^{V600E}$ peptide re-stimulation. (2H) TCR Vβ clonotypes of BRAF-specific T cells quantitated by TCRβ sequencing of pre-treatment blood, tumor single cell suspension, and the TIL product infused into the patient. (2I) TCRVβ sequences in TIL product ranked by prevalence (right-hand portion of graph). (2J) Frequency of the top 34 TIL TCR Vβ clonotypes from (2I) in pre-treatment blood and post-treatment blood obtained at 10 and 24 months. (2K) Frequency of TCR Vβ clonotypes of CD4$^+$ BRAF$^{V600E}$ and CD8$^+$ T cells specific for the specified antigens in pre-treatment and post-treatment blood. (2L-2O) TCR β sequencing on the TIL and T cells from TIL incubated with autologous B cells and tiled peptides. Tiled peptides spanned (2L) Tyrosinase, (2M) Mart1, (2N) Mage A3, and (2O) TRP2 and sorted by IFN-γ capture. Antigen-specific TCR β sequences enriched in the sorted cells are marked with a box.
Figure 2B:
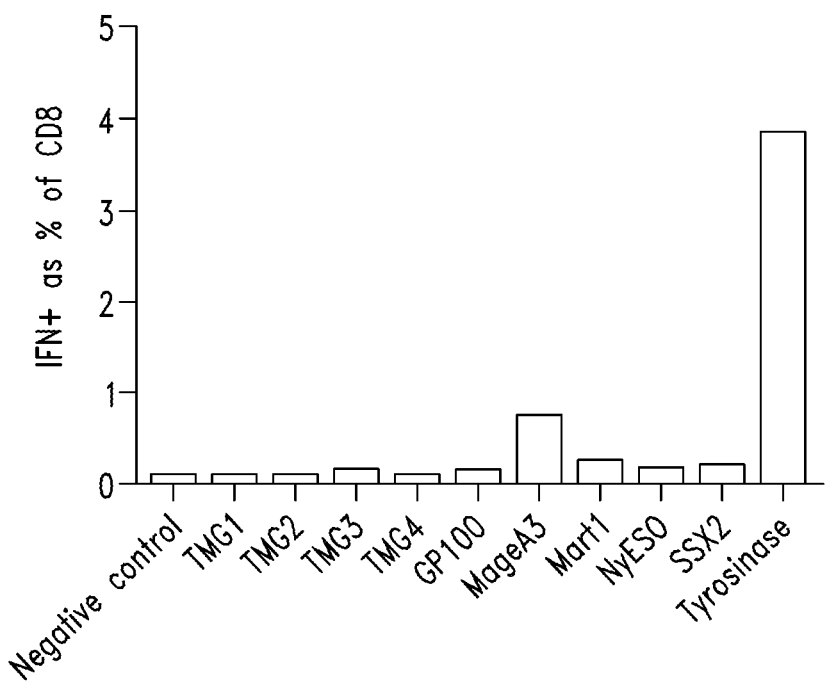
Figure 2C:
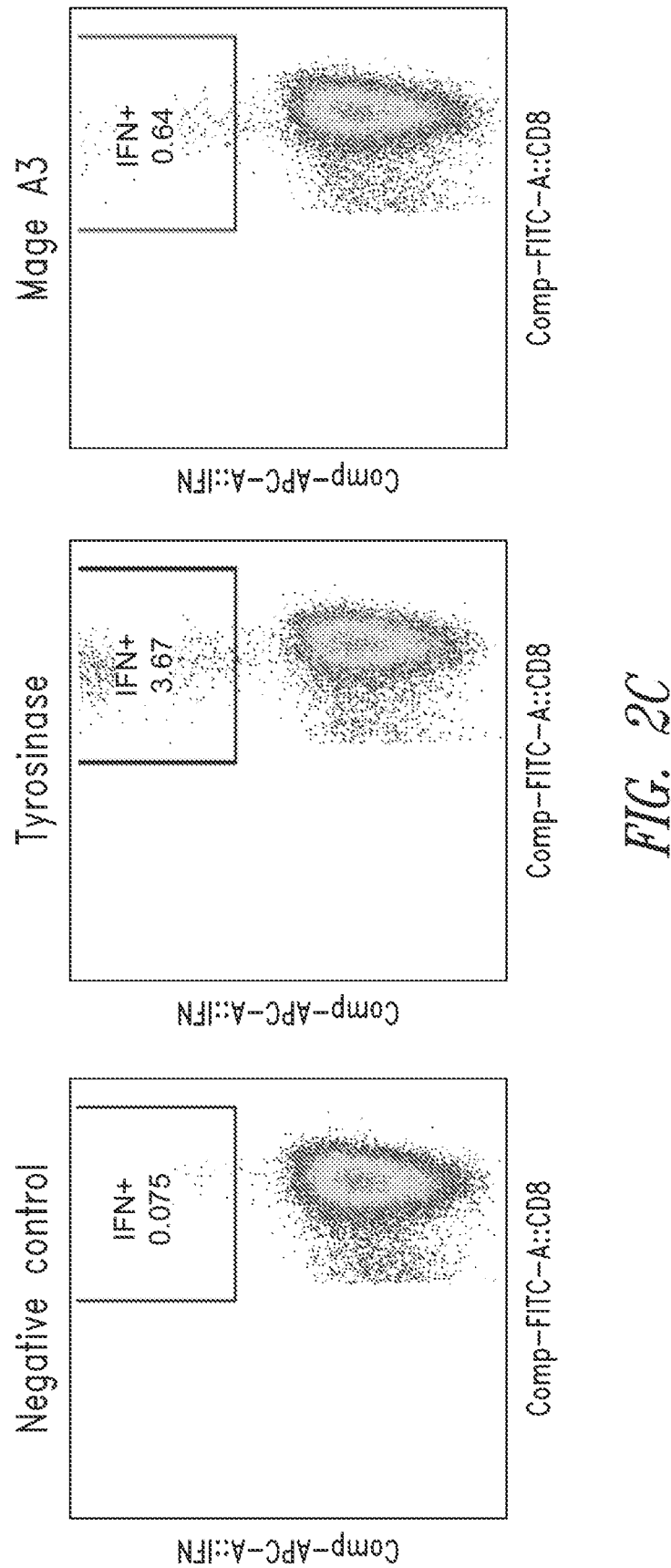
Figure 2D:
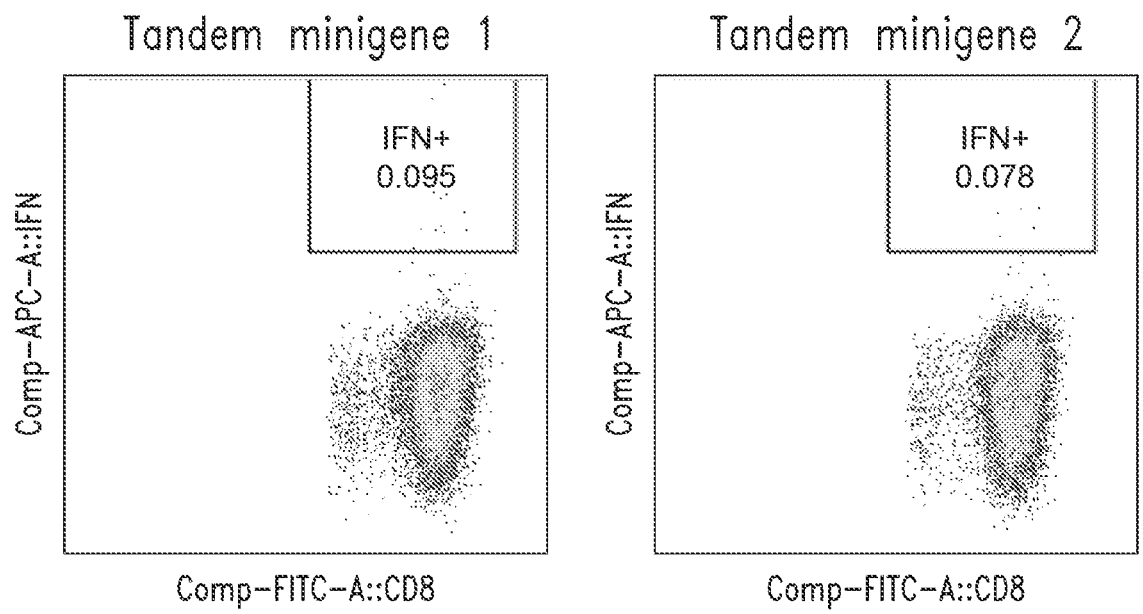
Figure 2E:
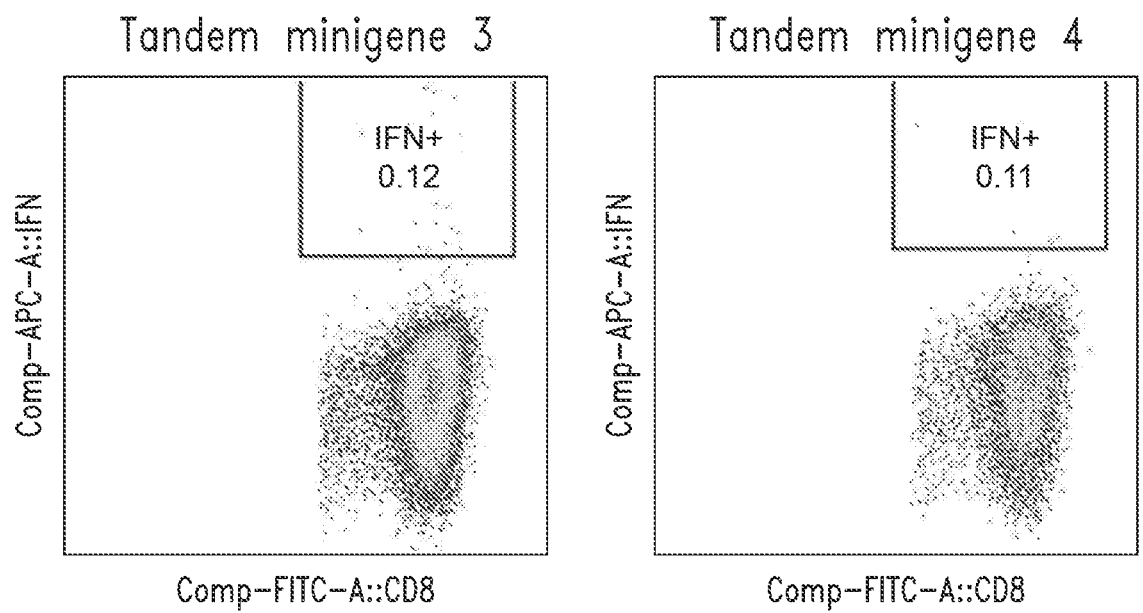
Figure 2F:
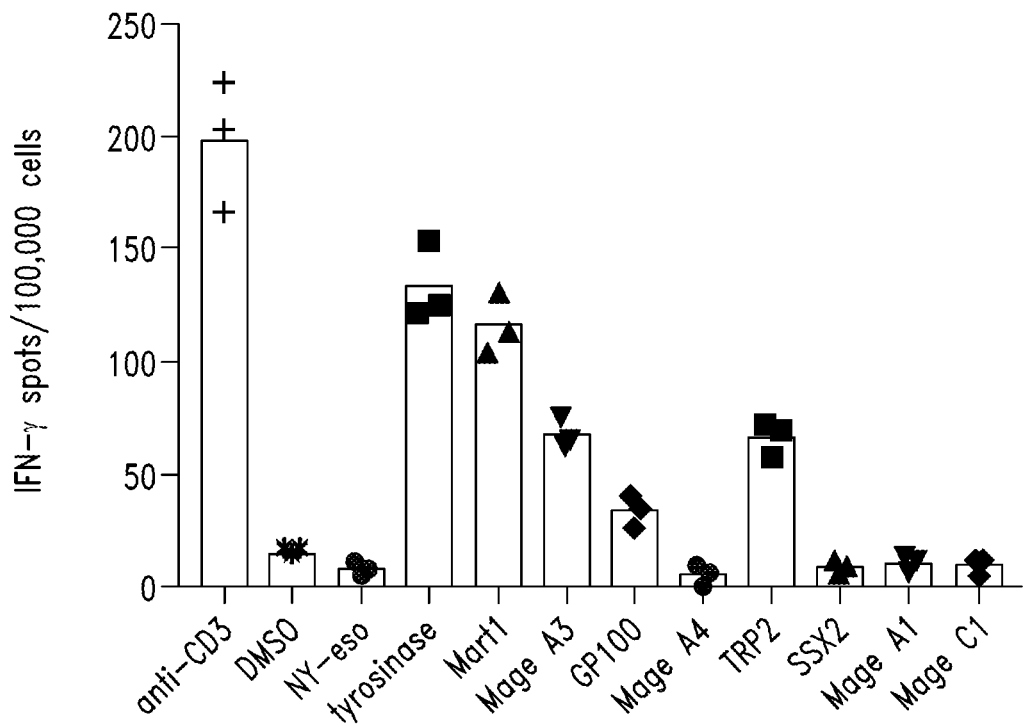

No IFN-γ production was observed when TIL were cultured with autologous B cells pulsed with pools of peptides that included all of the 20 non-synonymous mutations identified by tumor exome sequencing (FIG. 2A), but IFN-γ was produced after co-culture with B cells pulsed with peptides from lineage-restricted self-antigens (tyrosinase, Mart-1, TRP2) and a cancer testes antigen (Mage A3), which are known targets of T cells in melanoma (see, e.g., Gros et al. Nat. Med. 2016) (FIG. 2F), or transfected with tandem minigenes encompassing 29 non-synonymous mutations or the coding sequences of Tyrosinase, Mage-A3, Mart1, SSX2, and GP100 (FIGS. 2B-2E). Thus the patient TIL contained $BRAF^{V600E}$-specific $CD4^+$ T cells and a diverse $CD8^+$ T cell response to self-antigens.

Clinical Protocol

The patient was enrolled for TIL generation under an FDA-approved IND and a clinical protocol approved by the Institutional Review Board of Fred Hutchinson Cancer Research Center (FHCRC 2643; NCT01807182). Patients with stage IV melanoma, or stage III unlikely to be cured by surgery, >18 years of age, with an ECOG </=1, with a site of metastatic disease that could be safely resected or biopsied, were eligible. TIL were expanded from tumor fragments in 6,000 IU/ml recombinant IL-2 (Proleukin; Novartis), using methodologies developed at the Surgery Branch of the National Cancer Institute (e.g., Dudley et al., J. Immunother. 24(4):363-373 (2002)). TIL cultures were selected based on cell growth and autologous tumor reactivity as determined by IFN-γ secretion following co-culture with autologous tumor cells. The TIL were cryopreserved until needed for use, then thawed and further expanded using a rapid expansion protocol, as previously-described (Riddell and Greenberg, J. Immunological Methods 128(2):189-201 (1990)). The expanded TIL were administered to the patient following a lymphodepleting chemotherapy regimen of cyclophosphamide 60 mg/kg/day×2 days, then fludarabine 25 mg/m²/day×5 days. Within 24 hours of the TIL infusion, the patient received high-dose IL-2 at 600,000 IU/kg IV every 8 hours, for a total of 9 doses. Tumor responses were assessed using RECIST version 1.1 with CT and MRI at weeks 6, 12, and 24, then every 3-6 months, at the discretion of the primary provider.

Nucleic Acid Preparation for Exome Capture and RNA sequencing

Post-treatment blood was used to isolate non-tumor DNA. A single-cell suspension derived from the iliac nodal tumor recurrence was flow sorted (propidium iodide negative and CD45 negative) to deplete abundant infiltrating lymphocytes and enrich for neoplastic cells. Normal tissue and sorted tumor cells were processed with the Qiagen DNA/RNA AllPrep Micro kit to isolate DNA for exome capture, with RNA reserved for subsequent RNA-seq profiling. Genomic DNA concentration was quantified on an Invitrogen Qubit® 2.0 Fluorometer (Life Technologies-Invitrogen, Carlsbad, CA, USA) and Trinean DropSense96 spectrophotometer (Caliper Life Sciences, Hopkinton, MA).

Whole Exome Sequencing

Exome sequencing libraries were prepared using the Agilent SureSelectXT Reagent Kit and exon targets isolated using the Agilent All Human Exon v6 (Agilent Technologies, Santa Clara, CA, USA). 200 ng of genomic DNA was fragmented using a Covaris LE220 focused-ultrasonicator (Covaris, Inc., Woburn, MA, USA) and libraries prepared and captured on a Sciclone NGSx Workstation (PerkinElmer, Waltham, MA, USA). Library size distributions were validated using an Agilent 2200 TapeStation. Additional library QC, blending of pooled indexed libraries, and cluster optimization was performed using Life Technologies' Invitrogen Qubit® 2.0 Fluorometer.

The resulting libraries were sequenced on an Illumina HiSeq 2500 using a paired-end 100 bp (PE100) strategy. Image analysis and base calling was performed using Illumina's Real Time Analysis v1.18 software, followed by "demultiplexing" of indexed reads and generation of FASTQ files using Illumina's bcl2fastq Conversion Software v1.8.4 (http://support.illumina.com/downloads/ bcl2fastq_conversion_software_184.html). Read pairs passing standard Illumina quality filters were retained for further analysis, yielding 77M read pairs for the tumor and 89M read pairs for the normal. Paired reads were aligned to the human genome reference (GRCh37/hg19) with the BWA-MEM short-read aligner (see, e.g., Li, H., *arXiv preprint arXiv:*1303.3997 (2013); Li and Rudbin, *Bioinformatics* 25(14):1754-1760). The resulting alignment files, in standard BAM format, were processed by Picard 2.0.1 and GATK 3.5[37] for quality score recalibration, indel realignment, and duplicate removal according to recommended best practices (see, Auwera et al., *Current Protocols in Bioinformatics* pp. 11.10.1-11.10.33 (2013)).

Three independent software packages were used to call somatic mutations from the analysis-ready tumor and normal BAM files: MuTect 1.1.7[39], Strelka 1.0.14[40], and VarScan.v2.4.1 (Koboldt et al., *Genome Res.* 22(3):568-576 (2012)). Variant calls from all tools, in VCF format, were annotated with Oncotator (Ramos et al., *Human Mutation* 36(4):E2423-E2429 (2015)). Missense somatic variants were combined and annotated further, including wild-type and variant peptide sequences, to form an integrated summary from which candidate peptides were chosen for synthesis.

RNA-Seq Data Processing

To rank candidate peptides by observed expression level, RNA-seq was performed on flow-sorted tumor cells from the same single cell suspension. RNA-seq libraries were prepared from total RNA using the TruSeq RNA Sample Prep v2 Kit (Illumina, Inc., San Diego, CA, USA) and a Sciclone NGSx Workstation (PerkinElmer, Waltham, MA, USA). Library size distributions were validated using an Agilent 2200 TapeStation (Agilent Technologies, Santa Clara, CA, USA). Additional library QC, blending of pooled indexed libraries, and cluster optimization was performed using Life Technologies' Invitrogen Qubit® 2.0 Fluorometer (Life Technologies-Invitrogen, Carlsbad, CA, USA). The library was sequenced on an Illumina HiSeq 2500 to generate 133M 50 nt paired reads (PE50). Reads were aligned to a RefSeq derived reference transcriptome with RSEM 1.2.19 (see Li and Dewer, *BMC Bioinformatics* 12(1):323 (2011)). Gene-level expression values from RSEM, in TPM units, were added to the summary of missense somatic variants.

T Cell Culture

Initial stimulations were performed with overlapping 20-mer crude peptides obtained from Elim Biopharma, with 2 peptides spanning each mutation with the mutated residue at position +7 or +13 of the 20 amino acid sequence. Subsequent experiments were performed with >80% purity 21 mer peptides with V600 (wildtype) or E600 (mutant) at position +11. Cryopreserved PBMC were thawed and rested overnight in CTL (RPMI media with L-glutamine and HEPES (Gibco) supplemented with 10% human serum (produced in house), 50 µM beta-mercaptoethanol, penicillin and streptomycin, 4 mM L-glutamine and 2 ng/ml recombinant human IL-7 (Peprotech). The following morning, PBMC were washed and stimulated at 10e6 cells in 5 ml CTL per well of a 6 well plate with a pool of 1 µg/ml of each peptide without cytokines. Recombinant IL-2 (Peprotech) was added to a final concentration of 10 U/ml on day +3, and half media changes with supplemental IL-2 were performed on days +3, +6, and +9. On day +13, cells were used in an ELISA and cytokine staining assays.

Antigen-specific T cell enrichment was carried out by staining live cells for secreted IFN-γ using the IFN-γ secretion assay APC (Milltenyi) following the manufacturer's instructions, and using autologous B cells as antigen presenting cells pulsed with 10 µg/ml 21-mer BRAF mutant peptide. CD4+ IFN-γ secreting cells were sorted on a FACS Aria2. Sorted cells were rested in CTL supplemented with 10 ng/ml human IL-15 for 5 days, then expanded using a rapid expansion protocol described previously (Riddell and Greenberg, supra). Antigen-specific T cells were further enriched by sorting for Vβ3.1 positive, CD4+ cells by staining with anti-Vβ 3.1 (Thermo Scientific, cat. no. TCR2740), expanded, and cryopreserved at day 13 or 14 after expansion. Cryopreserved cells were thawed and rested overnight in CTL supplemented with 10 U/ml IL-2 prior to assays.

Antigen-Presenting Cells

Autologous B cells were isolated from fresh or thawed PBMC using magnetic beads coated with antibodies recognizing CD19 (Miltenyi, cat. no. 130-050-301) and magnetic positive selection according to the manufacturer's instructions (Miltenyi, cat. no. 130-042-401). Primary B cells were incubated in a 1:1 ratio with NIH 3T3 cells expressing humanCD40L for 7 days in B cell medium supplemented with 200 U/ml human IL-4 (Peprotech) as described (see Tran et al., *Science* 344(3184):641-645 (2014)). B cells were subsequently harvested and restimulated with 3T3 CD40L and fresh medium every 3 days. B cells were used in assays at day +3 of stimulation 2 or 3.

Cytokine Release Assays

In ELISA assays, 50,000 effector T cells were incubated in 96 well round bottom plates with 100,000 B cells or B-LCL lines and 10 µg/ml or specific concentrations of peptides in RPMI (Gibco) supplemented with 5% heat inactivated fetal bovine serum. IFN-γ in supernatants was quantitated using the ready set go human IFN-γ ELISA kit (ebiosciences) in technical triplicate. HLA blocking experiments were carried out with 20 µg/ml antibody anti class I (Biolegend, cat. no. 311411) anti-HLA DR (clone L243, cat. no. 307611) and HLA-DQ (Abcam, clone spv-13, cat. no. ab23632) added 1 hour prior to adding peptide. For elispot assays, 50,000 tumor infiltrating lymphocytes were incubated with 200,000 autologous B cells pulsed with peptide pools at a final concentration of 10 µg/ml of each peptide in CTL medium using the human IFN-γ ELISpot-Pro kit (Mabtech) and developed using the manufacturer's instructions.

HLA Identification

LCL cell lines 1331, DUCAF, VAVY, BM14, DEM and DEU were utilized. For co-culture assays, LCL cell lines were pulsed with 10 µg/ml of BRAF mutant peptide or DMSO control for 4 hours and then washed 3 times with PBS prior to ELISA assay. For identification of specific class II alleles, codon optimized linear DNA fragments encoding HLA-DRB1 0404 protein or the HLA-DQB1 0302 protein linked by a T2A skip sequence to HLA-DQA1 0301 protein were synthesized using Genestrings™ (Life Sciences) and cloned into the vector MP71 (Engels et al., *Hum. Gene Ther.* 14(12):1155-1168 (2003)) linearized with NotI and EcoRI (Thermo Fisher) using the NEBuilder cloning kit (New England Biolabs) and sequence verified. Retroviral transduction was performed as described by Sommermeyer et al., (*Leukemia*, 2015)) into the VAVY cell line homozygous for HLA DRB1 0301, DQA1 0501, and DQB1 0201 (Research cell bank). Cells positive for DRB1 0404 were sorted on a FACSAria2 sorter using the antibody DRB1-PE (Biolegend, cat. no. 362303) and cells positive for DQB1 03 DQA1 03 were sorted using the anti DQ antibody clone HLADQ1-FITC (Biolegend, cat. no. 318104). Assays were performed with and without pulsing with BRAF$^{V600E}$ peptide. ELISA experiments were performed in technical duplicate or triplicate as indicated and are representative of two independent experiments.

Example 2

Identification of TCR Gene Usage by TIL

Figure 2G:
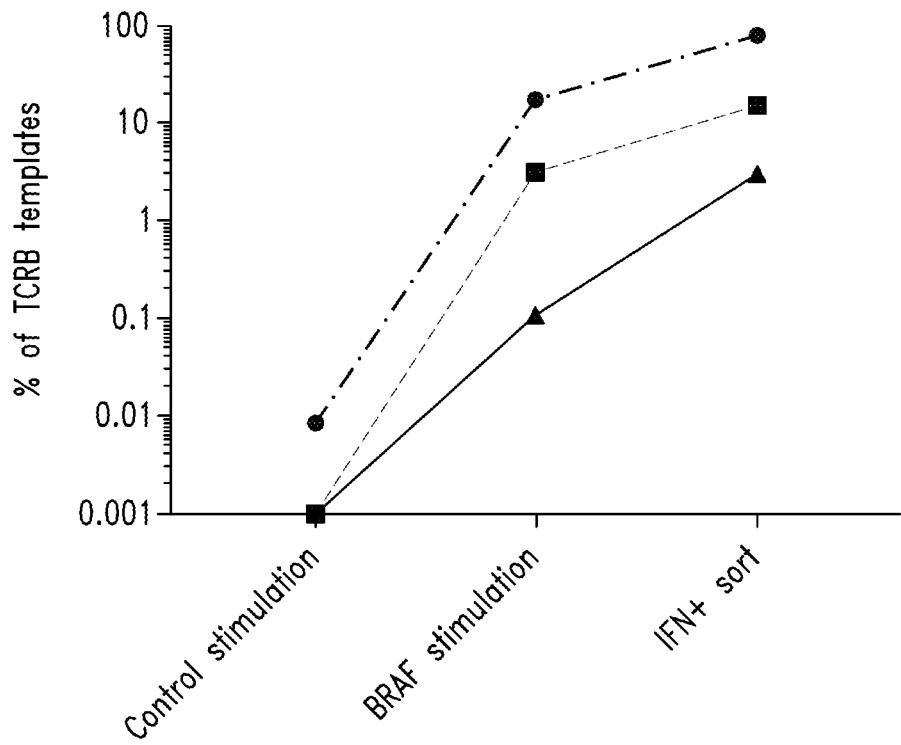
Figure 2H:
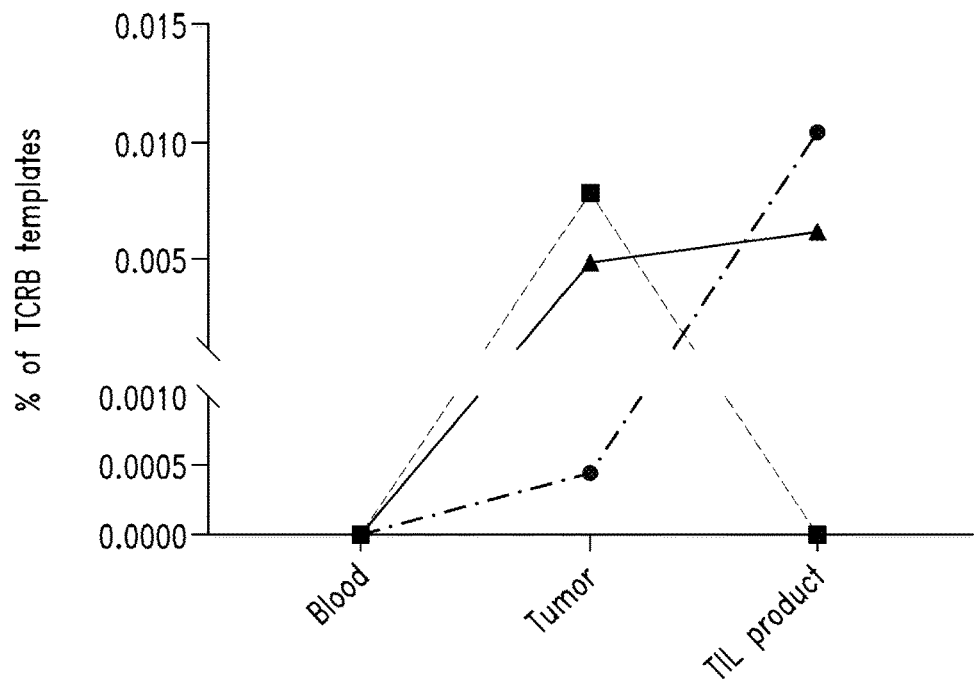
Figure 2I:
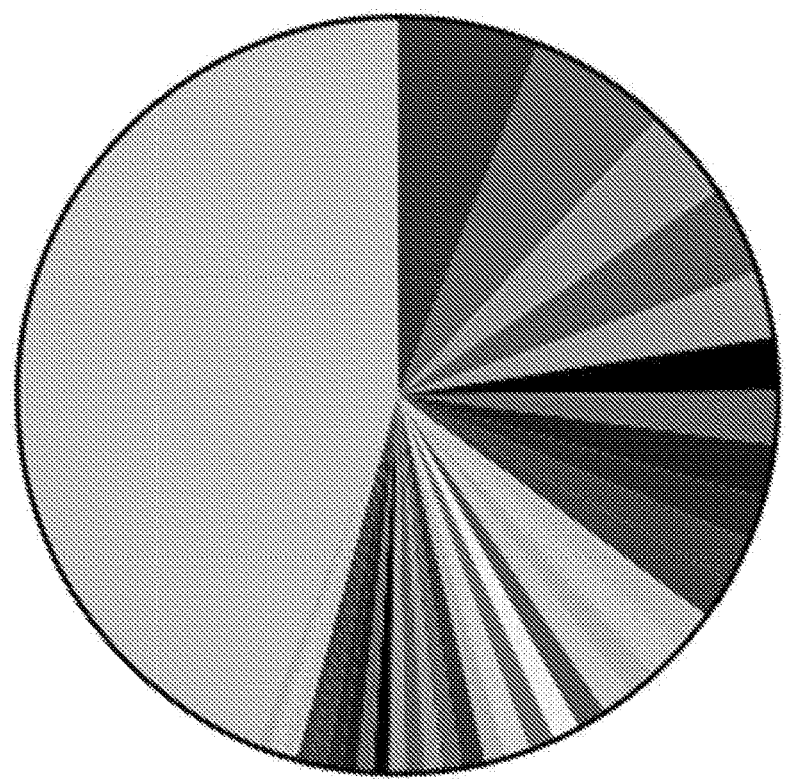
Figure 2J:
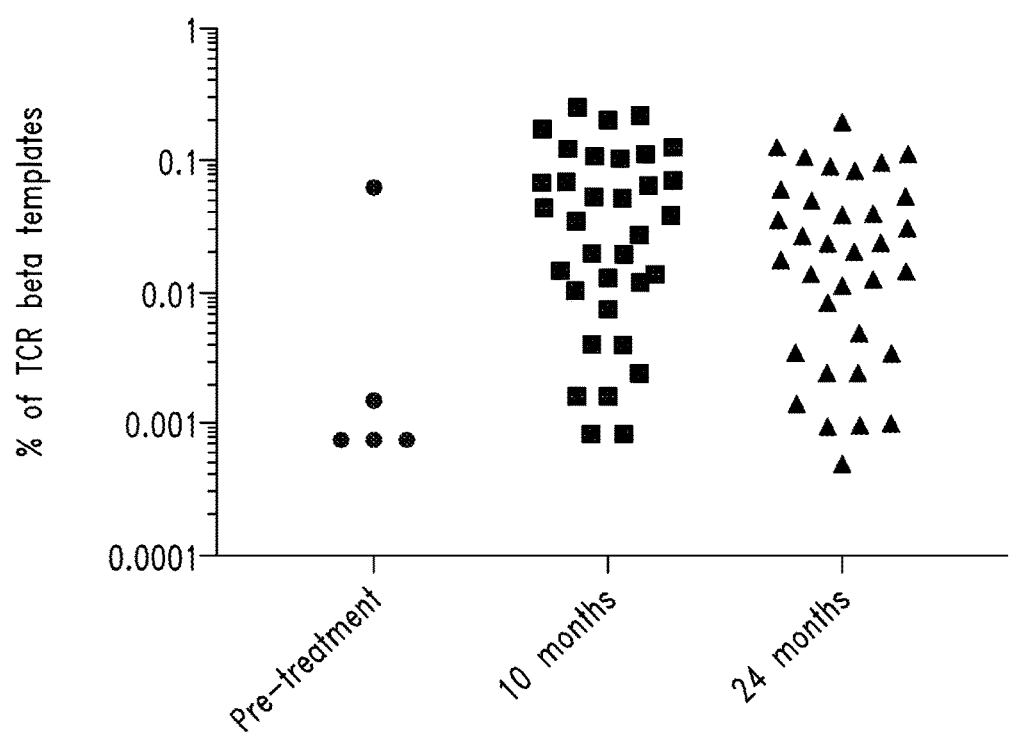
Figure 2K:
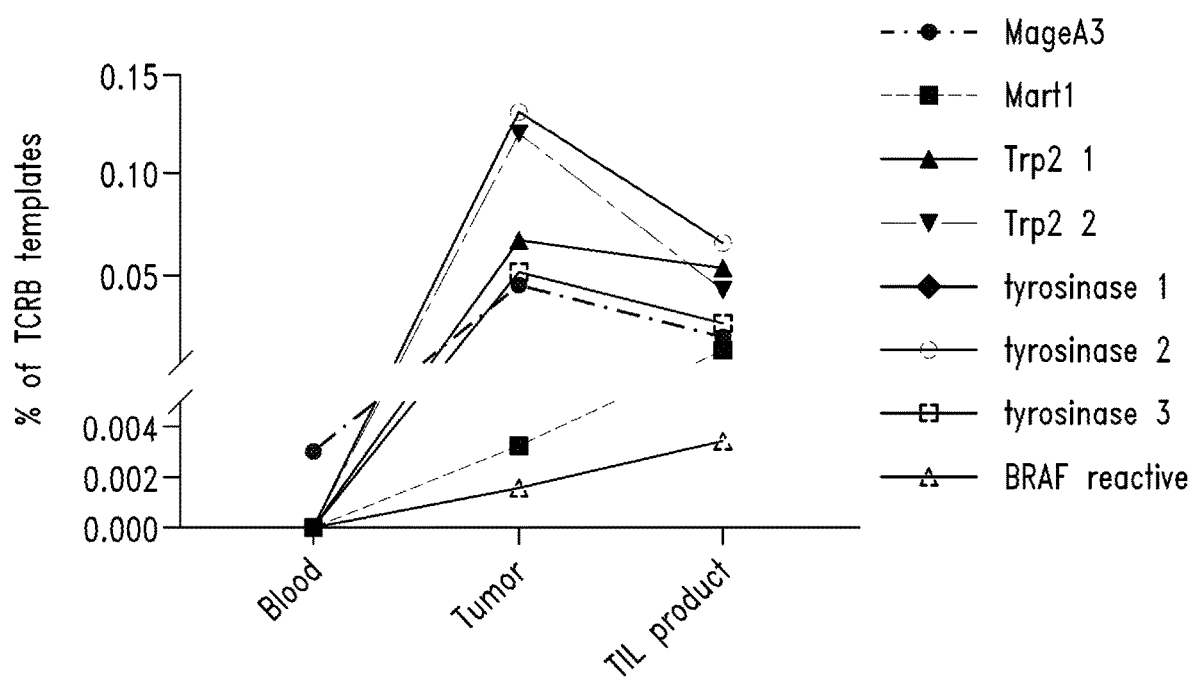
Figure 2L:
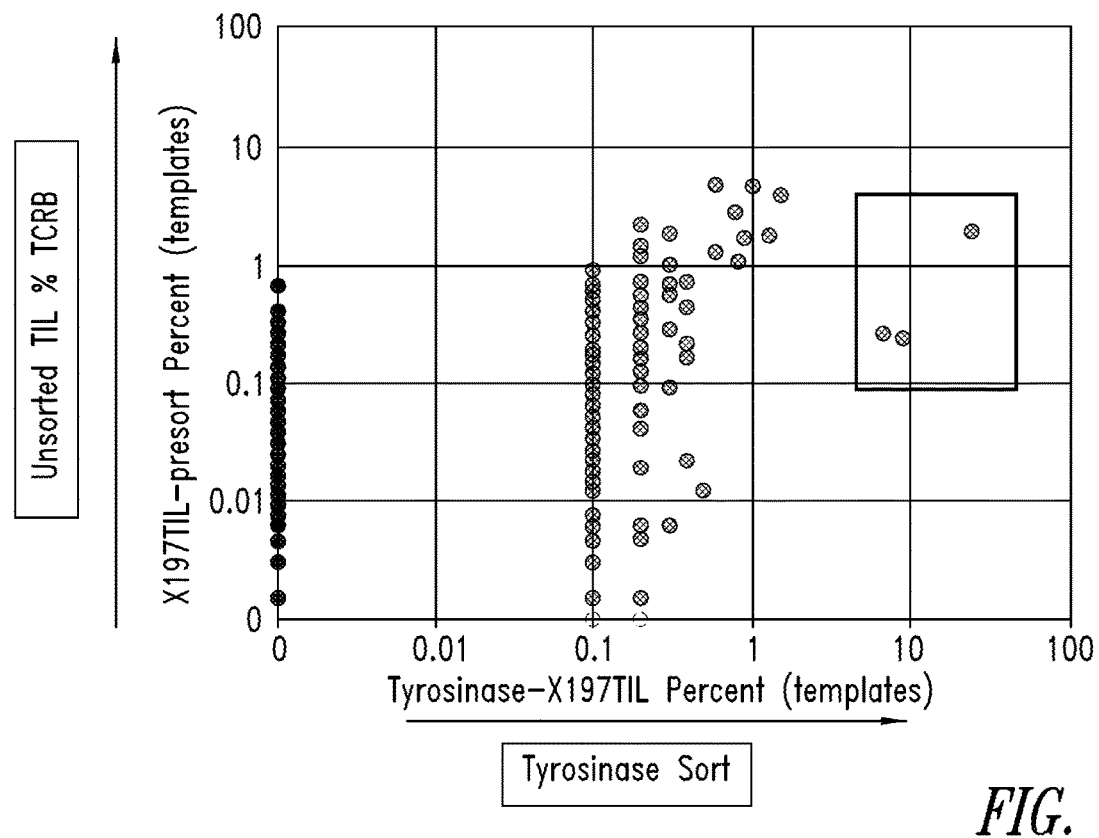
Figure 2M:
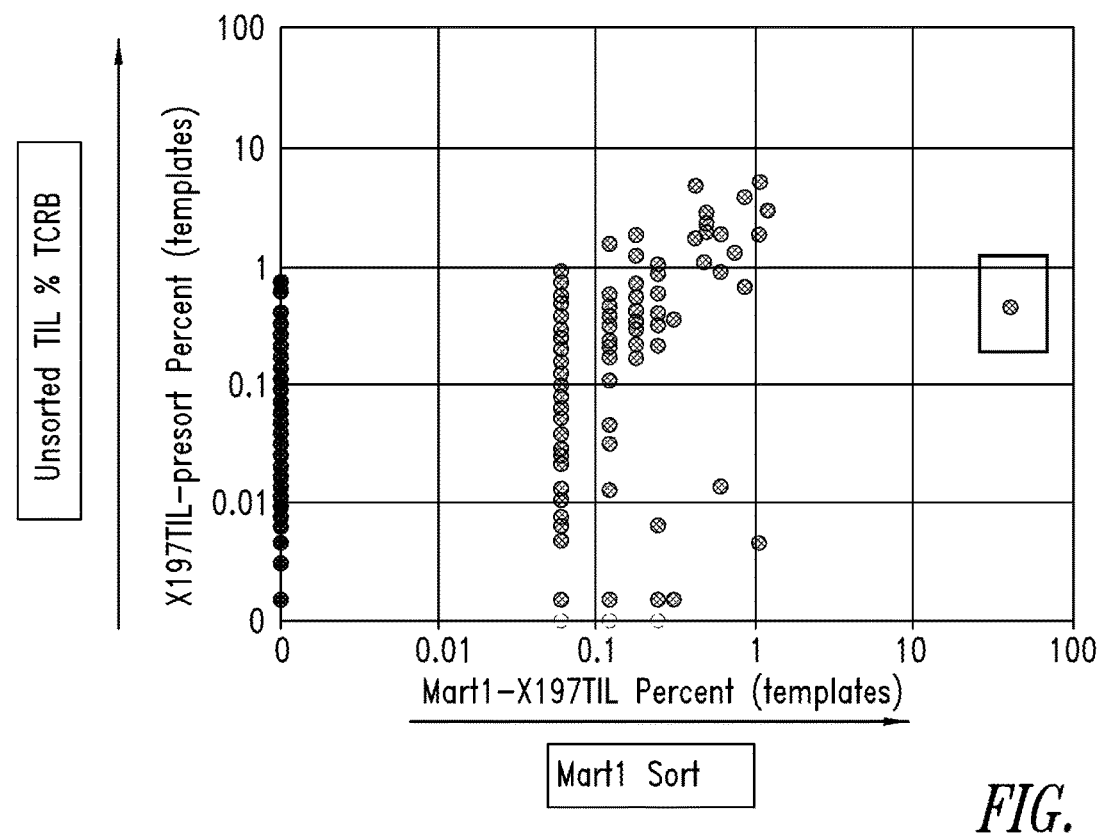
Figure 2N:
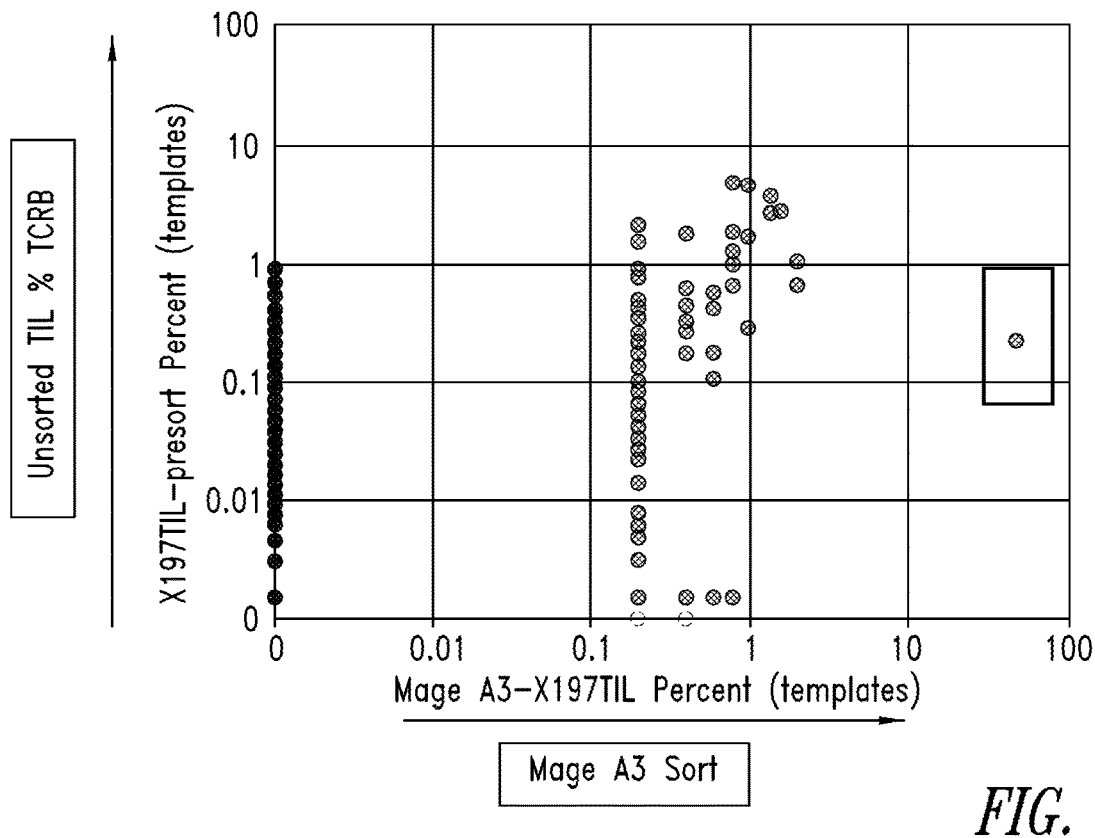
Figure 2O:
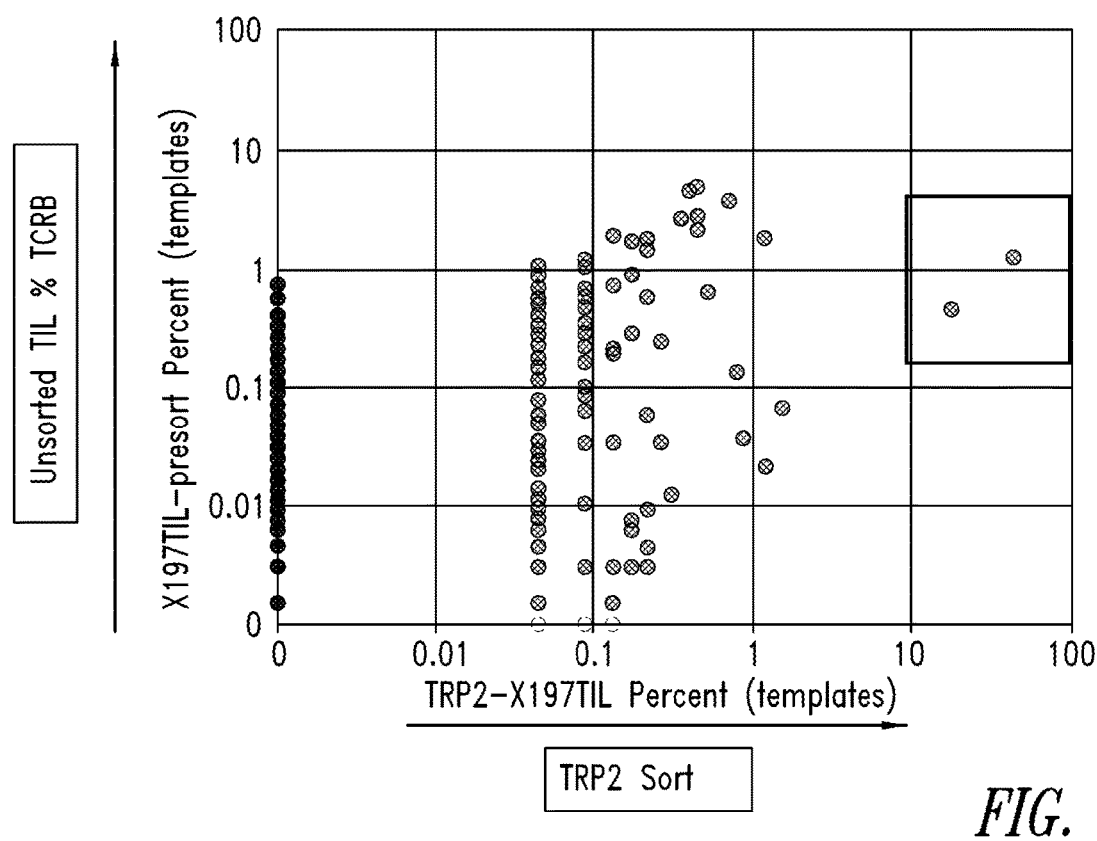

Deep sequencing was performed to identify TCR gene usage in BRAF$^{V600E}$-specific T cells and other T cells in the TIL. Three TCR clonotypes showed marked expansion after stimulation of post-treatment PBMC with BRAF$^{V600E}$ peptide, and these sequences were further enriched after IFN-γ capture, indicating their specificity for the mutant peptide (FIG. 2G). TCR Vβ sequencing of tumor, TIL, and PBMC obtained prior to TIL infusion identified all 3 TCR Vβ clones in the tumor, and 2 of 3 in TIL. All 3 TCR Vb sequences were below the level of detection in pre-treatment PBMC indicating enrichment at the tumor site (FIG. 2H). A total of 34 common Vβ sequences collectively made up >50% of the TIL product (FIG. 2I). Only 5 of these 34 clones were detected in the pretreatment blood, with 4 at very low frequency (FIG. 2J). To assess TCR gene usage of CD8+ T cells recognizing each of the 4 lineage-specific or C/T antigens, IFN-γ capture was used to sort these cells from TIL and assess TCR Vβ usage. Seven different Vβ sequences in the sorted cells were identified and represented 4.7% of the T cells in the TIL product (FIGS. 2L-2O). These 7 clonotypes and one of the BRAF-specific clones were detected in blood obtained 10 and 24 months post-treatment (FIGS. 2J and 2K). RNA expression targeted to the endosome was carried out using the method described by Kreiter et al. (*J. Immunol.* 180(1):309-318 (2008)) where antigens are targeted to the endosome by fusion of the antigen to class I MHC sorting signals. The mRNA expression construct pJV57 was constructed by gene synthesis (Geneart, Life Sciences), which contained a T7 promoter fused to the N terminal 25 amino acids of the human HLA-B gene, followed by a BamHI restriction site, the coding sequence of enhanced GFP, an AgeI restriction site, the C terminal 55 amino acids of the human HLA-B gene, followed by the human beta globin untranslated region followed by a 30 nucleotide poly A tail followed by a SapI restriction site directing cleavage in the poly A tail. Construct pJV84 was cloned by ligating the following into AgeI/BamHI digested pJV57: annealed oligonucleotides (Ultramers, Integrated DNA Technologies) encoding BRAF amino acids 575-624 flanked by a 5' AgeI and 3' BamHI site containing the E600 substitution. Construct pJV85 was made by ligating annealed oligonucleotides (Ultramers, Integrated DNA Technologies) encoding BRAF amino acids 575-624 flanked by a 5' AgeI and 3' BamHI site containing the wildtype V600 amino acid. pJV84 and pJV85 were then linearized with SapI (Thermo Fisher) and mRNA was in vitro transcribed using the Highscribe T7 ARCA mRNA kit (New England Biolabs) and purified by lithium precipitation according to the manufacturer's instructions. mRNA was electroporated into CD40L stimulated B cells 16 hours prior to co-culture experiments as described by Tran et al. (supra).

Example 3

Phenotypic Characterization of TIL Product

Figure 3A:
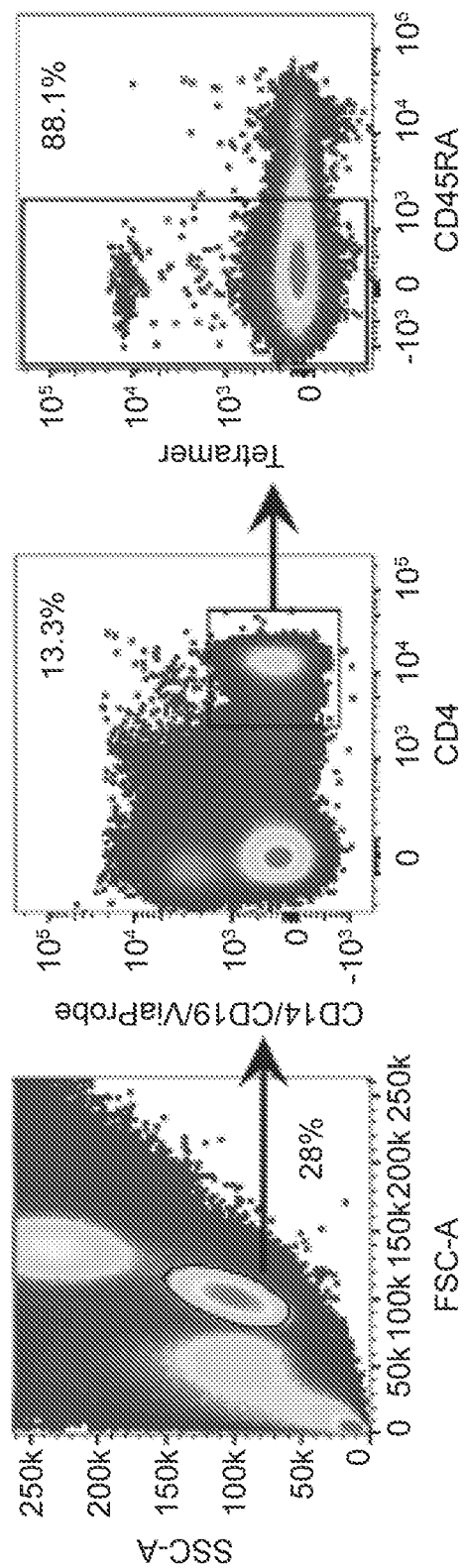
FIGS. 3A-3C show phenotypic analysis for BRAF-specific T cells following treatment with tumor-infiltrating lymphocytes (TILs). (3A) Dump channel gating scheme for excluding monocytes (CD14$^+$), B cells (CD19$^+$), and dead cells (ViaProbe) from TIL. Viable CD4+ T cells were plotted against tetramer and CD45RA. (3B) CD45RA− memory cells (88.1% of CD4+) that were tetramer-positive and -negative were plotted against the indicated cell surface markers. Numbers indicate the percentage of cells in the gated regions or the percentage of tetramer-positive cells for each marker. (3C) Intracellular cytokine staining of activated (CD154+) BRAF-specific T cells.
Figure 3B:
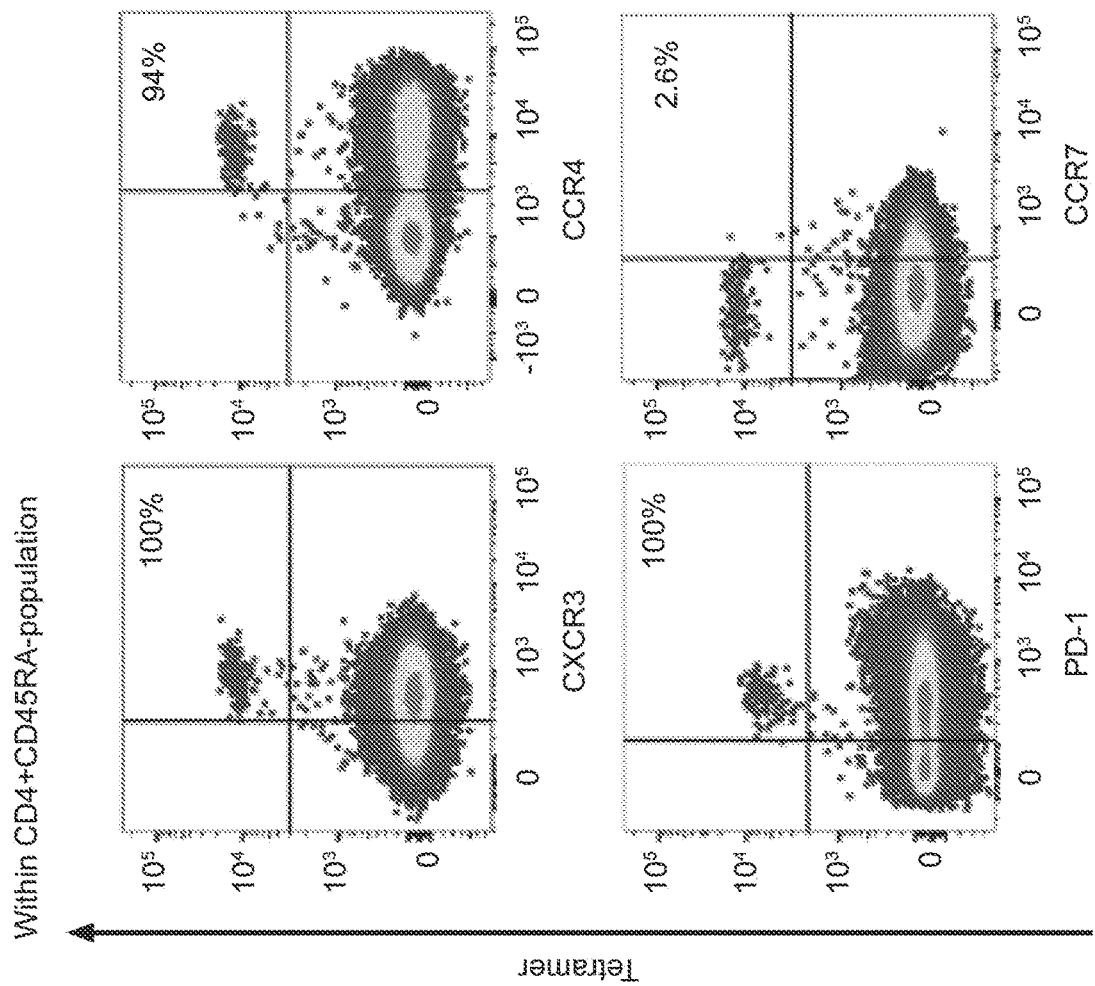
Figure 3B:
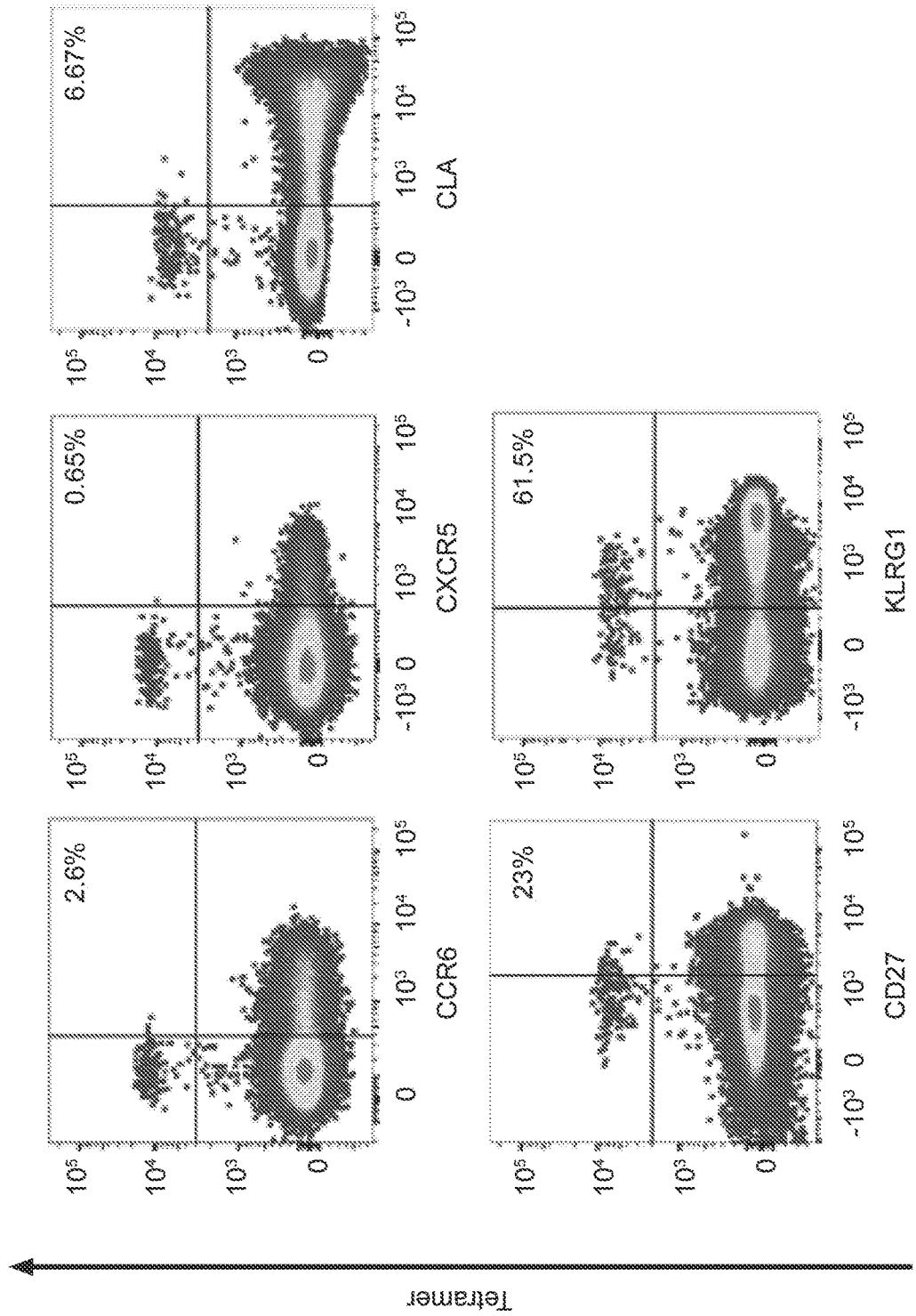
Figure 3C:
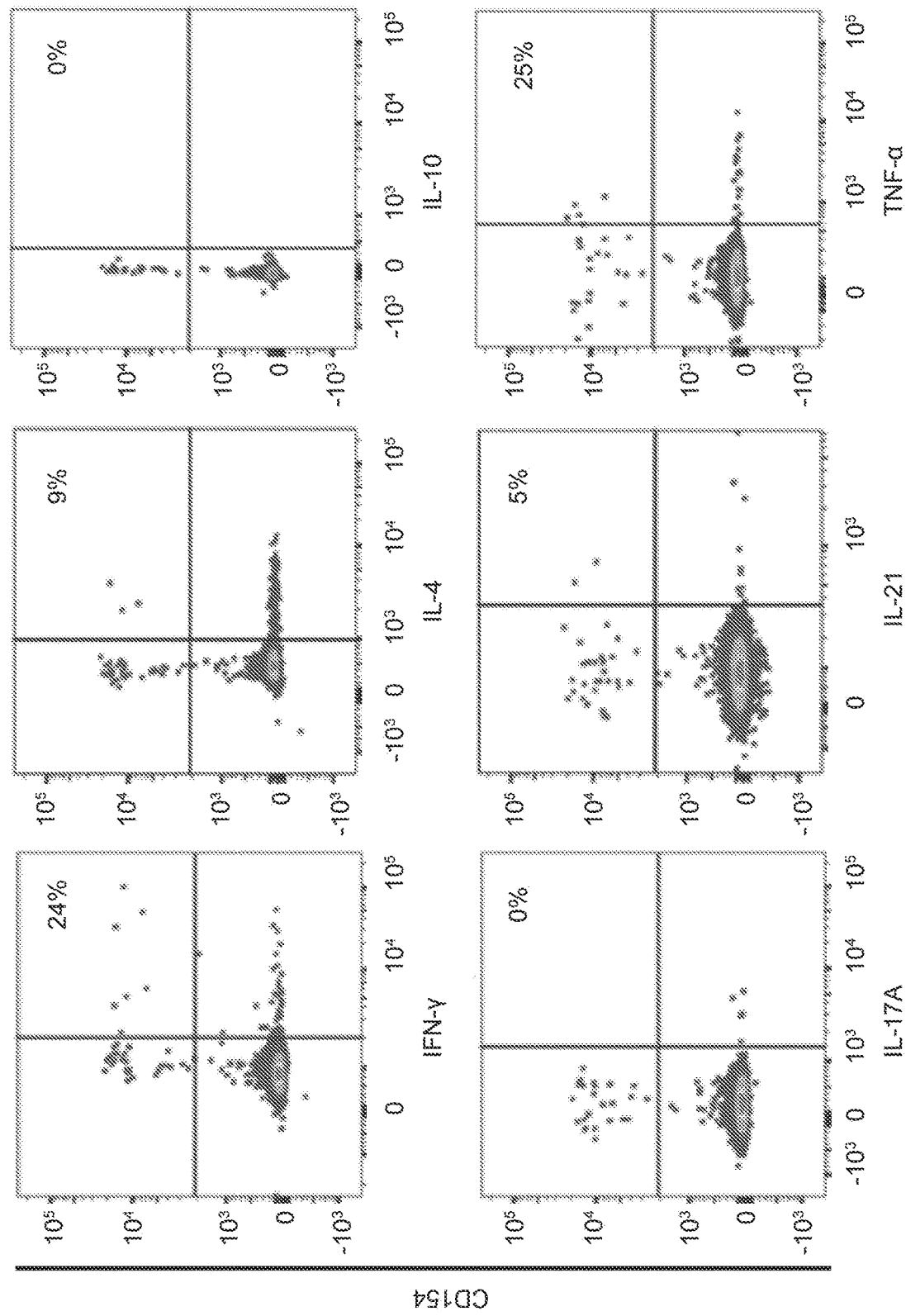

Phenotypic analysis of BRAF-specific clones was performed following TIL treatment (FIGS. 3A-3C). BRAF$^{V600E}$-specific CD4+ T cells showed an effector memory phenotype (CD45RA$^-$CCR7$^-$CD27$^-$KLRG1$^+$) and expressed low levels of PD-1 (FIGS. 3A, 3B). The majority of BRAF$^{V600E}$-specific cells expressed CXCR3 and CCR4. A fraction of the cells also expressed the skin-homing marker cutaneous lymphocyte-associated antigen (CLA). BRAF$^{V600E}$ peptide-activated cells produced IFN-γ, TNF-α, IL-4, and IL-21 (FIG. 3C), sometimes in combination (data not shown). Taken together, these data suggest that circulating BRAF-specific CD4+ T cells after TIL infusion have a mixed Th1/Th2 phenotype, consistent with an established memory cellular immune response to mutated BRAF in melanoma.

Example 4

Construction and Testing of BRAF$^{V600E}$ TCRs

Durable remissions in melanoma after adoptive transfer of self-antigen reactive CD8+ T cells alone are exceedingly rare (see, e.g., Johnson et al., *Blood* 114(3):535-546 (2009); Yee et al., *PNAS* 99(25):16168-16173 (2002); Dudley et al., *J. Immunother.* 24(4):363-373 (2001)). Without wishing to be bound by theory, it is believed that the BRAF$^{V600E}$-specific CD4+ T cells provide direct antitumor effects and aid the persistence and function of self-antigen reactive CD8+ T cells against a tumor that contained few neoantigens. The HLA-DQA1*03/DQB1*03 restricting allele for the BRAF$^{V600E}$-specific CD4+ T cells is present in 29% of individuals in the International Histocompatibility Workgroup database (Petersdorf, E., *personal communication, International Histocompatibility Working Group in Hematopoietic Cell Transplantation.* 2017), and isolation of the BRAF$^{V600E}$-specific TCR genes from this patient can facilitate adoptive therapy for patients with BRAF mutant tumors with TCR engineered T cells. TCR Vα sequencing on samples with varying levels of BRAF-reactive clones identified four (4) TCR Vα sequences that correlated in frequency with the three (3) TCR Vβ sequences (FIG. 2G).

Figure 4A:
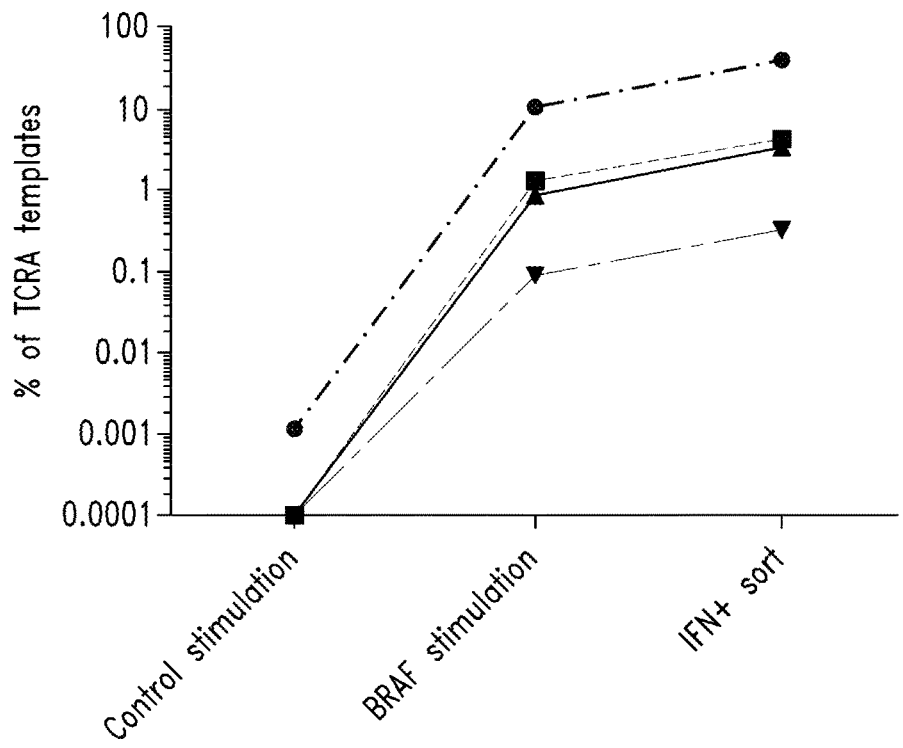
FIGS. 4A-4B show that a synthetic TCR derived from the dominant Vα and Vβ sequences of melanoma-responsive patient TILs recognizes cells expressing $BRAF^{V600E}$. (4A) Frequency of TCRBVα sequences in peripheral blood mononuclear cells after mock stimulation, $BRAF^{V600E}$ stimulation, or after sorting IFN-γ secretion cells following $BRAF^{V600E}$ peptide re-stimulation. (4B) IFN-γ production by CD4+ T cells from two normal donors transduced with a synthetic TCR construct and incubated with an HLA-DQB1*0302 B cell line 1331 pulsed with $BRAF^{V600E}$ peptide or transfected with mRNA encoding mutant or wildtype BRAF sequences. N=2 or 3 technical replicates as indicated.
Figure 4B:
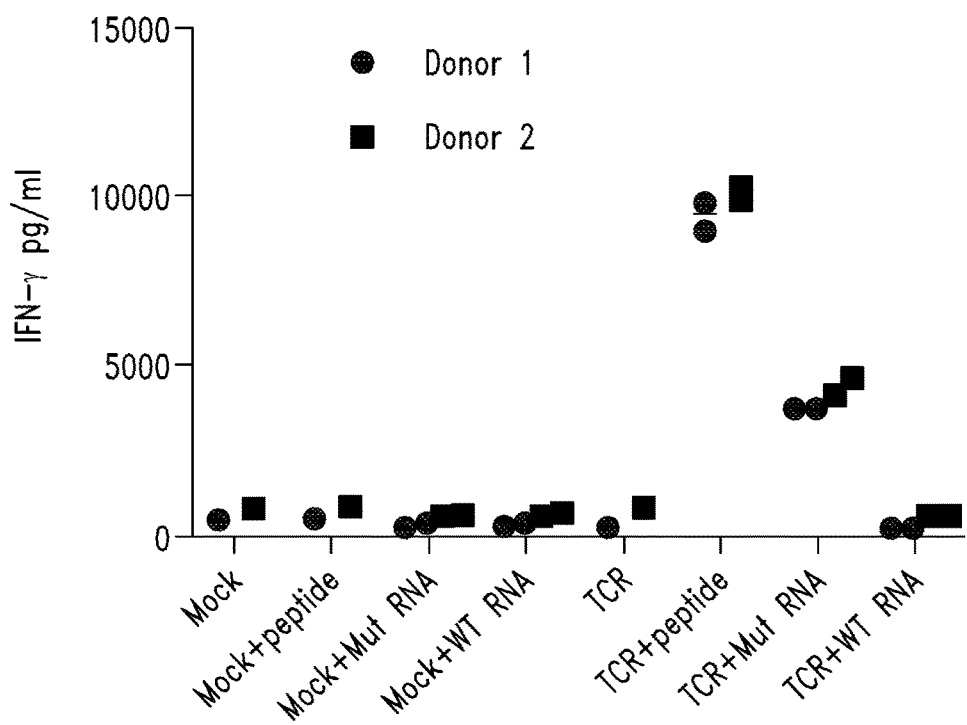
Figure 5:
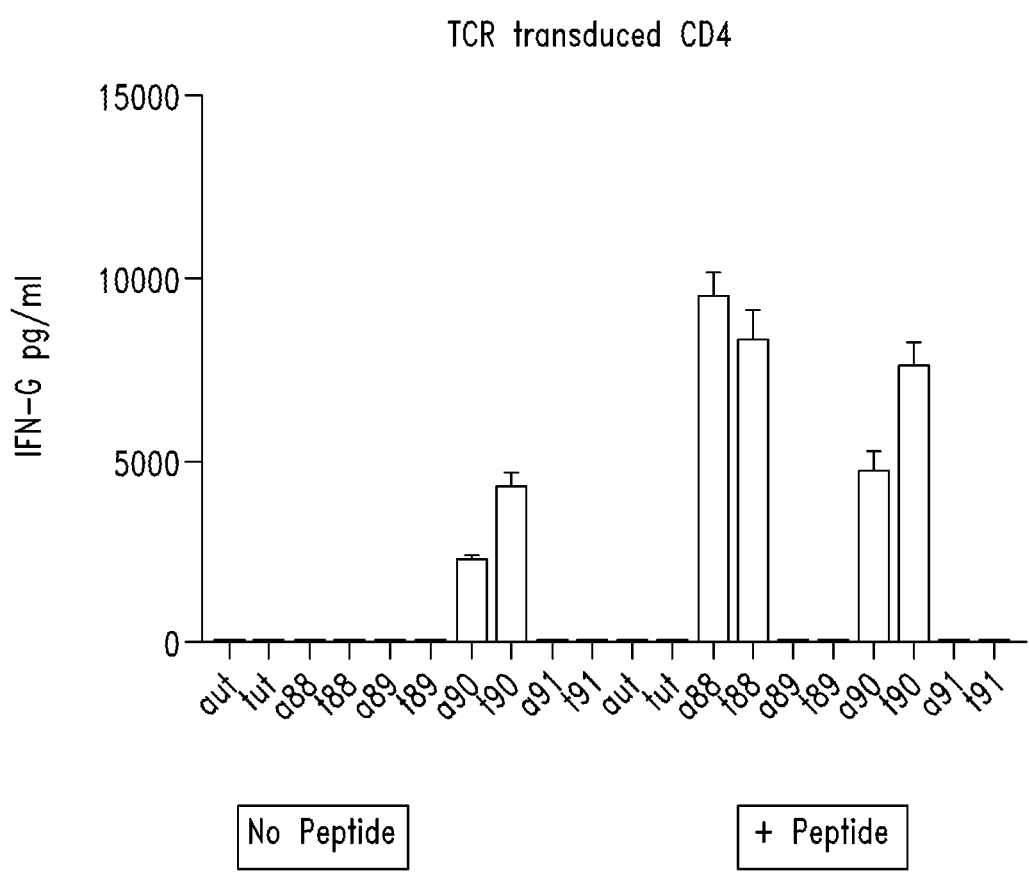
FIG. 5 shows IFN-γ production by CD4+ T cells transduced with one of four TCRs (pJV88-pJV91) made using TCRβ and TCRα genes identified in the patient TILs. Left, no antigen peptide. Right, antigen peptide.

Four (4) TCRs from the three (3) TCRB alleles and four (4) TRCA alleles identified were constructed and tested for antigen-specific response (FIGS. 4A, 4B, and 5). The dominant TCR from the patient (pJV88) was expressed in CD4+ T cells from two healthy donors and conferred specificity to cells expressing BRAF$^{V600E}$ but not wildtype BRAF sequences (FIG. 2H). The TCR pJV90, which was made from the second most dominant Vβ clone from the patient and one of the possible alpha chains, showed some activity but also possibly nonspecific baseline activation.

TCR Vb and Va Sequencing

DNA from clinical samples was isolated using the Qiagen DNeasy or Qiamp micro DNA kits according to the manufacturer's instructions. TCRB sequencing was carried out using the human TCRB sequencing kit (Adaptive Biotechnology) following the manufacturer's instructions and sequenced using a MiSeq (Fred Hutchinson Cancer Research Center Genomics core) with data analysis carried out by Adaptive biotechnology software. TCRA sequencing was carried out using the human TCRA sequencing service (Adaptive Biotechnology).

T Cell Receptor Construction

TCR construction was in the vector PRRL (Jones et al., *Hum. Gene Ther.* 20(6):630-640 (2009)), which was further modified by introducing six point mutations into the start codon and putative promoter region of the woodchuck hepatitis virus X protein as in Lim and Brown, *RNA Biology* 13(9):743-747 (2016)) with the beta chain followed by a P2A translational skip sequence followed by the alpha chain with cysteines introduced to facilitate pairing (see Kuball et al., *Blood* 109(6):2331-2338 (2007)). A codon-optimized DNA fragment containing the TRBV28 and CDR3 and TRBJ1-3 sequences followed by TCRB1 sequence with a cysteine substituted at residue 57 followed by a P2A skip sequence and the TRAV21 and CDR3 sequences followed by TRAJ43 and TRAC sequences was synthesized as a genestring (Life Sciences) and cloned using the NEBuilder cloning kit (New England Biolabs) into the vector PRRL-SIN linearized with PstI and AscI (Thermo Fisher) and sequence verified. One week after transduction, cells were sorted based on Vbeta3.1 expression using antibody clone 8F10 (Thermo Scientific, cat. no. TCR2740) and expanded via rapid expansion as described above. T cells were used in assays or cryopreserved on day 14 of the rapid expansion.

Example 5

Figure 6A:
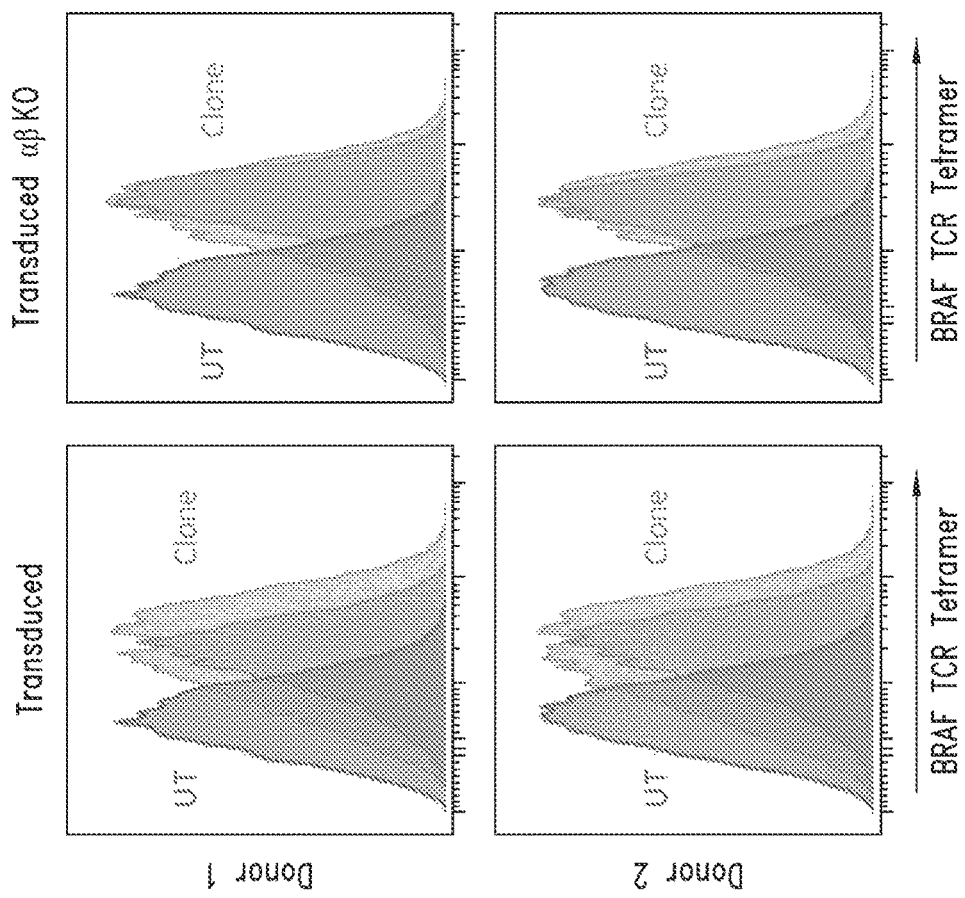
FIGS. 6A and 6B show the effects of CRISPR-mediated knockout of endogenous TCR sequences on expression of a heterologous BRAF-specific TCR in primary human CD4+ T cells. (6A) Stimulated T cells were transfected with Cas9-RNPs targeting TCRA and TCRB and transduced with DNA encoding $BRAF^{V600E}$-specific TCR. BRAF-specific TCR expression was measured by Vbeta3.1 and TCR expression was measured using anti-CD3. Top panels: unmodified cells without (left) or with (right) CRISPR-mediated TCR knockout. Bottom panels: transduced cells without (left) or with (right) CRISPR-mediated TCR knockout. (6B) Tetramer staining: T cells modified with $BRAF^{V600E}$-specific TCR with or without deletion of endogenous TCR were compared to untransduced cells (left-most peaks) and a patient-derived antigen-specific T cell clone (right-most peaks) for binding to tetramer.
Figure 6B:
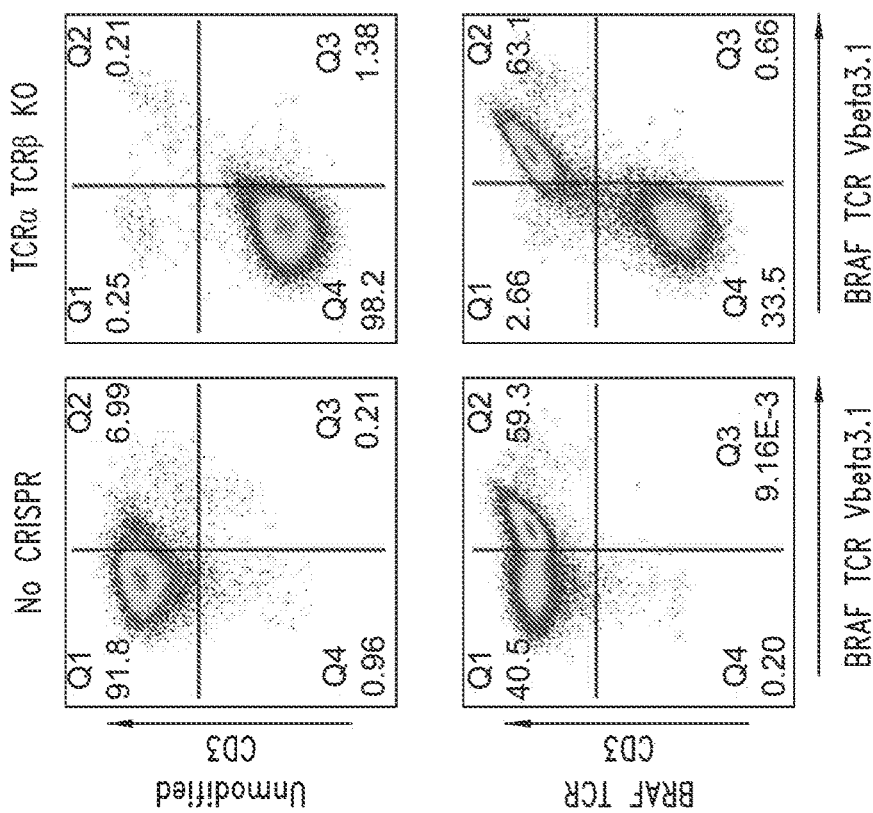

CRISPR-Mediated Deletion of Endogenous TCR Leads to Increased Expression of Transgenic BRAF-Specific TCR Following gene transfer of synthetic T cell receptor sequences into T cells, the transferred TCR alpha and beta chains may compete with endogenous TCR subunits for expression and signaling machinery. To investigate whether deletion of endogenous TCR increased expression of the transferred TCR, stimulated T cells were first transfected with CRISPR-Cas9 ribonucleoproteins with guide RNA sequences directing cleavage of the endogenous TCR alpha (guide rna AGAGTCTCTCAGCTGGTACA; SEQ ID NO:136) and TCR beta (guide rna: GGAGAATGACGAGTGGACCC; SEQ ID NO:139) constant region genes (from Ren et al., *Clin. Cancer Res.* 23(9):2255-2266 (2017)). 12 uM Cas9 protein (IDT) 20 uM guide RNA (IDT) with electroporation enhancer (IDT) was assembled and 3 ul was added to 2e6 primary human T cells 2 days following stimulation with antiCD3/antiCD28 Dynabeads (Thermo-Fisher) in nucleofection buffer P3 (Lonza), and nucleofected using an AMAXA 4D nucleofection electroporator (Lonza) using program EH-115. This combination led to >99% reduction in cells with TCR expression, as measured by staining of the CD3 component of the TCR receptor complex (FIG. 6A). When gene deletion of the endogenous TCR was combined with gene transfer of the BRAF$^{V600E}$-specific TCR increased expression of the transferred T cell receptor on the cell surface was observed, as measured by tetramer staining (FIG. 6B).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/544,695, filed Aug. 11, 2017, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated polynucleotide encoding a binding protein, wherein the binding protein comprises:
   (a) a T cell receptor (TCR) α chain variable (Vα) domain comprising the Vα domain amino acid sequence set forth in SEQ ID NO.:1; and
   (b) a TCR β chain variable (Vβ) domain comprising the Vβ domain amino acid sequence set forth in SEQ ID NO.:5,
   wherein the binding protein is capable of specifically binding to a HLA complex on a cell surface comprising a BRAF peptide containing a $BRAF^{V600E}$ mutation and does not bind a HLA complex on a cell surface comprising a BRAF peptide not containing the $BRAF^{V600E}$ mutation,
   wherein the $BRAF^{V600E}$ peptide consists of the amino acid sequence set forth in SEQ ID NO: 38 or 39,
   wherein the HLA complex comprises (1) HLA-DQA1*03 and (2) HLA-DQB1*0301, HLA-DQB1*0302, or HLA-DQB1*0303, wherein:
   (i) the binding protein comprises a TCR, wherein the Vα domain is comprised in a TCR α chain that further comprises a constant (Cα) domain comprising an introduced cysteine mutation, and the Vβ domain is comprised in a TCR β chain that further comprises a constant (Cβ) domain comprising an introduced cysteine mutation, wherein the introduced cysteine mutations promote pairing of the TCR α chain with the TCR β chain when the binding protein is expressed in a T cell;
   (ii) the polynucleotide comprises a sequence encoding a self-cleaving peptide disposed between a sequence encoding the Vβ domain and a sequence encoding the Vα domain;
   (iii) the polynucleotide is codon optimized for expression in a human T cell; or
   (iv) the binding protein comprises a single chain TCR (scTCR) or a chimeric antigen receptor (CAR).

2. The polynucleotide according to claim 1, wherein the Vα domain is comprised in a TCR α chain that further comprises a constant (Cα) domain comprising an introduced cysteine mutation, and the Vβ domain is comprised in a TCR β chain that further comprises a constant (Cβ) domain comprising an introduced cysteine mutation, wherein the introduced cysteine mutations promote pairing of the TCR α chain with the TCR β chain when the binding protein is expressed in a T cell.

3. The polynucleotide according to claim 1, wherein the polynucleotide is codon optimized for expression in a human T cell.

4. The polynucleotide according to claim 1, wherein the binding protein is a TCR, an antigen-binding fragment of a TCR, or a chimeric antigen receptor.

5. The polynucleotide according to claim 4, wherein the binding protein is a TCR and comprises (i) an α chain constant (Cα) domain comprising the amino acid sequence of SEQ ID NO:25 and (ii) a β chain (Cβ) constant domain comprising the amino acid sequence of SEQ ID NO: 26.

6. An isolated polynucleotide encoding a TCR, wherein the TCR comprises (i) a TCR α chain that comprises the amino acid sequence set forth in SEQ ID NO: 55 and (ii) a TCR β chain that comprises the amino acid sequence set forth in SEQ ID NO: 59.

7. An expression vector, comprising a polynucleotide encoding a binding protein, wherein the binding protein comprises:
   (a) a T cell receptor (TCR) α chain variable (Vα) domain comprising the Vα domain amino acid sequence set forth in SEQ ID NO.:1; and
   (b) a TCR β chain variable (Vβ) domain comprising the Vβ domain amino acid sequence set forth in SEQ ID NO.:5,
   wherein the binding protein is capable of specifically binding to a HLA complex on a cell surface comprising a BRAF peptide containing a $BRAF^{V600E}$ mutation and does not bind a HLA complex on a cell surface comprising a BRAF peptide not containing the $BRAF^{V600E}$ mutation,
   wherein the $BRAF^{V600E}$ peptide consists of the amino acid sequence set forth in SEQ ID NO: 38 or 39,
   wherein the HLA complex comprises (1) HLA-DQA1*03 and (2) HLA-DQB1*0301, HLA-DQB1*0302, or HLA-DQB1*0303,
   and wherein:
   (i) the expression vector (1) comprises an expression control element that is operably coupled to the polynucleotide and is heterologous to the polynucleotide, and/or (2) comprises a viral vector, a bacterial vector, a plasmid, or a cosmid;
   (ii) the binding protein comprises a TCR, wherein the Vα domain is comprised in a TCR α chain that further comprises a constant (Cα) domain comprising an introduced cysteine mutation, and the Vβ domain is comprised in a TCR β chain that further comprises a constant (Cβ) domain comprising an introduced cysteine mutation, wherein the introduced cysteine mutations promote pairing of the TCR α chain with the TCR β chain when the binding protein is expressed in a T cell;
   iii) the polynucleotide comprises a sequence encoding a self-cleaving peptide disposed between a sequence encoding the VB domain and a sequence encoding the Vα domain;
   (iv) the polynucleotide is codon optimized for expression in a human T cell; and/or
   (v) the binding protein comprises a single chain TCR (scTCR) or a chimeric antigen receptor (CAR).

8. A host cell, comprising a polynucleotide according to claim 1, wherein the host cell expresses on its cell surface the encoded binding protein.

9. A host cell comprising a heterologous polynucleotide encoding a binding protein, wherein the encoded binding protein comprises:

(a) a T cell receptor (TCR) α chain variable (Vα) domain comprising the Vα domain amino acid sequence set forth in SEQ ID NO:1, and (b) a TCR β chain variable (Vβ) domain comprising the Vβ domain amino acid sequence set forth in SEQ ID NO:5, wherein the binding protein is capable of specifically binding to a HLA complex on a cell surface comprising a BRAF peptide containing a BRAF$^{V600E}$ mutation and does not bind a HLA complex on a cell surface comprising a BRAF peptide not containing the BRAF$^{V600E}$ mutation, wherein the BRAF$^{V600E}$ peptide consists of the amino acid sequence set forth in SEQ ID NO: 38 or 39, wherein the HLA complex comprises (1) HLA-DQA1*03 and (2) HLA-DQB1*0301, HLA-DQB1*0302, or HLA-DQB1*0303.

10. The host cell according to claim 9, wherein the host cell comprises a CD4+ T cell, a CD8+ T cell, a CD4− CD8− double negative T cell, a γδ T cell, a natural killer cell, a dendritic cell, or any combination thereof.

11. The host cell according to claim 9, wherein the host cell is a hematopoietic progenitor cell or an immune system cell.

12. The host cell according to claim 9, wherein the encoded binding protein comprises: a TCR α chain that comprises or consists of the amino acid sequence set forth in SEQ ID NO.:55; and a TCR β chain that comprises or consists of the amino acid sequence set forth in SEQ ID NO.:59.

13. A CD4+ or CD8+ T cell encoding the amino acid sequence of SEQ ID NO.:69.

14. The host cell according to claim 8, wherein the host cell comprises a T cell.

15. A vector comprising the polynucleotide of claim 1, wherein the vector comprises a lentiviral vector or a retroviral vector.

16. The host cell according to claim 9, wherein the binding protein is a TCR and the host cell comprises a CD4+ T cell.

* * * * *

UNITED STATES PATENT AND TRADEMARK OFFICE
CERTIFICATE OF CORRECTION

PATENT NO. : 12,398,191 B2  
APPLICATION NO. : 16/638339  
DATED : August 26, 2025  
INVENTOR(S) : Joshua Veatch et al.

Page 1 of 1

It is certified that error appears in the above-identified patent and that said Letters Patent is hereby corrected as shown below:

In the Claims

Column 168, Claim 7, Line 56:
"VB" should read: -- V$\beta$ --.

Signed and Sealed this  
Fourth Day of November, 2025

John A. Squires  
*Director of the United States Patent and Trademark Office*